US010870925B2

(12) United States Patent
Boutell et al.

(10) Patent No.: US 10,870,925 B2
(45) Date of Patent: Dec. 22, 2020

(54) ARRAYS

(71) Applicant: SENGENICS CORPORATION PTE LTD, Paya Lebar Square (SG)

(72) Inventors: Jonathan Mark Boutell, Bishop's Stortford (GB); Benjamin Leslie James Godber, Cambridge (GB); Darren James Hart, Cambridgeshire (GB); Jonathan Michael Blackburn, Cambridge (GB)

(73) Assignee: SENGENICS CORPORATION PTE LTD, Singapore (SG)

( * ) Notice: Subject to any disclaimer, the term of this patent is extended or adjusted under 35 U.S.C. 154(b) by 0 days.

(21) Appl. No.: 15/944,625

(22) Filed: Apr. 3, 2018

(65) Prior Publication Data

US 2018/0305840 A1    Oct. 25, 2018

Related U.S. Application Data

(62) Division of application No. 10/313,963, filed on Dec. 5, 2002, now abandoned.

(60) Provisional application No. 60/335,806, filed on Dec. 5, 2001, provisional application No. 60/410,815, filed on Sep. 16, 2002.

(51) Int. Cl.
| | | |
|---|---|---|
| *C40B 30/04* | (2006.01) | |
| *B01J 19/00* | (2006.01) | |
| *G01N 33/68* | (2006.01) | |
| *C12Q 1/6837* | (2018.01) | |
| *C40B 40/06* | (2006.01) | |
| *C40B 40/10* | (2006.01) | |
| *C40B 60/14* | (2006.01) | |

(52) U.S. Cl.
CPC .......... *C40B 30/04* (2013.01); *B01J 19/0046* (2013.01); *G01N 33/6845* (2013.01); *B01J 2219/005* (2013.01); *B01J 2219/0061* (2013.01); *B01J 2219/0063* (2013.01); *B01J 2219/00387* (2013.01); *B01J 2219/00527* (2013.01); *B01J 2219/00574* (2013.01); *B01J 2219/00576* (2013.01); *B01J 2219/00585* (2013.01); *B01J 2219/00596* (2013.01); *B01J 2219/00605* (2013.01); *B01J 2219/00641* (2013.01); *B01J 2219/00644* (2013.01); *B01J 2219/00659* (2013.01); *B01J 2219/00677* (2013.01); *B01J 2219/00691* (2013.01); *B01J 2219/00707* (2013.01); *B01J 2219/00722* (2013.01); *B01J 2219/00725* (2013.01); *C12Q 1/6837* (2013.01); *C40B 40/06* (2013.01); *C40B 40/10* (2013.01); *C40B 60/14* (2013.01); *G01N 2500/00* (2013.01)

(58) Field of Classification Search
None
See application file for complete search history.

(56) References Cited

U.S. PATENT DOCUMENTS

| | | | |
|---|---|---|---|
| 5,412,087 A | 5/1995 | McGall et al. | |
| 5,912,120 A | 6/1999 | Goldstein et al. | |
| 6,117,978 A * | 9/2000 | St. George-Hyslop | A01K 67/0275 |
| | | | 530/350 |
| 6,197,599 B1 | 3/2001 | Chin et al. | |
| 6,692,908 B1 * | 2/2004 | Foung ................. | C07K 14/005 |
| | | | 435/339 |
| 6,808,938 B2 | 10/2004 | Hamalainen et al. | |
| 7,057,165 B2 | 6/2006 | Koopmann | |
| 7,094,568 B2 | 8/2006 | Kolzlowski | |
| 7,816,098 B2 | 10/2010 | Blackburn et al. | |
| 2001/0055764 A1 | 12/2001 | Empedocles et al. | |
| 2003/0118994 A1 | 6/2003 | Blackburn | |
| 2003/0162284 A1 | 8/2003 | Dordick et al. | |
| 2003/0228709 A1 | 12/2003 | Kolzlowski et al. | |
| 2005/0181449 A1 | 8/2005 | Kolzlowski et al. | |
| 2005/0221308 A1 | 10/2005 | Samaddar et al. | |
| 2006/0024791 A1 | 2/2006 | Kolzlowski et al. | |
| 2006/0194715 A1 | 8/2006 | Blackburn | |
| 2006/0275855 A1 | 12/2006 | Blackburn | |
| 2009/0239761 A1 | 9/2009 | Blackburn | |

FOREIGN PATENT DOCUMENTS

| | | |
|---|---|---|
| JP | 2000-184888 | 7/2000 |
| JP | 2002-520621 | 7/2002 |
| JP | 2003-521922 | 7/2003 |

(Continued)

OTHER PUBLICATIONS

Ko et al (Cancer Research 61:4398-404) (Year: 2001).*

(Continued)

*Primary Examiner* — Christopher M Gross

(74) *Attorney, Agent, or Firm* — Nixon & Vanderhye

(57) ABSTRACT

Protein arrays and their use to assay, in a parallel fashion, the protein products of highly homologous or related DNA coding sequences and described. By highly homologous or related it is meant those DNA coding sequences which share a common sequence and which differ only by one or more naturally occurring mutations such as single nucleotide polymorphisms, deletions or insertions, or those sequences which are considered to be haplotypes. Such highly homologous or related DNA coding sequences are generally naturally occurring variants of the same gene. Arrays according to the invention have two or more individual proteins deposited in a spatially defined pattern on a surface in a form whereby a property such as an activity or function of the proteins can be investigated or assayed in parallel by interrogation of the array.

14 Claims, 27 Drawing Sheets

Specification includes a Sequence Listing.

(56) References Cited

FOREIGN PATENT DOCUMENTS

| | | |
|---|---|---|
| JP | 2004-511753 | 4/2004 |
| JP | 2004-527229 | 9/2004 |
| JP | 2005-505241 | 2/2005 |
| WO | WO 92/00311 | 1/1992 |
| WO | WO 99/46403 | 9/1999 |
| WO | WO 00/04382 | 1/2000 |
| WO | WO 00/004390 | 1/2000 |
| WO | WO 01/029220 | 4/2001 |
| WO | WO 01/057198 | 8/2001 |
| WO | WO 01/57198 | 8/2001 |
| WO | WO 2001/061040 | 8/2001 |
| WO | WO 01/83827 | 11/2001 |
| WO | WO 02/053775 | 7/2002 |
| WO | WO 02/064796 | 8/2002 |
| WO | WO 2002/066685 | 8/2002 |
| WO | WO 02/099099 | 12/2002 |
| WO | WO 04/025244 | 3/2004 |

OTHER PUBLICATIONS

Carson et al (JBC 258:9510-3) (Year: 1983).*
Nilsson et al (J. Molecular Recognition 9:585-94) (Year: 1996).
Weiss et al (Protein Expression and Purification 5:509-17) (Year: 1994).
Ariyoshi et al (2001 Biochemical and Biophysical Research Communications 281 :810-4).
Haab et al (2001 Genome Biology 2:research0004.1-0004.13; published Jan. 22, 2001).
Haab et al (2000 Genome Biology 1 :preprint 0001.1-0001.22; published on-line Nov. 17, 2000).
Current Protocols in Molecular Biology (Ausubel, FM et al., eds., vol. 1, Chapter 8).
R. Kozlowski et al, U.S. Appl. No. 12/784,214, filed May 20, 2010, entitled "Arrays".
Einarson, M.B. and Orlinick, J.R. "Identification of Protein-Protein Interactions with Glutathione-S-Transferase (GST) Fusion Proteins", A Molecular Cloning Manual; Cold Spring Harb. Protoc.; 2007, pp. 37-57.
Game, S.M. et al. "Scintillation proximity assay for E-, P-, and L-selectin utilizing polyacrylamide-based neoglycoconjugates as ligands"; Anal. Biochem., Apr. 10, 1998;258(1 ):127-35.
Vikis, H.G. and Guan, K.-I. (2004), "Glutathione-S-Transferase-Fusion Based Assays for studying protein-protein interactions", Protein-Protein Interactions, Methods and Applications, Methods in Molecular Biology, 261, Fu, J. Ed. Humana Press, Totowa, N.J., pp. 175-186.
Aithal et al. (1999), The Lancet, 353:717-719, Association of Polymorph isms in ihe Cytochrome P450 CYP2C9 with Warfarin Dose Requirement and Risk of Bleeding Complications.
Aklillu et al. (1996), the Journal of Pharmacology and Experimental Therapeutics, 278:441-446, Frequent distribution of Ultrarapid Metabolizers of Debrisoquine in an Ethiopian Population Carrying Duplicated and Multiduplicated Functional CYP2D6 Alleles.
Bottger et al. (1997), J. Mol. Biol., 269:744-756, Molecular Characterization of the hdm2-p53 Interaction.
Buetow (2001), Proc. Natl. Acad. Sci. USA, 98:581-584, High-Throughput Development and characterization of a Genomewide Collection of Gene-Based Single Nucleotide Polymorphism Markers by Chip-Based Matrix-Assisted Laser Desorptionllonization Time-of-Flight Mass Spectrometry.
Chakravarti (2001), Nature, 409:822-823, Single Nucleotide Polymorphisms . . . To a Future of Genetic Medicine.
Dai et al. (2001), J Pharmacol. Exp. Ther., 299:825-831, Identification of Variants of CYP3A4 and Characterization of their Abilities to Metabolize Testosterone and Chlorpyrifos.
Dandara et al. (2001), Eur J Clin Phamacol., 57: 11-17, Genetic Polymorphism of CYP2D6 and CYP2C19 in East- and Southern African Populations Including Psychiatric Patients.
Davison et al. (1998), Oncogene, 17:651-656, Characterization of the Oligomerization Defects of Two p53 Mutants Found in Families with Li-Fraumeni and Li-Fraumeni-Like Syndrome.
Dickmann et al. (2001), Mol Pharmacol., 60:382-387, Molecular Pharmacology, 60:382-387, Identification and Functional Characterization of a New CYP2C9 Variant (CYP2C9*5) Expressed Among African Americans.
Eiselt et al. (2001), Pharmacogenetics, 11 :447-458, Identification and Functional Characterization of Eight CYP3A4 Protein Variants.
Emili et al. (2000), Nature Biotechnology, 18:393:397, Large-Scale Functional Analysis Using Peptide or Protein Arrays.
Griese et al. (1998), Pharmacogenetics, 8:15-26, Assessment of the Predictive Power of Genotypes for the In-Vivo Catalytic Function of CYP2D6 in a German Population.
He et al. (2001), Nucleic Acids Research, 29:1-6, Single Step Generation of Protein Arrays from DNA by cell-free expression and in situ Immobilisation (PISA Method).
Hsieh et al. (2001), Drug Metab. Dispos., 29:268-273, Novel Mutations of CYP3A4 in Chinese.
Imai et al. (2000), Pharmacogenetics, 10:85-89, Polymorphism of the Cytochrome P450 (CYP) 2C9 Gene in Japanese Epileptic Oatients: Genetic Analysis of the CYP2C9 Locus.
Johansson, et al. (1994), Molecular Pharmacology, 46:452-459, Genetic Analysis of the Chinese Cytochrome P4502D Locus: Characterization of Variant CYP2D6 Genes Present in Subjects with Diminished Capacity for Debrisoquine Hydroxylation.
Kodadek (2001), Chemistry and Biology, 8:105-115, Protein Microarrays: Prospects and Problems.
Lindblad-Toh (2000), Nat. Genet., 24:381-386, Large-Scale Discovery and Genotyping of Single-Nucleotide Polymorphisms in the Mouse.
Lomax et al. (1998), Oncogene, 17:643-649, Characterization of p53 Oligomerization Domain Mutations Isolated from Li-Fraumeni and Li-Fraumeni-Like Family Members.
MacBeath et al. (2000), Science, 289:1760-1763, Printing Proteins as Microarrays for High-Throughput Function Determine.
Marez et al. (1997), Pharmacogenetics 7:193-202, Polymorphism of the Cytochrome P450 CYP2D6 Gene in a European Population: Characterization of 48 Mutations and 53 Alleles, their Frequencies and Evolution.
Sachse et al. (1997), Am J Hum., Genet., 60:284-295, Cytochrome P450 206 Variants in Caucasian Population: Allele Frequencies and Phenotypic Consequences.
Sata et al. (2000), Clin. Pharmacol. Ther., 67:48-56, CYP3A4 Allelic Variants with Amino Acid Substitutions in Exons 7 and 12: Evidence for an Allelic Variant with Altered Catalytic Activity.
Shi (2001), Clin. Chem., 47:164-172, Enabling Large-Scale Pharmacogenetic Studies by High-Throughput Mutation Detection and Genotyping Technologies.
The International Human Genome Mapping Consortium (2001) Nature, 409:860-921, Initial Sequencing and Analysis of the Human Genome.
The International SNP Map Working Group (2001) Nature, 409:928-933, A Map of Human Genome Sequence Variation Containing 1.42 Million Single Nucleotide Polymorphisms.
Venter (2001), Science, 291:1304-1351, The Sequence of Human Genome.
Wolf et al. (1999), Metabolic Polymorph isms and Susceptibility to Cancer, Chapter 18, Cytochrome P450 CYP2D6, No. 148, pp. 209-229.
Zhu et al. (2000), Nature Genetics, 26:283-289, Analysis of Yeast Protein Kinases Using Protein Chips.
Zhu et al. (2001), Science, 293:2101-2105,Global Analysis of Protein Activities Using Proteome Chips.
Tanaka., Journal of Clinical Pharmacy and Therapeutics. vol. 24: 323-329; 1999.
MacBeath et al., US Science. vol. 289: 1760-1763; Sep. 2000.
Stephen and Lane (1992). J. Mol. Bioi. 225: 577-583.
Toepart at al. (2001). Angew. Chem. Int. Ed. 40: 897-900.
Arenkov et al., "Protein Microchips: Use for Immunoassay and Enzymatic Reactions", Feb. 15, 2000, Analytical Biochemistry, vol. 278, Issue 2, pp. 123-131.

(56) References Cited

OTHER PUBLICATIONS

Cambridge Dictionaries Online, http://dictionary.cambridge.org.
Webster's II New Riverside University Dictionary, 1994, Houghton Mifflin Comapny, p. 249.

* cited by examiner

3A)

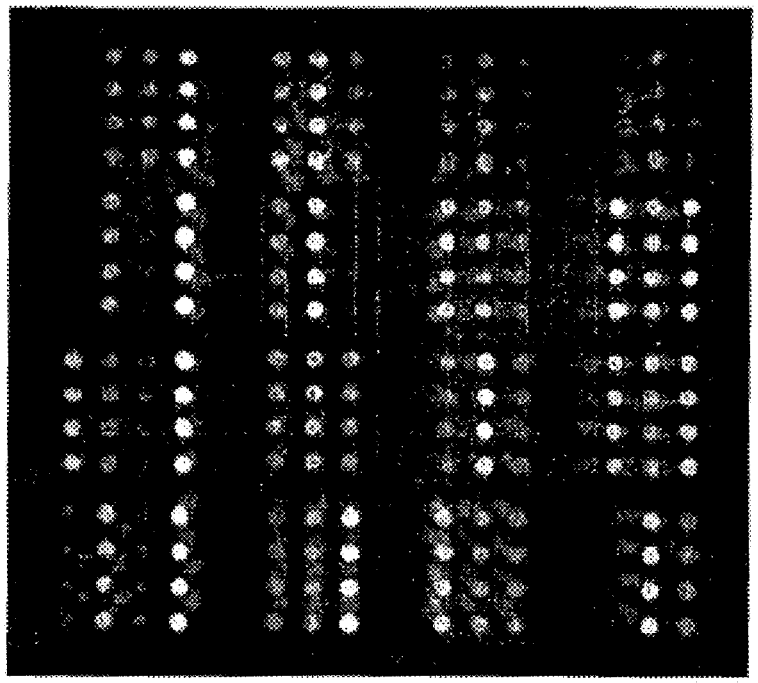
3C)
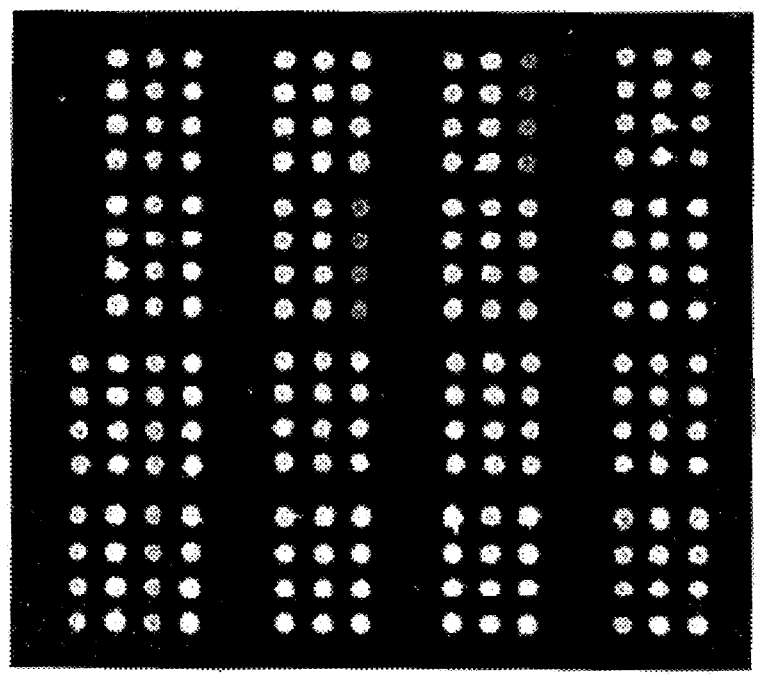
3B)
Figure 3 (continued)

```
   1 CTCGAGAAAT CATAAAAAAT TTATTTGCTT TGTGAGCGGA TAACAATTAT AATAGATTCA
  61 ATTGTGAGCG GATAACAATT TCACACAGAA TTCATTAAAG AGGAGAAATT AACTATGGCA
 121 CTTAGTGGGA TCCGCATGCG AGCTCGGTAC CCCGGGGGTG GCAGCGGTTC TGGCGCAGCA
 181 GCGGAAATCA GTGGTCACAT CGTACGTTCC CCGATGGTTG GTACTTTCTA CCGCACCCCA
 241 AGCCCGGACG CAAAAGCGTT CATCGAAGTG GGTCAGAAAG TCAACGTGGG CGATACCCTG
 301 TGCATCGTTG AAGCCATGAA AATGATGAAC CAGATCGAAG CGGACAAATC CGGTACCGTG
 361 AAAGCAATTC TGGTCGAAAG TGGACAACCG GTAGAATTTG ACGAGCCGCT GGTCGTCATC
 421 GAGGGTGGCA GCGGTTCTGG CCACCATCAC CATCACCATA AGCTTAATTA GCTGAGCTTG
 481 GACTCCTGTT GATAGATCCA GTAATGACCT CAGAACTCCA TCTGGATTTG TTCAGAACGC
 541 TCGGTTGCCG CCGGGCGTTT TTTATTGGTG AGAATCCAAG CTAGCTTGGC GAGATTTTCA
 601 GGAGCTAAGG AAGCTAAAAT GGAGAAAAAA ATCACTGGAT ATACCACCGT TGATATATCC
 661 CAATGGCATC GTAAAGAACA TTTTGAGGCA TTTCAGTCAG TTGCTCAATG TACCTATAAC
 721 CAGACCGTTC AGCTGGATAT TACGGCCTTT TTAAAGACCG TAAAGAAAAA TAAGCACAAG
 781 TTTTATCCGG CCTTTATTCA CATTCTTGCC CGCCTGATGA ATGCTCATCC GGAATTTCGT
 841 ATGGCAATGA AAGACGGTGA GCTGGTGATA TGGGATAGTG TTCACCCTTG TTACACCGTT
 901 TTCCATGAGC AAACTGAAAC GTTTTCATCG CTCTGGAGTG AATACCACGA CGATTTCCGG
 961 CAGTTTCTAC ACATATATTC GCAAGATGTG GCGTGTTACG GTGAAAACCT GGCCTATTTC
1021 CCTAAAGGGT TTATTGAGAA TATGTTTTTC GTCTCAGCCA ATCCCTGGGT GAGTTTCACC
1081 AGTTTTGATT TAAACGTGGC CAATATGGAC AACTTCTTCG CCCCCGTTTT CACCATGGGC
1141 AAATATTATA CGCAAGGCGA CAAGGTGCTG ATGCCGCTGG CGATTCAGGT TCATCATGCC
1201 GTTTGTGATG GCTTCCATGT CGGCAGAATG CTTAATGAAT TACAACAGTA CTGCGATGAG
1261 TGGCAGGGCG GGGCGTAATT TTTTTAAGGC AGTTATTGGT GCCCTTAAAC GCCTGGGGTA
1321 ATGACTCTCT AGCTTGAGGC ATCAAATAAA ACGAAAGGCT CAGTCAAAG ACTGGGCCTT
1381 TCGTTTTATC TGTTGTTTGT CGGTGAACGC TCTCCTGAGT AGGACAAATC CGCCCTCTAG
1441 ATTACGTGCA GTCGATGATA AGCTGTCAAA CATGAGAATT GTGCCTAATG AGTGAGCTAA
1501 CTTACATTAA TTGCGTTGCG CTCACTGCCC GCTTTCCAGT CGGGAAACCT GTCGTGCCAG
1561 CTGCATTAAT GAATCGGCCA ACGCGCGGG AGAGGCGGTT TGCGTATTGG GCGCCAGGGT
1621 GGTTTTTCTT TTCACCAGTG AGACGGGCAA CAGCTGATTG CCCTTCACCG CCTGGCCCTG
1681 AGAGAGTTGC AGCAAGCGGT CCACGCTGGT TTGCCCCAGC AGGCGAAAAT CCTGTTTGAT
1741 GGTGGTTAAC GGCGGGATAT AACATGAGCT GTCTTCGGTA TCGTCGTATC CCACTACCGA
1801 GATATCCGCA CCAACGCGCA GCCCGGACTC GGTAATGGCG CGCATTGCGC CCAGCGCCAT
1861 CTGATCGTTG GCAACCAGCA TCGCAGTGGG AACGATGCCC TCATTCAGCA TTTGCATGGT
1921 TTGTTGAAAA CCGGACATGG CACTCCAGTC GCCTTCCCGT TCCGCTATCG GCTGAATTTG
1981 ATTGCGAGTG AGATATTTAT GCCAGCCAGC CAGACGCAGA CGCGCCGAGA CAGAACTTAA
2041 TGGGCCCGCT AACAGCGCGA TTTGCTGGTG ACCCAATGCG ACCAGATGCT CCACGCCCAG
2101 TCGCGTACCG TCTTCATGGG AGAAAATAAT ACTGTTGATG GGTGTCTGGT CAGAGACATC
2161 AAGAAATAAC GCCGGAACAT TAGTGCAGGC AGCTTCCACA GCAATGGCAT CCTGGTCATC
2221 CAGCGGATAG TTAATGATCA GCCCACTGAC GCGTTGCGCG AGAAGATTGT GCACCGCCGC
2281 TTTACAGGCT TCGACGCCGC TTCGTTCTAC CATCGACACC ACCACGCTGG CACCCAGTTG
2341 ATCGGCGCGA GATTTAATCG CCGCGACAAT TTGCGACGGC GCGTGCAGGG CCAGACTGGA
2401 GGTGGCAACG CCAATCAGCA ACGACTGTTT GCCCGCCAGT TGTTGTGCCA CGCGGTTGGG
2461 AATGTAATTC AGCTCCGCCA TCGCCGCTTC CACTTTTTCC CGCGTTTTCG CAGAAACGTG
2521 GCTGGCCTGG TTCACCACGC GGGAAACGGT CTGATAAGAG ACACCGGCAT ACTCTGCGAC
2581 ATCGTATAAC GTTACTGGTT TCACATTCAC CACCCTGAAT TGACTCTCTT CCGGGCGCTA
2641 TCATGCCATA CCGCGAAAGG TTTTGCACCA TTCGATGGTG TCGGAATTTC GGGCAGCGTT
2701 GGGTCCTGGC CACGGGTGCG CATGATCTAG AGCTGCCTCG CGCGTTTCGG TGATGACGGT
2761 GAAAACCTCT GACACATGCA GCTCCCGGAG ACGGTCACAG CTTGTCTGTA AGCGGATGCC
2821 GGGAGCAGAC AAGCCCGTCA GGGCGCGTCA GCGGGTGTTG GCGGGTGTCG GGGCGCAGCC
2881 ATGACCCAGT CACGTAGCGA TAGCGGAGTG TATACTGGCT TAACTATGCG GCATCAGAGC
2941 AGATTGTACT GAGAGTGCAC CATATGCGGT GTGAAATACC GCACAGATGC GTAAGGAGAA
3001 AATACCGCAT CAGGCGCTCT TCCGCTTCCT CGCTCACTGA CTCGCTGCGC TCGGTCGTTC
3061 GGCTGCGGCG AGCGGTATCA GCTCACTCAA AGGCGGTAAT ACGGTTATCC ACAGAATCAG
3121 GGGATAACGC AGGAAAGAAC ATGTGAGCAA AAGGCCAGCA AAAGGCCAGG AACCGTAAAA
3181 AGGCCGCGTT GCTGGCGTTT TTCCATAGGC TCCGCCCCCC TGACGAGCAT CACAAAAATC
3241 GACGCTCAAG TCAGAGGTGG CGAAACCCGA CAGGACTATA AAGATACCAG GCGTTTCCCC
3301 CTGGAAGCTC CCTCGTGCGC TCTCCTGTTC CGACCCTGCC GCTTACCGGA TACCTGTCCG
3361 CCTTTCTCCC TTCGGGAAGC GTGGCGCTTT CTCATAGCTC ACGCTGTAGG TATCTCAGTT
3421 CGGTGTAGGT CGTTCGCTCC AAGCTGGGCT GTGTGCACGA ACCCCCCGTT CAGCCCGACC
3481 GCTGCGCCTT ATCCGGTAAC TATCGTCTTG AGTCCAACCC GGTAAGACAC GACTTATCGC
3541 CACTGGCAGC AGCCACTGGT AACAGGATTA GCAGAGCGAG GTATGTAGGC GGTGCTACAG
3601 AGTTCTTGAA GTGGTGGCCT AACTACGGCT ACACTAGAAG GACAGTATTT GGTATCTGCG
3661 CTCTGCTGAA GCCAGTTACC TTCGGAAAAA GAGTTGGTAG CTCTTGATCC GGCAAACAAA
3721 CCACCGCTGG TAGCGGTGGT TTTTTTGTTT GCAAGCAGCA GATTACGCGC AGAAAAAAAG
3781 GATCTCAAGA AGATCCTTTG ATCTTTTCTA CGGGGTCTGA CGCTCAGTGG AACGAAAACT
3841 CACGTTAAGG GATTTTGGTC ATGAGATTAT CAAAAAGGAT CTTCACCTAG ATCCTTTTAA
```

Figure 9B

```
3901 ATTAAAAATG AAGTTTTAAA TCAATCTAAA GTATATATGA GTAAACTTGG TCTGACAGTT
3961 ACCAATGCTT AATCAGTGAG GCACCTATCT CAGCGATCTG TCTATTTCGT TCATCCATAG
4021 TTGCCTGACT CCCCGTCGTG TAGATAACTA CGATACGGGA GGGCTTACCA TCTGGCCCCA
4081 GTGCTGCAAT GATACCGCGA GACCCACGCT CACCGGCTCC AGATTTATCA GCAATAAACC
4141 AGCCAGCCGG AAGGGCCGAG CGCAGAAGTG GTCCTGCAAC TTTATCCGCC TCCATCCAGT
4201 CTATTAATTG TTGCCGGGAA GCTAGAGTAA GTAGTTCGCC AGTTAATAGT TTGCGCAACG
4261 TTGTTGCCAT TGCTACAGGC ATCGTGGTGT CACGCTCGTC GTTTGGTATG GCTTCATTCA
4321 GCTCCGGTTC CCAACGATCA AGGCGAGTTA CATGATCCCC CATGTTGTGC AAAAAAGCGG
4381 TTAGCTCCTT CGGTCCTCCG ATCGTTGTCA GAAGTAAGTT GGCCGCAGTG TTATCACTCA
4441 TGGTTATGGC AGCACTGCAT AATTCTCTTA CTGTCATGCC ATCCGTAAGA TGCTTTTCTG
4501 TGACTGGTGA GTACTCAACC AAGTCATTCT GAGAATAGTG TATGCGGCGA CCGAGTTGCT
4561 CTTGCCCGGC GTCAATACGG GATAATACCG CGCCACATAG CAGAACTTTA AAAGTGCTCA
4621 TCATTGGAAA ACGTTCTTCG GGGCGAAAAC TCTCAAGGAT CTTACCGCTG TTGAGATCCA
4681 GTTCGATGTA ACCCACTCGT GCACCCAACT GATCTTCAGC ATCTTTTACT TTCACCAGCG
4741 TTTCTGGGTG AGCAAAAACA GGAAGGCAAA ATGCCGCAAA AAAGGGAATA AGGGCGACAC
4801 GGAAATGTTG AATACTCATA CTCTTCCTTT TTCAATATTA TTGAAGCATT TATCAGGGTT
4861 ATTGTCTCAT GAGCGGATAC ATATTTGAAT GTATTTAGAA AAATAAACAA ATAGGGGTTC
4921 CGCGCACATT TCCCCGAAAA GTGCCACCTG ACGTCTAAGA AACCATTATT ATCATGACAT
4981 TAACCTATAA AATAGGCGT ATCACGAGGC CCTTCGTCT TCAC
```

Figure 9B (continued)

```
            Dra III              Sph I                Sma I
115  ATGGCA CTTAGTGGGA TCCGCATGCG AGCTCGGTAC CCCGGGGGTG GCAGC
     TACCGT GAATCACCCT AGGCGTACGC TCGAGCCATG GGGCCCCCAC CGTCG
```

Figure 9C

```
   1 CAGGTGGCAC TTTTCGGGGA AATGTGCGCG GAACCCCTAT TTGTTTATTT TTCTAAATAC
  61 ATTCAAATAT GTATCCGCTC ATGAGACAAT AACCCTGATA AATGCTTCAA TAATATTGAA
 121 AAAGGAAGAG TATGAGTATT CAACATTTCC GTGTCGCCCT TATTCCCTTT TTTGCGGCAT
 181 TTTGCCTTCC TGTTTTTGCT CACCCAGAAA CGCTGGTGAA AGTAAAAGAT GCTGAAGATC
 241 AGTTGGGTGC ACGAGTGGGT TACATCGAAC TGGATCTCAA CAGCGGTAAG ATCCTTGAGA
 301 GTTTTCGCCC CGAAGAACGT TTTCCAATGA TGAGCACTTT TAAAGTTCTG CTATGTGGCG
 361 CGGTATTATC CCGTATTGAC GCCGGGCAAG AGCAACTCGG TCGCCGCATA CACTATTCTC
 421 AGAATGACTT GGTTGAGTAC TCACCAGTCA CAGAAAAGCA TCTTACGGAT GGCATGACAG
 481 TAAGAGAATT ATGCAGTGCT GCCATAACCA TGAGTGATAA CACTGCGGCC AACTTACTTC
 541 TGACAACGAT CGGAGGACCG AAGGAGCTAA CCGCTTTTTT GCACAACATG GGGGATCATG
 601 TAACTCGCCT TGATCGTTGG GAACCGGAGC TGAATGAAGC CATACCAAAC GACGAGCGTG
 661 ACACCACGAT GCCTGTAGCA ATGGCAACAA CGTTGCGCAA ACTATTAACT GGCGAACTAC
 721 TTACTCTAGC TTCCCGGCAA CAATTAATAG ACTGGATGGA GGCGGATAAA GTTGCAGGAC
 781 CACTTCTGCG CTCGGCCCTT CCGGCTGGCT GGTTTATTGC TGATAAATCT GGAGCCGGTG
 841 AGCGTGGGTC TCGCGGTATC ATTGCAGCAC TGGGGCCAGA TGGTAAGCCC TCCCGTATCG
 901 TAGTTATCTA CACGACGGGG AGTCAGGCAA CTATGGATGA ACGAAATAGA CAGATCGCTG
 961 AGATAGGTGC CTCACTGATT AAGCATTGGT AACTGTCAGA CCAAGTTTAC TCATATATAC
1021 TTTAGATTGA TTTAAAACTT CATTTTTAAT TTAAAAGGAT CTAGGTGAAG ATCCTTTTTG
1081 ATAATCTCAT GACCAAAATC CCTTAACGTG AGTTTTCGTT CCACTGAGCG TCAGACCCCG
1141 TAGAAAAGAT CAAAGGATCT TCTTGAGATC CTTTTTTTCT GCGCGTAATC TGCTGCTTGC
1201 AAACAAAAAA ACCACCGCTA CCAGCGGTGG TTTGTTTGCC GGATCAAGAG CTACCAACTC
1261 TTTTTCCGAA GGTAACTGGC TTCAGCAGAG CGCAGATACC AAATACTGTC CTTCTAGTGT
1321 AGCCGTAGTT AGGCCACCAC TTCAAGAACT CTGTAGCACC GCCTACATAC CTCGCTCTGC
1381 TAATCCTGTT ACCAGTGGCT GCTGCCAGTG GCGATAAGTC GTGTCTTACC GGGTTGGACT
1441 CAAGACGATA GTTACCGGAT AAGGCGCAGC GGTCGGGCTG AACGGGGGGT TCGTGCACAC
1501 AGCCCAGCTT GGAGCGAACG ACCTACACCG AACTGAGATA CCTACAGCGT GAGCATTGAG
1561 AAAGCGCCAC GCTTCCCGAA GGGAGAAAGG CGGACAGGTA TCCGGTAAGC GGCAGGGTCG
1621 GAACAGGAGA GCGCACGAGG GAGCTTCCAG GGGGAAACGC CTGGTATCTT TATAGTCCTG
1681 TCGGGTTTCG CCACCTCTGA CTTGAGCGTC GATTTTTGTG ATGCTCGTCA GGGGGGCGGA
1741 GCCTATGGAA AAACGCCAGC AACGCGGCCT TTTTACGGTT CCTGGCCTTT TGCTGGCCTT
1801 TTGCTCACAT GTTCTTTCCT GCGTTATCCC CTGATTCTGT GGATAACCGT ATTACCGCCT
1861 TTGAGTGAGC TGATACCGCT CGCCGCAGCC GAACGACCGA GCGCAGCGAG TCAGTGAGCG
1921 AGGAAGCCCA GGACCCAACG CTGCCCGAAA TTCCGACACC ATCGAATGGT GCAAAACCTT
1981 TCGCGGTATG GCATGATAGC GCCCGGAAGA GAGTCAATTC AGGGTGGTGA ATGTGAAACC
2041 AGTAACGTTA TACGATGTCG CAGAGTATGC CGGTGTCTCT TATCAGACCG TTTCCCGCGT
2101 GGTGAACCAG GCCAGCCACG TTTCTGCGAA AACGCGGGAA AAAGTGGAAG CGGCGATGGC
2161 GGAGCTGAAT TACATTCCCA ACCGCGTGGC ACAACAACTG GCGGGCAAAC AGTCGTTGCT
2221 GATTGGCGTT GCCACCTCCA GTCTGGCCCT GCACGCGCCG TCGCAAATTG TCGCGGCGAT
2281 TAAATCTCGC GCCGATCAAC TGGGTGCCAG CGTGGTGGTG TCGATGGTAG AACGAAGCGG
2341 CGTCGAAGCC TGTAAAGCGG CGGTGCACAA TCTTCTCGCG CAACGCGTCA GTGGGCTGAT
2401 CATTAACTAT CCGCTGGATG ACCAGGATGC CATTGCTGTG GAAGCTGCCT GCACTAATGT
2461 TCCGGCGTTA TTTCTTGATG TCTCTGACCA GACACCCATC AACAGTATTA TTTTCTCCCA
2521 TGAAGACGGT ACGCGACTGG GCGTGGAGCA TCTGGTCGCA TTGGGTCACC AGCAAATCGC
```

Figure 10B

```
2581 GCTGTTAGCG GGCCCATTAA GTTCTGTCTC GGCGCGTCTG CGTCTGGCTG GCTGGCATAA
2641 ATATCTCACT CGCAATCAAA TTCAGCCGAT AGCGGAACGG GAAGGCGACT GGAGTGCCAT
2701 GTCCGGTTTT CAACAAACCA TGCAAATGCT GAATGAGGGC ATCGTTCCCA CTGCGATGCT
2761 GGTTGCCAAC GATCAGATGG CGCTGGGCGC AATGCGCGCC ATTACCGAGT CCGGGCTGCG
2821 CGTTGGTGCG GATATCTCGG TAGTGGGATA CGACGATACC GAAGACAGCT CATGTTATAT
2881 CCCGCCGTTA ACCACCATCA AACAGGATTT TCGCCTGCTG GGGCAAACCA GCGTGGACCG
2941 CTTGCTGCAA CTCTCTCAGG GCCAGGCGGT GAAGGGCAAT CAGCTGTTGC CCGTCTCACT
3001 GGTGAAAAGA AAAACCACCC TGGCGCCCAA TACGCAAACC GCCTCTCCCC GCGCGTTGGC
3061 CGATTCATTA ATGCAGCTGG CACGACAGGT TTCCCGACTG GAAAGCGGGC AGTGAGCGCA
3121 ACGCAATTAA TGTGAGTTAG CTCACTCATT AGGCACAATT CTCATGTTTG ACAGCTTATC
3181 ATCGACTGCA CGGTGCACCA ATGCTTCTGG CGTCAGGCAG CCATCGGAAG CTGTGGTATG
3241 GCTGTGCAGG TCGTAAATCA CTGCATAATT CGTGTCGCTC AAGGCGCACT CCCGTTCTGG
3301 ATAATGTTTT TTGCGCCGAC ATCATAACGG TTCTGGCAAA TATTCTGAAA TGAGCTGTTG
3361 ACAATTAATC ATCGGCTCGT ATAATGTGTG GAATTGTGAG CGGATAACAA TTTCACACAG
3421 GAAACACATA TGAACGACTT TCATCGCGAT ACGTGGGCGG AAGTGGATTT GGACGCCATT
3481 TACGACAATG TGGCGAATTT GCGCCGTTTG CTGCCGGACG ACACGCACAT TATGGCGGTC
3541 GTGAAGGCGA ACGCCTATGG ACATGGGGAT GTGCAGGTGG CAAGGACAGC GCTCGAAGCG
3601 GGGGCCTCCC GCCTGGCGGT TGCCTTTTTG GATGAGGCGC TCGCTTTAAG GGAAAAAGGA
3661 ATCGAAGCGC CGATTCTAGT TCTCGGGGCT TCCCGTCCAG CTGATGCGGC GCTGGCCGCC
3721 CAGCAGCGCA TTGCCCTGAC CGTGTTCCGC TCCGACTGGT TGGAAGAAGC GTCCGCCCTT
3781 TACAGCGGCC CTATTCCTAT TCATTTCCAT TTGAAAATGG ACACCGGCAT GGGACGGCTT
3841 GGAGTGAAAG ACGAGGAGGA GACGAAACGA ATCGCAGCGC TGATTGAGCG CCATCCGCAT
3901 TTTGTGCTTG AAGGGGCGTA CACGCATTTT GCGACTGCGG ATGAGGTGAA CACCGATTAT
3961 TTTTCCTATC AGTATACCCG TTTTTTGCAC ATGCTCGAAT GGCTGCCGTC GCGCCCGCCG
4021 CTCGTCCATT GCGCCAACAG CGCAGCGTCG CTCCGTTTCC CTGACCGGAC GTTCAATATG
4081 GTCCGCTTCG GCATTGCCAT GTATGGGCTT GCCCCGTCGC CCGGCATCAA GCCGCTGCTG
4141 CCGTATCCAT TAAAAGAAGC ATTTTCGCTC CATAGCCGCC TCGTACACGT CAAAAAACTG
4201 CAACCAGGCG AAAAGGTGAG CTATGGTGCG ACGTACACTG CGCAGACGGA GGAGTGGATC
4261 GGGACGATTC CGATCGGCTA TGCGGACGGC TGGCTCCGCC GCCTGCAGCA CTTTCATGTC
4321 CTTGTTGACG GACAAAAGGC GCCGATTGTC GGCCGCATTT GCATGGACCA GTGCATGATC
4381 CGCCTGCCTG GGCCGCTGCC GGTCGGCACG AAGGTGACAC TGATTGGTCG CCAGGGGGAC
4441 GAGGTAATTT CCATTGATGA TGTCGCTCGC CATTTGGAAA CGATCAACTA CGAAGTGCCT
4501 TGCACGATCA GCTATCGAGT GCCCCGTATT TTTTTCCGCC ATAAGCGTAT AATGGAAGTG
4561 AGAAACGCCA TTGGCCGCGG GGAAAGCAGT GCACATCACC ATCACCATCA CTAAAAGCTT
4621 GGATCCGAAT TCAGCCCGCC TAATGAGCGG GCTTTTTTTT GAACAAAATT AGCTTGGCTG
4681 TTTTGGCGGA TGAGAGAAGA
```

**Figure 10B
(continued)**

```
1     ATGGCTCTCA TCCCAGACTT GGCCATGGAA ACCTGGCTTC TCCTGGCTGT CAGCCTGGTG
61    CTCCTCTATC TATATGGAAC CCATTCACAT GGACTTTTTA AGAAGCTTGG AATTCCAGGG
121   CCCACACCTC TGCCTTTTTT GGGAAATATT TTGTCCTACC ATAAGGGCTT TTGTATGTTT
181   GACATGGAAT GTCATAAAAA GTATGGAAAA GTGTGGGGCT TTTATGATGG TCAACAGCCT
241   GTGCTGGCTA TCACAGATCC TGACATGATC AAAACAGTGC TAGTGAAAGA ATGTTATTCT
301   GTCTTCACAA ACCGGAGGCC TTTTGGTCCA GTGGGATTTA TGAAAAGTGC CATCTCTATA
361   GCTGAGGATG AAGAATGGAA GAGATTACGA TCATTGCTGT CTCCAACCTT CACCAGTGGA
421   AAACTCAAGG AGATGGTCCC TATCATTGCC CAGTATGGAG ATGTGTTGGT GAGAAATCTG
481   AGGCGGGAAG CAGAGACAGG CAAGCCTGTC ACCTTGAAAG ACGTCTTTGG GGCCTACAGC
541   ATGGATGTGA TCACTAGCAC ATCATTTGGA GTGAACATCG ACTCTCTCAA CAATCCACAA
601   GACCCCTTTG TGGAAAACAC CAAGAAGCTT TTAAGATTTG ATTTTTTGGA TCCATTCTTT
661   CTCTCAATAA CAGTCTTTCC ATTCCTCATC CCAATTCTTG AAGTATTAAA TATCTGTGTG
721   TTTCCAAGAG AAGTTACAAA TTTTTTAAGA AAATCTGTAA AAAGGATGAA AGAAAGTCGC
781   CTCGAAGATA CACAAAAGCA CCGAGTGGAT TTCCTTCAGC TGATGATTGA CTCTCAGAAT
841   TCAAAAGAAA CTGAGTCCCA CAAAGCTCTG TCCGATCTGG AGCTCGTGGC CCAATCAATT
901   ATCTTTATTT TTGCTGGCTA TGAAACCACG AGCAGTGTTC TCTCCTTCAT TATGTATGAA
961   CTGGCCACTC ACCCTGATGT CCAGCAGAAA CTGCAGGAGG AAATTGATGC AGTTTTACCC
1021  AATAAGGCAC CACCCACCTA TGATACTGTG CTACAGATGG AGTATCTTGA CATGGTGGTG
1081  AATGAAACGC TCAGATTATT CCCAATTGCT ATGAGACTTG AGAGGGTCTG CAAAAAAGAT
1141  GTTGAGATCA ATGGGATGTT CATTCCCAAA GGGGTGGTGG TGATGATTCC AAGCTATGCT
1201  CTTCACCGTG ACCCAAAGTA CTGGACAGAG CCTGAGAAGT TCCTCCCTGA AGATTCAGC
1261  AAGAAGAACA AGGACAACAT AGATCCTTAC ATATACACAC CCTTTGGAAG TGGACCCAGA
1321  AACTGCATTG GCATGAGGTT TGCTCTCATG AACATGAAAC TTGCTCTAAT CAGAGTCCTT
1381  CAGAACTTCT CCTTCAAACC TTGTAAAGAA ACACAGATCC CCTGAAATT AAGCTTAGGA
1441  GGACTTCTTC AACCAGAAAA ACCCGTTGTT CTAAAGGTTG AGTCAAGGGA TGGCACCGTA
1501  AGTGGAGCCT GA
```

Figure 11A

```
1     MALIPDLAME TWLLLAVSLV LLYLYGTHSH GLFKKLGIPG PTPLPFLGNI LSYHKGFCMF
61    DMECHKKYGK VWGFYDGQQP VLAITDPDMI KTVLVKECYS VFTNRRPFGP VGFMKSAISI
121   AEDEEWKRLR SLLSPTFTSG KLKEMVPIIA QYGDVLVRNL RREAETGKPV TLKDVFGAYS
181   MDVITSTSFG VNIDSLNNPQ DPFVENTKKL LRFDFLDPFF LSITVFPFLI PILEVLNICV
241   FPREVTNFLR KSVKRMKESR LEDTQKHRVD FLQLMIDSQN SKETESHKAL SDLELVAQSI
301   IFIFAGYETT SSVLSFIMYE LATHPDVQQK LQEEIDAVLP NKAPPTYDTV LQMEYLDMVV
361   NETLRLFPIA MRLERVCKKD VEINGMFIPK GVVVMIPSYA LHRDPKYWTE PEKFLPERFS
421   KKNKDNIDPY IYTPFGSGPR NCIGMRFALM NMKLALIRVL QNFSFKPCKE TQIPLKLSLG
481   GLLQPEKPVV LKVESRDGTV SGA*
```

Figure 11B

```
   1 ATGGATTCTC TTGTGGTCCT TGTGCTCTGT CTCTCATGTT TGCTTCTCCT TTCACTCTGG
  61 AGACAGAGCT CTGGGAGAGG AAAACTCCCT CCTGGCCCCA CTCCTCTCCC AGTGATTGGA
 121 AATATCCTAC AGATAGGTAT TAAGGACATC AGCAAATCCT TAACCAATCT CTCAAAGGTC
 181 TATGGCCCGG TGTTCACTCT GTATTTTGGC CTGAAACCCA TAGTGGTGCT GCATGGATAT
 241 GAAGCAGTGA AGGAAGCCCT GATTGATCTT GGAGAGGAGT TTTCTGGAAG AGGCATTTTC
 301 CCACTGGCTG AAAGAGCTAA CAGAGGATTT GGAATTGTTT TCAGCAATGG AAAGAAATGG
 361 AAGGAGATCC GGCGTTTCTC CCTCATGACG CTGCGGAATT TTGGGATGGG GAAGAGGAGC
 421 ATTGAGGACC GTGTTCAAGA GGAAGCCCGC TGCCTTGTGG AGGAGTTGAG AAAAACCAAG
 481 GCCTCACCCT GTGATCCCAC TTTCATCCTG GGCTGTGCTC CCTGCAATGT GATCTGCTCC
 541 ATTATTTTCC ATAAACGTTT TGATTATAAA GATCAGCAAT TTCTTAACTT AATGGAAAAG
 601 TTGAATGAAA ACATCAAGAT TTTGAGCAGC CCTGGATCC AGATCTGCAA TAATTTTTCT
 661 CCTATCATTG ATTACTTCCC GGGAACTCAC AACAAATTAC TTAAAAACGT TGCTTTTATG
 721 AAAAGTTATA TTTTGGAAAA AGTAAAAGAA CACCAAGAAT CAATGGACAT GAACAACCCT
 781 CAGGACTTTA TTGATTGCTT CCTGATGAAA ATGGAGAAGG AAAAGCACAA CCAACCATCT
 841 GAATTTACTA TTGAAAGCTT GGAAAACACT GCAGTTGACT TGTTTGGAGC TGGGACAGAG
 901 ACGACAAGCA CAACCCTGAG ATATGCTCTC CTTCTCCTGC TGAAGCACCC AGAGGTCACA
 961 GCTAAAGTCC AGGAAGAGAT TGAACGTGTG ATTGGCAGAA ACCGGAGCCC CTGCATGCAA
1021 GACAGGAGCC ACATGCCCTA CACAGATGCT GTGGTGCACG AGGTCCAGAG ATACATTGAC
1081 CTTCTCCCCA CCAGCCTGCC CCATGCAGTG ACCTGTGACA TTAAATTCAG AAACTATCTC
1141 ATTCCCAAGG GCACAACCAT ATTAATTTCC CTGACTTCTG TGCTACATGA CAACAAGAA
1201 TTTCCCAACC CAGAGATGTT TGACCCTCAT CACTTTCTGG ATGAAGGTGG CAATTTTAAG
1261 AAAAGTAAAT ACTTCATGCC TTTCTCAGCA GGAAAACGGA TTTGTGTGGG AGAAGCCCTG
1321 GCCGGCATGG AGCTGTTTTT ATTCCTGACC TCCATTTTAC AGAACTTTAA CCTGAAATCT
1381 CTGGTTGACC CAAAGAACCT TGACACCACT CCAGTTGTCA ATGGATTTGC CTCTGTGCCG
1441 CCCTTCTACC AGCTGTGCTT CATTCCTGTC TGAAGAAGAG CAGATGGCCT GGCTGCTGCT
1501 GTGCAGTCCC TGCAGCTCTC TTTCCTCTGG GGCATTATCC ATCTTTGCAC TATCTGTAAT
1561 GCCTTTTCTC ACCTGTCATC TCACATTTTC CCTTCCCTGA AGATCTAGTG AACATTCGAC
1621 CTCCATTACG GAGAGTTTCC TATGTTTCAC TGTGCAAATA TATCTGCTAT TCTCCATACT
1681 CTGTAACAGT TGCATTGACT GTCACATAAT GCTCATACTT ATCTAATGTA GAGTATTAAT
1741 ATGTTATTAT TAAATAGAGA AATATGATTT GTGTATTATA ATTCAAAGGC ATTTCTTTTC
1801 TGCATGATCT AAATAAAAAG CATTATTATT TGCTG
```

Figure 12A

```
   1 MDSLVVLVLC LSCLLLLSLW RQSSGRGKLP PGPTPLPVIG NILQIGIKDI SKSLTNLSKV
  61 YGPVFTLYFG LKPIVVLHGY EAVKEALIDL GEEFSGRGIF PLAERANRGF GIVFSNGKKW
 121 KEIRRFSLMT LRNFGMGKRS IEDRVQEEAR CLVEELRKTK ASPCDPTFIL GCAPCNVICS
 181 IIFHKRFDYK DQQFLNLMEK LNENIKILSS PWIQICNNFS PIIDYFPGTH NKLLKNVAFM
 241 KSYILEKVKE HQESMDMNNP QDFIDCFLMK MEKEKHNQPS EFTIESLENT AVDLFGAGTE
 301 TTSTTLRYAL LLLLKHPEVT AKVQEEIERV IGRNRSPCMQ DRSHMPYTDA VVHEVQRYID
 361 LLPTSLPHAV TCDIKFRNYL IPKGTTILIS LTSVLHDNKE FPNPEMFDPH HFLDEGGNFK
 421 KSKYFMPFSA GKRICVGEAL AGMELFLFLT SILQNFNLKS LVDPKNLDTT PVVNGFASVP
 481 PFYQLCFIPV *RRADGLAAA VQSLQLSFLW GIIHLCTICN AFSHLSSHIF PSLKI**TFD
 541 LHYGEFPMFH CANISAILHT L*QLH*LSHN AHTYLM*SIN MLLLNREI*F VYYNSKAFLF
 601 CMI*IKSIII C
```

Figure 12B

```
   1 ATGGGGCTAG AAGCACTGGT GCCCCTGGCC GTGATAGTGG CCATCTTCCT GCTCCTGGTG
  61 GACCTGATGC ACCGGCGCCA ACGCTGGGCT GCACGCTACC CACCAGGCCC CCTGCCACTG
 121 CCCGGGCTGG GCAACCTGCT GCATGTGGAC TTCCAGAACA CCACCATACTG CTTCGACCAG
 181 TTGCGGCGCC GCTTCGGGGA CGTGTTCAGC CTGCAGCTGG CCTGGACGCC GGTGGTCGTG
 241 CTCAATGGGC TGGCGGCCGT GCGCGAGGCG CTGGTGACCC ACGGCGAGGA CACCGCCGAC
 301 CGCCCGCCTG TGCCCATCAC CCAGATCCTG GGTTTCGGGC CGCGTTCCCA AGGGGTGTTC
 361 CTGGCGCGCT ATGGGCCCGC GTGGCGCGAG CAGAGGCGCT TCTCCGTGTC CACCTTGCGC
 421 AACTTGGGCC TGGGCAAGAA GTCGCTGGAG CAGTGGGTGA CCGAGGAGGC CGCCTGCCTT
 481 TGTGCCGCCT TCGCCAACCA CTCCGGACGC CCCTTTCGCC CAACGGTCT CTTGGACAAA
 541 GCCGTGAGCA ACGTGATCGC CTCCCTCACC TGCGGGCGCC GCTTCGAGTA CGACGACCCT
 601 CGCTTCCTCA GGCTGCTGGA CCTAGCTCAG GAGGGACTGA AGGAGGAGTC GGGCTTTCTG
 661 CGCGAGGTGC TGAATGCTGT CCCCGTCCTC CTGCATATCC AGCGCTGGC TGGCAAGGTC
 721 CTACGCTTCC AAAAGGCTTT CCTGACCCAG CTGGATGAGC TGCTAACTGA GCACAGGATG
 781 ACCTGGGACC CAGCCCAGCC CCCCCGAGAC CTGACTGAGG CCTTCCTGGC AGAGATGGAG
 841 AAGGCCAAGG GGAACCCTGA GAGCAGCTTC AATGATGAGA ACCTGCGCAT AGTGGTGGCT
 901 GACCTGTTCT CTGCCGGGAT GGTGACCACC TCGACCACGC TGGCCTGGGG CCTCCTGCTC
 961 ATGATCCTAC ATCCGGATGT GCAGCGCCGT GTCCAACAGG AGATCGACGA CGTGATAGGG
1021 CAGGTGCGGC GACCAGAGAT GGGTGACCAG GCTCACATGC CCTACACCAC TGCCGTGATT
1081 CATGAGGTGC AGCGCTTTGG GGACATCGTC CCCCTGGGTA TGACCCATAT GACATCCCGT
1141 GACATCGAAG TACAGGGCTT CCGCATCCCT AAGGGAACGA CACTCATCAC CAACCTGTCA
1201 TCGGTGCTGA AGGATGAGGC CGTCTGGGAG AAGCCCTTCC GCTTCCACCC CGAACACTTC
1261 CTGGATGCCC AGGGCCACTT TGTGAAGCCG GAGGCCTTCC TGCCTTTCTC AGCAGGCCGC
1321 CGTGCATGCC TCGGGGAGCC CCTGGCCCGC ATGGAGCTCT TCCTCTTCTT CACCTCCCTG
1381 CTGCAGCACT TCAGCTTCTC GGTGCCCACT GGACAGCCCC GGCCCAGCCA CCATGGTGTC
1441 TTTGCTTTCC TGGTGAGCCC ATCCCCTAT GAGCTTTGTG CTGTGCCCCG CTAG
```

Figure 13A

```
   1 MGLEALVPLA VIVAIFLLLV DLMHRRQRWA ARYPPGPLPL PGLGNLLHVD FQNTPYCFDQ
  61 LRRRFGDVFS LQLAWTPVVV LNGLAAVREA LVTHGEDTAD RPPVPITQIL GFGPRSQGVF
 121 LARYGPAWRE QRRFSVSTLR NLGLGKKSLE QWVTEEAACL CAAFANHSGR PFRPNGLLDK
 181 AVSNVIASLT CGRRFEYDDP RFLRLLDLAQ EGLKEESGFL REVLNAVPVL LHIPALAGKV
 241 LRFQKAFLTQ LDELLTEHRM TWDPAQPPRD LTEAFLAEME KAKGNPESSF NDENLRIVVA
 301 DLFSAGMVTT STTLAWGLLL MILHPDVQRR VQQEIDDVIG QVRRPEMGDQ AHMPYTTAVI
 361 HEVQRFGDIV PLGMTHMTSR DIEVQGFRIP KGTTLITNLS SVLKDEAVWE KPFRFHPEHF
 421 LDAQGHFVKP EAFLPFSAGR RACLGEPLAR MELFLFFTSL LQHFSFSVPT GQPRPSHHGV
           481 FAFLVSPSPY ELCAVPR*
```

Figure 13B

SEQUENCE LISTING

```
<160> NUMBER OF SEQ ID NOS: 66

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence:  Synthetic
      primer

<400> SEQUENCE: 1
atggaggagc cgcagtcaga tcctag                                          26

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence:  Synthetic
      primer

<400> SEQUENCE: 2
gatcgcggcc gctcagtcag gcccttctg                                       29

<210> SEQ ID NO 3
<211> LENGTH: 30
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 3
gtacagaaca tgtctaagca tgctggggac                              30

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gtccccagca tgcttagaca tgttctgtac                              30

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gctgcacgct acccaccagg ccccctg                                 27

<210> SEQ ID NO 6
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ttgcggccgc tcttctacta gcggggcaca gcacaaagct catag             45

<210> SEQ ID NO 7
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tattctcact ggccattacg gccgctgcac gctacccacc aggccccctg        50

<210> SEQ ID NO 8
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tattctcact ggccattacg gccgtggacc tgatgcaccg gcgccaacgc tgggctgcac    60
gctacccacc aggccccctg                                         80

<210> SEQ ID NO 9
<211> LENGTH: 107

-continued

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tattctcact ggccattacg gccatggctc tagaagcact ggtgcccctg gccgtgatag      60
tggccatctt cctgctcctg gtggacctga tgcaccggcg ccaacgc                  107

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gcggggcaca gcacaaagct cataggg                                         27

<210> SEQ ID NO 11
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctccctcctg gccccactcc tctcccaa                                        28

<210> SEQ ID NO 12
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tttgcggccg ctcttctatc agacaggaat gaagcacagc ctggta                    46

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cttggaattc cagggcccac acctctg                                         27

<210> SEQ ID NO 14
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tttgcggccg ctcttctatc aggctccact tacggtgcca tcccttga                  48

<210> SEQ ID NO 15
```

```
<211> LENGTH: 83
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tattctcact ggccattacg gcctatggaa cccattcaca tggactttt aagaagcttg    60 gaattccagg gcccacacct ctg                                          83

<210> SEQ ID NO 16
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tattctcact ggccattacg gcccttggaa ttcagggcc cacacctctg               50

<210> SEQ ID NO 17
<211> LENGTH: 85
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ttctcactgg ccattacggc ccctcctggc tgtcagcctg gtgctcctct atctatatgg   60
aacccattca catggacttt ttagg                                        85

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggctccactt acggtgccat cccttgac                                     28

<210> SEQ ID NO 19
<211> LENGTH: 75
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tattctcact ggccattacg gccagacaga gctctgggag aggaaaactc cctcctggcc   60
ccactcctct cccag                                                   75

<210> SEQ ID NO 20
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
```
tattctcact ggccattacg gccctccctc ctggccccac tcctctccca g    51

<210> SEQ ID NO 21
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gacaggaatg aagcacagct ggtagaagg    29

<210> SEQ ID NO 22
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ctctcatgtt tgcttctcct ttcactctgg agacagcgct ctgggagagg aaaactc    57

<210> SEQ ID NO 23
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
acagagcaca aggaccacaa gagaatcggc cgtaagtgcc atagttaatt tctc    54

<210> SEQ ID NO 24
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ggatcgacat atgggagact cccacgtgga cac    33

<210> SEQ ID NO 25
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ccgataagct tatcagctcc acacgtccag ggag    34

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tgtgttcaag aggaagcccg ctg                                          23

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gtcctcaatg ctgctcttcc ccatc                                        25

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cttgaccttc tccccaccag cctg                                         24

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gtatctctgg acctcgtgca ccac                                         24

<210> SEQ ID NO 30
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ctgaccttct ccccaccagc ctg                                          23

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tgtatctctg gacctcgtgc ac                                           22

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gcttctcccc accagcctgc                                              20

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tcaatgtatc tctggacctc gtgc                                           24

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gcattgacct tctccccacc agc                                            23

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
caccacgtgc tccaggtctc ta                                             22

<210> SEQ ID NO 36
<211> LENGTH: 79
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ttctcactgg ccattacggc cgtggacctg atgcaccggc gccaacgctg ggctgcacgc    60
tactcaccag gccccctgc                                                 79

<210> SEQ ID NO 37
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gcggggcaca gcacaaagct cataggggga tgggctcacc aggaaagcaa ag            52

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tccagatcct gggtttcggg c                                           21

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tgatgggcac aggcgggcgg tc                                          22

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gccaagggga accctgagag c                                           21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ctccatctct gccaggaagg c                                           21

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ccaataagag tctttccatt cctc                                        24

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gagaaagaat ggatccaaaa aatc                                        24

<210> SEQ ID NO 44
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
cgaggtttgc tctcatgacc atg                                         23

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
tgccaatgca gtttctgggt ccac                                          24

<210> SEQ ID NO 46
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gtctctatag ctgaggatga ag                                            22

<210> SEQ ID NO 47
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47 ggcactttc ataaatccca ctg                                            23

<210> SEQ ID NO 48
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gattctttct ctcaataaca gtc                                           23

<210> SEQ ID NO 49
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gatccaaaaa atcaaatctt aaa                                           23

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
aggaagcaga gacaggcaag c                                             21

<210> SEQ ID NO 51
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 51
gcctcagatt tctcaccaac ac                                              22

<210> SEQ ID NO 52
<211> LENGTH: 5024
<212> TYPE: DNA
<213> ORGANISM: Artificial Sequence
<220> FEATURE:
<223> OTHER INFORMATION: Description of Artificial Sequence: Synthetic DNA sequence of pBJW102.2

<400> SEQUENCE: 52

| | | |
|---|---|---|
| ctcgagaaat cataaaaaat ttatttgctt tgtgagcgga taacaattat aatagattca | 60 |
| attgtgagcg ataacaatt tcacacagaa ttcattaaag aggagaaatt aactatggca | 120 |
| cttagtggga tccgcatgcg agctcggtac cccgggggtg gcagcggttc tggcgcagca | 180 |
| gcggaaatca gtggtcacat cgtacgttcc ccgatggttg gtactttcta ccgcacccca | 240 |
| agcccggacg caaaagcgtt catcgaagtg ggtcagaaag tcaacgtggg cgataccctg | 300 |
| tgcatcgttg aagccatgaa atgatgaac cagatcgaag cggacaaatc cggtaccgtg | 360 |
| aaagcaattc tggtcgaaag tggacaaccg gtagaatttg acgagccgct ggtcgtcatc | 420 |
| gagggtggca gcggttctgg ccaccatcac catcaccata gcttaatta gctgagcttg | 480 |
| gactcctgtt gatagatcca gtaatgacct cagaactcca tctggatttg ttcagaacgc | 540 |
| tcggttgccg ccgggcgttt tttattggtg agaatccaag ctagcttggc gagattttca | 600 |
| ggagctaagg aagctaaaat ggagaaaaaa atcactggat ataccaccgt tgatatatcc | 660 |
| caatggcatc gtaaagaaca ttttgaggca tttcagtcag ttgctcaatg tacctataac | 720 |
| cagaccgttc agctggatat tacggccttt ttaaagaccg taaagaaaaa taagcacaag | 780 |
| ttttatccgg cctttattca cattcttgcc cgcctgatga atgctcatcc ggaatttcgt | 840 |
| atggcaatga agacggtga gctggtgata tgggatagtg ttcacccttg ttacaccgtt | 900 |
| ttccatgagc aaactgaaac gttttcatcg ctctggagtg aataccacga cgatttccgg | 960 |
| cagtttctac acatatattc gcaagatgtg gcgtgttacg gtgaaaacct ggcctatttc | 1020 |
| cctaaagggt ttattgagaa tatgttttc gtctcagcca tccctgggt gagtttcacc | 1080 |
| agttttgatt taaacgtggc caatatggac aacttcttcg ccccgttttt caccatgggc | 1140 |
| aaatattata cgcaaggcga caaggtgctg atgccgctgg cgattcaggt tcatcatgcc | 1200 |
| gtttgtgatg gcttccatgt cggcagaatg cttaatgaat tacaacagta ctgcgatgag | 1260 |
| tggcagggcg ggcgtaatt tttttaaggc agttattggt gcccttaaac gcctggggta | 1320 |
| atgactctct agcttgaggc atcaaataaa acgaaaggct cagtcgaaag actgggcctt | 1380 |
| tcgttttatc tgttgtttgt cggtgaacgc tctcctgagt aggacaaatc cgccctctag | 1440 |
| attacgtgca gtcgatgata agctgtcaaa catgagaatt gtgcctaatg agtgagctaa | 1500 |
| cttacattaa ttgcgttgcg ctcactgccc gctttccagt cgggaaacct gtcgtgccag | 1560 |
| ctgcattaat gaatcggcca acgcgcgggg agaggcggtt tgcgtattgg gcgccagggt | 1620 |
| ggtttttctt ttcaccagtg agacgggcaa cagctgattg cccttcaccg cctggccctg | 1680 |

```
agagagttgc agcaagcggt ccacgctggt ttgccccagc aggcgaaaat cctgtttgat      1740
ggtggttaac ggcgggatat aacatgagct gtcttcggta tcgtcgtatc ccactaccga      1800
gatatccgca ccaacgcgca gcccggactc ggtaatggcg cgcattgcgc ccagcgccat      1860
ctgatcgttg caaccagca tcgcagtggg aacgatgccc tcattcagca tttgcatggt      1920
ttgttgaaaa ccggacatgg cactccagtc gccttcccgt tccgctatcg gctgaatttg      1980
attgcgagtg agatatttat gccagccagc cagacgcaga cgcgccgaga cagaacttaa      2040
tgggcccgct aacagcgcga tttgctggtg acccaatgcg accagatgct ccacgcccag      2100
tcgcgtaccg tcttcatggg agaaaataat actgttgatg ggtgtctggt cagagacatc      2160
aagaaataac gccggaacat tagtgcaggc agcttccaca gcaatggcat cctggtcatc      2220
cagcggatag ttaatgatca gcccactgac gcgttgcgcg agaagattgt gcaccgccgc      2280
tttacaggct tcgacgccgc ttcgttctac catcgacacc accacgctgg cacccagttg      2340
atcggcgcga gatttaatcg ccgcgacaat ttgcgacggc gcgtgcaggg ccagactgga      2400
ggtggcaacg ccaatcagca acgactgttt gcccgccagt tgttgtgcca cgcggttggg      2460
aatgtaattc agctccgcca tcgccgcttc cactttttcc cgcgttttcg cagaaacgtg      2520
gctggcctgg ttcaccacgc gggaaacggt ctgataagag acaccggcat actctgcgac      2580
atcgtataac gttactggtt tcacattcac caccctgaat tgactctctt ccgggcgcta      2640
tcatgccata ccgcgaaagg ttttgcacca ttcgatggtg tcggaatttc gggcagcgtt      2700
gggtcctggc cacgggtgcg catgatctag agctgcctcg cgcgtttcgg tgatgacggt      2760
gaaaacctct gacacatgca gctcccggag acggtcacag cttgtctgta agcggatgcc      2820
gggagcagac aagcccgtca gggcgcgtca gcgggtgttg gcgggtgtcg gggcgcagcc      2880
atgacccagt cacgtagcga tagcggagtg tatactggct taactatgcg gcatcagagc      2940
agattgtact gagagtgcac catatgcggt gtgaaatacc gcacagatgc gtaaggagaa      3000
aataccgcat caggcgctct ccgcttcct cgctcactga ctcgctgcgc tcggtcgttc      3060
ggctgcggcg agcggtatca gctcactcaa aggcggtaat acggttatcc acagaatcag      3120
gggataacgc aggaaagaac atgtgagcaa aaggccagca aaaggccagg aaccgtaaaa      3180
aggccgcgtt gctggcgttt ttccataggc tccgcccccc tgacgagcat cacaaaaatc      3240
gacgctcaag tcagaggtgg cgaaacccga caggactata agataccag gcgtttcccc      3300 ctggaagctc cctcgtgcgc tctcctgttc cgaccctgcc gcttaccgga tacctgtccg      3360
cctttctccc ttcgggaagc gtggcgcttt ctcatagctc acgctgtagg tatctcagtt      3420
cggtgtaggt cgttcgctcc aagctgggct gtgtgcacga accccccgtt cagcccgacc      3480
gctgcgcctt atccggtaac tatcgtcttg agtccaaccc ggtaagacac gacttatcgc      3540
cactggcagc agccactggt aacaggatta gcagagcgag gtatgtaggc ggtgctacag      3600
agttcttgaa gtggtggcct aactacggct acactagaag gacagtattt ggtatctgcg      3660
ctctgctgaa gccagttacc ttcggaaaaa gagttggtag ctcttgatcc ggcaaacaaa      3720
ccaccgctgg tagcggtggt ttttttgttt gcaagcagca gattacgcgc agaaaaaaag      3780
gatctcaaga agatcctttg atcttttcta cggggtctga cgctcagtgg aacgaaaact      3840
cacgttaagg gattttggtc atgagattat caaaaaggat cttcacctag atcctttaa       3900 attaaaaatg aagttttaaa tcaatctaaa gtatatatga gtaaacttgg tctgacagtt      3960
accaatgctt aatcagtgag gcacctatct cagcgatctg tctatttcgt tcatccatag      4020
```

```
ttgcctgact ccccgtcgtg tagataacta cgatacggga gggcttacca tctggcccca    4080
gtgctgcaat gataccgcga gacccacgct caccggctcc agatttatca gcaataaacc    4140
agccagccgg aagggccgag cgcagaagtg gtcctgcaac tttatccgcc tccatccagt    4200
ctattaattg ttgccgggaa gctagagtaa gtagttcgcc agttaatagt ttgcgcaacg    4260
ttgttgccat tgctacaggc atcgtggtgt cacgctcgtc gtttggtatg gcttcattca    4320
gctccggttc ccaacgatca aggcgagtta catgatcccc catgttgtgc aaaaaagcgg    4380
ttagctcctt cggtcctccg atcgttgtca gaagtaagtt ggccgcagtg ttatcactca    4440
tggttatggc agcactgcat aattctctta ctgtcatgcc atccgtaaga tgcttttctg    4500
tgactggtga gtactcaacc aagtcattct gagaatagtg tatgcggcga ccgagttgct    4560
cttgcccggc gtcaatacgg gataataccg cgccacatag cagaacttta aaagtgctca    4620
tcattggaaa acgttcttcg ggcgaaaac tctcaaggat cttaccgctg ttgagatcca    4680
gttcgatgta acccactcgt gcacccaact gatcttcagc atcttttact ttcaccagcg    4740
tttctgggtg agcaaaaaca ggaaggcaaa atgccgcaaa aaagggaata agggcgacac    4800
ggaaatgttg aatactcata ctcttccttt ttcaatatta ttgaagcatt tatcagggtt    4860
attgtctcat gagcggatac atatttgaat gtatttagaa aaataaacaa ataggggttc    4920
cgcgcacatt tccccgaaaa gtgccacctg acgtctaaga aaccattatt atcatgacat    4980
taacctataa aaataggcgt atcacgaggc cctttcgtct tcac                    5024

<210> SEQ ID NO 53
<211> LENGTH: 51
<212> TYPE: DNA
<213> ORGANISM: Artificial Sequence
<220> FEATURE:
<223> OTHER INFORMATION: Description of Artificial Sequence: Synthetic
      cloning site of pBJW102.2

<400> SEQUENCE: 53
atggcactta gtgggatccg catgcgagct cggtaccccg ggggtggcag c              51

<210> SEQ ID NO 54
<211> LENGTH: 4700
<212> TYPE: DNA
<213> ORGANISM: Artificial Sequence
<220> FEATURE:
<223> OTHER INFORMATION: Description of Artificial Sequence: Synthetic
      DNA sequence of the vector pBJW102.2

<400> SEQUENCE: 54
caggtggcac ttttcgggga aatgtgcgcg gaacccctat ttgtttattt ttctaaatac      60
attcaaatat gtatccgctc atgagacaat aaccctgata aatgcttcaa taatattgaa     120
aaaggaagag tatgagtatt caacatttcc gtgtcgccct tattccctttt tttgcggcat    180 tttgccttcc tgttttttgct cacccagaaa cgctggtgaa agtaaaagat gctgaagatc    240
agttgggtgc acgagtgggt tacatcgaac tggatctcaa cagcggtaag atccttgaga    300
gttttcgccc cgaagaacgt tttccaatga tgagcacttt taaagttctg ctatgtggcg    360
cggtattatc ccgtattgac gccgggcaag agcaactcgg tcgccgcata cactattctc    420
agaatgactt ggttgagtac tcaccagtca cagaaaagca tcttacggat ggcatgacag    480
taagagaatt atgcagtgct gccataacca tgagtgataa cactgcggcc aacttacttc    540
tgacaacgat cggaggaccg aaggagctaa ccgcttttttt gcacaacatg ggggatcatg    600
taactcgcct tgatcgttgg gaaccggagc tgaatgaagc cataccaaac gacgagcgtg    660
```

```
acaccacgat gcctgtagca atggcaacaa cgttgcgcaa actattaact ggcgaactac    720
ttactctagc ttcccggcaa caattaatag actggatgga ggcggataaa gttgcaggac    780
cacttctgcg ctcggccctt ccggctggct ggtttattgc tgataaatct ggagccggtg    840
agcgtgggtc tcgcggtatc attgcagcac tggggccaga tggtaagccc tcccgtatcg    900
tagttatcta cacgacgggg agtcaggcaa ctatggatga acgaaataga cagatcgctg    960
agataggtgc ctcactgatt aagcattggt aactgtcaga ccaagtttac tcatatatac   1020
tttagattga tttaaaactt cattttaat ttaaaaggat ctaggtgaag atccttttg   1080 ataatctcat gaccaaaatc ccttaacgtg agttttcgtt ccactgagcg tcagaccccg   1140
tagaaaagat caaaggatct tcttgagatc ctttttttct gcgcgtaatc tgctgcttgc   1200
aaacaaaaaa accaccgcta ccagcggtgg tttgtttgcc ggatcaagag ctaccaactc   1260
tttttccgaa ggtaactggc ttcagcagag cgcagatacc aaatactgtc cttctagtgt   1320
agccgtagtt aggccaccac ttcaagaact ctgtagcacc gcctacatac ctcgctctgc   1380
taatcctgtt accagtggct gctgccagtg gcgataagtc gtgtcttacc gggttggact   1440
caagacgata gttaccggat aaggcgcagc ggtcgggctg aacggggggt tcgtgcacac   1500
agcccagctt ggagcgaacg acctacaccg aactgagata cctacagcgt gagcattgag   1560
aaagcgccac gcttcccgaa gggagaaagg cggacaggta tccggtaagc ggcagggtcg   1620
gaacaggaga gcgcacgagg gagcttccag ggggaaacgc ctggtatctt tatagtcctg   1680
tcgggtttcg ccacctctga cttgagcgtc gatttttgtg atgctcgtca ggggggcgga   1740
gcctatggaa aaacgccagc aacgcggcct ttttacggtt cctggccttt tgctggcctt   1800
ttgctcacat gttctttcct gcgttatccc ctgattctgt ggataaccgt attaccgcct   1860
ttgagtgagc tgataccgct cgccgcagcc gaacgaccga gcgcagcgag tcagtgagcg   1920
aggaagccca ggacccaacg ctgcccgaaa ttccgacacc atcgaatggt gcaaaacctt   1980
tcgcggtatg gcatgatagc gcccggaaga gagtcaattc agggtggtga atgtgaaacc   2040
agtaacgtta tacgatgtcg cagagtatgc cggtgtctct tatcagaccg tttcccgcgt   2100
ggtgaaccag gccagccacg tttctgcgaa aacgcgggaa aaagtggaag cggcgatggc   2160
ggagctgaat tacattccca accgcgtggc acaacaactg gcgggcaaac agtcgttgct   2220
gattggcgtt gccacctcca gtctggccct gcacgcgccg tcgcaaattg tcgcggcgat   2280
taaatctcgc gccgatcaac tgggtgccag cgtggtggtg tcgatggtag aacgaagcgg   2340
cgtcgaagcc tgtaaagcgg cggtgcacaa tcttctcgcg caacgcgtca gtgggctgat   2400
cattaactat ccgctggatg accaggatgc cattgctgtg gaagctgcct gcactaatgt   2460
tccggcgtta tttcttgatg tctctgacca gacacccatc aacagtatta ttttctccca   2520
tgaagacggt acgcgactgg gcgtggagca tctggtcgca ttgggtcacc agcaaatcgc   2580
gctgttagcg ggcccattaa gttctgtctc ggcgcgtctg cgtctggctg ctggcataa   2640 atatctcact cgcaatcaaa ttcagccgat agcggaacgg gaaggcgact ggagtgccat   2700
gtccggtttt caacaaacca tgcaaatgct gaatgagggc atcgttccca ctgcgatgct   2760
ggttgccaac gatcagatgg cgctgggcgc aatgcgcgcc attaccgagt ccgggctgcg   2820
cgttggtgcg gatatctcgg tagtgggata cgacgatacc gaagacagct catgttatat   2880
cccgccgtta accaccatca aacaggattt tcgcctgctg ggcaaaccag cgtggaccg   2940 cttgctgcaa ctctctcagg ccaggcggt gaagggcaat cagctgttgc ccgtctcact   3000
```

```
ggtgaaaaga aaaaccaccc tggcgcccaa tacgcaaacc gcctctcccc gcgcgttggc    3060
cgattcatta atgcagctgg cacgacaggt ttcccgactg gaaagcgggc agtgagcgca    3120
acgcaattaa tgtgagttag ctcactcatt aggcacaatt ctcatgtttg acagcttatc    3180
atcgactgca cggtgcacca atgcttctgg cgtcaggcag ccatcggaag ctgtggtatg    3240
gctgtgcagg tcgtaaatca ctgcataatt cgtgtcgctc aaggcgcact cccgttctgg    3300
ataatgtttt ttgcgccgac atcataacgg ttctggcaaa tattctgaaa tgagctgttg    3360
acaattaatc atcggctcgt ataatgtgtg gaattgtgag cggataacaa tttcacacag    3420
gaaacacata tgaacgactt tcatcgcgat acgtgggcgg aagtggattt ggacgccatt    3480
tacgacaatg tggcgaattt gcgccgtttg ctgccggacg acacgcacat tatggcggtc    3540
gtgaaggcga acgcctatgg acatggggat gtgcaggtgg caaggacagc gctcgaagcg    3600
ggggcctccc gcctggcggt tgccttttg  gatgaggcgc tcgctttaag ggaaaaagga    3660
atcgaagcgc cgattctagt tctcggggct tcccgtccag ctgatgcggc gctggccgcc    3720
cagcagcgca ttgccctgac cgtgttccgc tccgactggt ggaagaagc  gtccgccctt    3780 tacagcggcc ctattcctat tcatttccat ttgaaaatgg acaccggcat gggacggctt    3840
ggagtgaaag acgaggagga gacgaaacga atcgcagcgc tgattgagcg ccatccgcat    3900
tttgtgcttg aaggggcgta cacgcatttt gcgactgcgg atgaggtgaa caccgattat    3960
ttttcctatc agtatacccg tttttttgcac atgctcgaat ggctgccgtc gcgcccgccg    4020
ctcgtccatt gcgccaacag cgcagcgtcg ctccgttttcc ctgaccggac gttcaatatg    4080
gtccgcttcg gcattgccat gtatgggctt gcccgtcgc  ccggcatcaa gccgctgctg    4140
ccgtatccat taaaagaagc atttcgctc  catagccgcc tcgtacacgt caaaaaactg    4200
caaccaggcg aaaaggtgag ctatggtgcg acgtacactg cgcagacgga ggagtggatc    4260
gggacgattc cgatcggcta tgcggacggc tggctccgcc gcctgcagca ctttcatgtc    4320
cttgttgacg gacaaaaggc gccgattgtc ggccgcattt gcatggacca gtgcatgatc    4380
cgcctgcctg gccgctgcc  ggtcggcacg aaggtgacac tgattggtcg ccaggggac     4440 gaggtaattt ccattgatga tgtcgctcgc catttggaaa cgatcaacta cgaagtgcct    4500
tgcacgatca gctatcgagt gccccgtatt ttttccgcc  ataagcgtat aatggaagtg    4560
agaaacgcca ttggccgcgg ggaaagcagt gcacatcacc atcaccatca ctaaaagctt    4620
ggatccgaat tcagcccgcc taatgagcgg gcttttttt  gaacaaaatt agcttggctg    4680
ttttggcgga tgagagaaga                                                4700
```

<210> SEQ ID NO 55
<211> LENGTH: 1512
<212> TYPE: DNA
<213> ORGANISM: Homo sapiens
<400> SEQUENCE: 55

```
atggctctca tcccagactt ggccatggaa acctggcttc tcctggctgt cagcctggtg      60
ctcctctatc tatatggaac ccattcacat ggactttta  agaagcttgg aattccaggg     120
cccacacctc tgcctttttt gggaaatatt ttgtcctacc ataagggctt tgtatgttt     180 gacatggaat gtcataaaaa gtatggaaaa gtgtggggct tttatgatgg tcaacagcct     240
gtgctggcta tcacagatcc tgacatgatc aaaacagtgc tagtgaaaga atgttattct     300
gtcttcacaa accggaggcc ttttggtcca gtgggattta tgaaaagtgc catctctata     360
gctgaggatg aagaatggaa gagattacga tcattgctgt ctccaacctt caccagtgga     420
```

-continued

```
aaactcaagg agatggtccc tatcattgcc cagtatggag atgtgttggt gagaaatctg      480
aggcgggaag cagagacagg caagcctgtc accttgaaag acgtctttgg ggcctacagc      540
atggatgtga tcactagcac atcatttgga gtgaacatcg actctctcaa caatccacaa      600 gaccccttg tggaaaacac caagaagctt ttaagatttg attttttgga tccattcttt       660
ctctcaataa cagtctttcc attcctcatc ccaattcttg aagtattaaa tatctgtgtg      720
tttccaagag aagttacaaa ttttttaaga aaatctgtaa aaaggatgaa agaaagtcgc      780
ctcgaagata cacaaaagca ccgagtggat tccttcagc tgatgattga ctctcagaat       840
tcaaaagaaa ctgagtccca caaagctctg tccgatctgg agctcgtggc ccaatcaatt     900
atctttattt ttgctggcta tgaaaccacg agcagtgttc tctccttcat tatgtatgaa      960
ctggccactc accctgatgt ccagcagaaa ctgcaggagg aaattgatgc agttttaccc     1020
aataaggcac cacccaccta tgatactgtg ctacagatgg agtatcttga catggtggtg     1080
aatgaaacgc tcagattatt cccaattgct atgagacttg agagggtctg caaaaaagat    1140
gttgagatca atgggatgtt cattcccaaa ggggtggtgg tgatgattcc aagctatgct     1200
cttcaccgtg acccaaagta ctggacagag cctgagaagt tcctccctga agattcagc      1260 aagaagaaca aggacaacat agatccttac atatacacac cctttggaag tggacccaga     1320
aactgcattg gcatgaggtt tgctctcatg aacatgaaac ttgctctaat cagagtcctt     1380
cagaacttct ccttcaaacc ttgtaaagaa acacagatcc ccctgaaatt aagcttagga    1440
ggacttcttc aaccagaaaa acccgttgtt ctaaaggttg agtcaaggga tggcaccgta    1500
agtggagcct ga                                                         1512
```

<210> SEQ ID NO 56
<211> LENGTH: 503
<212> TYPE: PRT
<213> ORGANISM: Homo sapiens

<400> SEQUENCE: 56

```
Met Ala Leu Ile Pro Asp Leu Ala Met Glu Thr Trp Leu Leu Leu Ala
1               5                  10                  15

Val Ser Leu Val Leu Leu Tyr Leu Tyr Gly Thr His Ser His Gly Leu
            20                  25                  30

Phe Lys Lys Leu Gly Ile Pro Gly Pro Thr Pro Leu Pro Phe Leu Gly
        35                  40                  45

Asn Ile Leu Ser Tyr His Lys Gly Phe Cys Met Phe Asp Met Glu Cys
    50                  55                  60

His Lys Lys Tyr Gly Lys Val Trp Gly Phe Tyr Asp Gly Gln Gln Pro
65                  70                  75                  80

Val Leu Ala Ile Thr Asp Pro Asp Met Ile Lys Thr Val Leu Val Lys
                85                  90                  95

Glu Cys Tyr Ser Val Phe Thr Asn Arg Arg Pro Phe Gly Pro Val Gly
            100                 105                 110

Phe Met Lys Ser Ala Ile Ser Ile Ala Glu Asp Glu Glu Trp Lys Arg
        115                 120                 125

Leu Arg Ser Leu Leu Ser Pro Thr Phe Thr Ser Gly Lys Leu Lys Glu
    130                 135                 140

Met Val Pro Ile Ile Ala Gln Tyr Gly Asp Val Leu Val Arg Asn Leu
145                 150                 155                 160

Arg Arg Glu Ala Glu Thr Gly Lys Pro Val Thr Leu Lys Asp Val Phe
                165                 170                 175
```

```
Gly Ala Tyr Ser Met Asp Val Ile Thr Ser Thr Ser Phe Gly Val Asn
                180                 185                 190

Ile Asp Ser Leu Asn Asn Pro Gln Asp Pro Phe Val Glu Asn Thr Lys
        195                 200                 205

Lys Leu Leu Arg Phe Asp Phe Leu Asp Pro Phe Leu Ser Ile Thr
210                 215                 220

Val Phe Pro Phe Leu Ile Pro Ile Leu Glu Val Leu Asn Ile Cys Val
225                 230                 235                 240

Phe Pro Arg Glu Val Thr Asn Phe Leu Arg Lys Ser Val Lys Arg Met
                245                 250                 255

Lys Glu Ser Arg Leu Glu Asp Thr Gln Lys His Arg Val Asp Phe Leu
                260                 265                 270

Gln Leu Met Ile Asp Ser Gln Asn Ser Lys Glu Thr Glu Ser His Lys
            275                 280                 285

Ala Leu Ser Asp Leu Glu Leu Val Ala Gln Ser Ile Ile Phe Ile Phe
        290                 295                 300

Ala Gly Tyr Glu Thr Thr Ser Ser Val Leu Ser Phe Ile Met Tyr Glu
305                 310                 315                 320

Leu Ala Thr His Pro Asp Val Gln Gln Lys Leu Gln Glu Glu Ile Asp
                325                 330                 335

Ala Val Leu Pro Asn Lys Ala Pro Pro Thr Tyr Asp Thr Val Leu Gln
                340                 345                 350

Met Glu Tyr Leu Asp Met Val Val Asn Glu Thr Leu Arg Leu Phe Pro
            355                 360                 365

Ile Ala Met Arg Leu Glu Arg Val Cys Lys Lys Asp Val Glu Ile Asn
        370                 375                 380

Gly Met Phe Ile Pro Lys Gly Val Val Met Ile Pro Ser Tyr Ala
385                 390                 395                 400

Leu His Arg Asp Pro Lys Tyr Trp Thr Glu Pro Glu Lys Phe Leu Pro
                405                 410                 415

Glu Arg Phe Ser Lys Lys Asn Lys Asp Asn Ile Asp Pro Tyr Ile Tyr
                420                 425                 430

Thr Pro Phe Gly Ser Gly Pro Arg Asn Cys Ile Gly Met Arg Phe Ala
            435                 440                 445

Leu Met Asn Met Lys Leu Ala Leu Ile Arg Val Leu Gln Asn Phe Ser
450                 455                 460

Phe Lys Pro Cys Lys Glu Thr Gln Ile Pro Leu Lys Leu Ser Leu Gly
465                 470                 475                 480

Gly Leu Leu Gln Pro Glu Lys Pro Val Val Leu Lys Val Glu Ser Arg
                485                 490                 495

Asp Gly Thr Val Ser Gly Ala
            500

<210> SEQ ID NO 57
<211> LENGTH: 1835
<212> TYPE: DNA
<213> ORGANISM: Homo sapiens

<400> SEQUENCE: 57
atggattctc ttgtggtcct tgtgctctgt ctctcatgtt tgcttctcct ttcactctgg      60
agacagagct ctgggagagg aaaactccct cctggcccca ctcctctccc agtgattgga     120
aatatcctac agataggtat taaggacatc agcaaatcct taccaatct ctcaaaggtc      180 tatggcccgg tgttcactct gtattttggc ctgaaaccca gtggtgct gcatggatat       240
```

```
gaagcagtga aggaagccct gattgatctt ggagaggagt tttctggaag aggcattttc      300
ccactggctg aaagagctaa cagaggattt ggaattgttt tcagcaatgg aaagaaatgg      360
aaggagatcc ggcgtttctc cctcatgacg ctgcggaatt tgggatggg gaagaggagc       420 attgaggacc gtgttcaaga ggaagcccgc tgccttgtgg aggagttgag aaaaaccaag      480
gcctcaccct gtgatccac tttcatcctg gctgtgctc cctgcaatgt gatctgctcc        540
attattttcc ataaacgttt tgattataaa gatcagcaat tcttaacctt aatgaaaag      600 ttgaatgaaa acatcaagat tttgagcagc ccctggatcc agatctgcaa taattttttct    660 cctatcattg attacttccc gggaactcac aacaaattac ttaaaaacgt tgcttttatg    720
aaaagttata ttttggaaaa agtaaaagaa caccaagaat caatggacat gaacaaccct     780
caggacttta ttgattgctt cctgatgaaa atggagaagg aaaagcacaa ccaaccatct     840
gaatttacta ttgaaagctt ggaaaacact gcagttgact tgtttggagc tgggacagag     900
acgacaagca aaccctgag atatgctctc cttctcctgc tgaagcaccc agaggtcaca      960
gctaaagtcc aggaagagat tgaacgtgtg attggcagaa accggagccc ctgcatgcaa     1020
gacaggagcc acatgcccta cacagatgct gtggtgcacg aggtccagag atacattgac     1080
cttctcccca ccagcctgcc ccatgcagtg acctgtgaca ttaaattcag aaactatctc     1140
attcccaagg gcacaaccat attaatttcc ctgacttctg tgctacatga acaaagaa       1200 tttcccaacc cagagatgtt tgaccctcat cactttctgg atgaaggtgg caatttttaag   1260 aaaagtaaat acttcatgcc tttctcagca ggaaaacgga tttgtgtggg agaagccctg    1320
gccggcatgg agctgttttt attcctgacc tccatttta agaacttta cctgaaatct      1380 ctggttgacc caagaaacct tgacaccact ccagttgtca atggatttgc tctgtgccg     1440 cccttctacc agctgtgctt cattcctgtc tgaagaagag cagatggcct ggctgctgct    1500
gtgcagtccc tgcagctctc tttcctctgg ggcattatcc atctttgcac tatctgtaat   1560
gccttttctc acctgtcatc tcacattttc ccttccctga agatctagtg aacattcgac    1620
ctccattacg gagagtttcc tatgtttcac tgtgcaaata tatctgctat tctccatact   1680
ctgtaacagt tgcattgact gtcacataat gctcatactt atctaatgta gagtattaat   1740
atgttattat taaatagaga aatatgattt gtgtattata attcaaaggc atttctttttc  1800 tgcatgatct aaataaaaag cattattatt tgctg                               1835
```

<210> SEQ ID NO 58
<211> LENGTH: 490
<212> TYPE: PRT
<213> ORGANISM: Homo sapiens

<400> SEQUENCE: 58

```
Met Asp Ser Leu Val Val Leu Val Leu Cys Leu Ser Cys Leu Leu Leu
1               5                   10                  15

Leu Ser Leu Trp Arg Gln Ser Ser Gly Arg Gly Lys Leu Pro Pro Gly
            20                  25                  30

Pro Thr Pro Leu Pro Val Ile Gly Asn Ile Leu Gln Ile Gly Ile Lys
        35                  40                  45

Asp Ile Ser Lys Ser Leu Thr Asn Leu Ser Lys Val Tyr Gly Pro Val
    50                  55                  60

Phe Thr Leu Tyr Phe Gly Leu Lys Pro Ile Val Val Leu His Gly Tyr
65                  70                  75                  80

Glu Ala Val Lys Glu Ala Leu Ile Asp Leu Gly Glu Glu Phe Ser Gly
```

```
                        85                  90                  95
Arg Gly Ile Phe Pro Leu Ala Glu Arg Ala Asn Arg Gly Phe Gly Ile
                100                 105                 110

Val Phe Ser Asn Gly Lys Lys Trp Lys Glu Ile Arg Arg Phe Ser Leu
            115                 120                 125

Met Thr Leu Arg Asn Phe Gly Met Gly Lys Arg Ser Ile Glu Asp Arg
        130                 135                 140

Val Gln Glu Glu Ala Arg Cys Leu Val Glu Glu Leu Arg Lys Thr Lys
145                 150                 155                 160

Ala Ser Pro Cys Asp Pro Thr Phe Ile Leu Gly Cys Ala Pro Cys Asn
                165                 170                 175

Val Ile Cys Ser Ile Ile Phe His Lys Arg Phe Asp Tyr Lys Asp Gln
            180                 185                 190

Gln Phe Leu Asn Leu Met Glu Lys Leu Asn Glu Asn Ile Lys Ile Leu
        195                 200                 205

Ser Ser Pro Trp Ile Gln Ile Cys Asn Asn Phe Ser Pro Ile Ile Asp
210                 215                 220

Tyr Phe Pro Gly Thr His Asn Lys Leu Leu Lys Asn Val Ala Phe Met
225                 230                 235                 240

Lys Ser Tyr Ile Leu Glu Lys Val Lys Glu His Gln Glu Ser Met Asp
                245                 250                 255

Met Asn Asn Pro Gln Asp Phe Ile Asp Cys Phe Leu Met Lys Met Glu
            260                 265                 270

Lys Glu Lys His Asn Gln Pro Ser Glu Phe Thr Ile Glu Ser Leu Glu
        275                 280                 285

Asn Thr Ala Val Asp Leu Phe Gly Ala Gly Thr Glu Thr Thr Ser Thr
    290                 295                 300

Thr Leu Arg Tyr Ala Leu Leu Leu Leu Leu Lys His Pro Glu Val Thr
305                 310                 315                 320

Ala Lys Val Gln Glu Glu Ile Glu Arg Val Ile Gly Arg Asn Arg Ser
                325                 330                 335

Pro Cys Met Gln Asp Arg Ser His Met Pro Tyr Thr Asp Ala Val Val
            340                 345                 350

His Glu Val Gln Arg Tyr Ile Asp Leu Leu Pro Thr Ser Leu Pro His
        355                 360                 365

Ala Val Thr Cys Asp Ile Lys Phe Arg Asn Tyr Leu Ile Pro Lys Gly
    370                 375                 380

Thr Thr Ile Leu Ile Ser Leu Thr Ser Val Leu His Asp Asn Lys Glu
385                 390                 395                 400

Phe Pro Asn Pro Glu Met Phe Asp Pro His His Phe Leu Asp Glu Gly
                405                 410                 415

Gly Asn Phe Lys Lys Ser Lys Tyr Phe Met Pro Phe Ser Ala Gly Lys
            420                 425                 430

Arg Ile Cys Val Gly Glu Ala Leu Ala Gly Met Glu Leu Phe Leu Phe
        435                 440                 445

Leu Thr Ser Ile Leu Gln Asn Phe Asn Leu Lys Ser Leu Val Asp Pro
    450                 455                 460

Lys Asn Leu Asp Thr Thr Pro Val Val Asn Gly Phe Ala Ser Val Pro
465                 470                 475                 480

Pro Phe Tyr Gln Leu Cys Phe Ile Pro Val
                485                 490

<210> SEQ ID NO 59
```

<211> LENGTH: 1494
<212> TYPE: DNA
<213> ORGANISM: Homo sapiens

<400> SEQUENCE: 59

```
atggggctag aagcactggt gcccctggcc gtgatagtgg ccatcttcct gctcctggtg      60
gacctgatgc accggcgcca acgctgggct gcacgctacc caccaggccc cctgccactg     120
cccgggctgg caacctgct gcatgtggac ttccagaaca ccatactg cttcgaccag        180
ttgcggcgcc gcttcgggga cgtgttcagc ctgcagctgg cctggacgcc ggtggtcgtg     240
ctcaatgggc tggcggccgt gcgcgaggcg ctggtgaccc acggcgagga caccgccgac     300
cgcccgcctg tgcccatcac ccagatcctg ggtttcgggc gcgttccca agggggtgttc   360
ctggcgcgct atgggcccgc gtggcgcgag cagaggcgct tctccgtgtc caccttgcgc     420
aacttgggcc tgggcaagaa gtcgctggag cagtgggtga ccgaggaggc cgcctgcctt     480
tgtgccgcct cgccaaccca ctccggacgc cctttcgcc ccaacggtct cttggacaaa      540
gccgtgagca acgtgatcgc ctccctcacc tgcgggcgcc gcttcgagta cgacgaccct     600
cgcttcctca ggctgctgga cctagctcag gagggactga aggaggagtc gggctttctg     660
cgcgaggtgc tgaatgctgt ccccgtcctc ctgcatatcc cagcgctggc tggcaaggtc     720
ctacgcttcc aaaaggcttt cctgacccag ctggatgagc tgctaactga gcacaggatg     780
acctgggacc cagcccagcc ccccgagac ctgactgagg ccttcctggc agagatggag      840
aaggccaagg ggaaccctga gcagcttc aatgatgaga acctgcgcat agtggtggct       900
gacctgttct ctgccgggat ggtgaccacc tcgaccacgc tggcctgggg cctcctgctc     960
atgatcctac atccggatgt gcagcgccgt gtccaacagg agatcgacga cgtgataggg    1020
caggtgcggc gaccagagat gggtgaccag gctcacatgc cctacaccac tgccgtgatt    1080
catgaggtgc agcgctttgg ggacatcgtc ccctgggta tgacccatat gacatccgt      1140
gacatcgaag tacagggctt ccgcatccct aagggaacga cactcatcac caacctgtca   1200
tcggtgctga aggatgaggc cgtctgggag aagcccttcc gcttccaccc gaacactc      1260
ctggatgccc agggccactt tgtgaagccg gaggccttcc tgcctttctc agcaggccgc   1320
cgtgcatgcc tcggggagcc cctggcccgc atggagctct tcctcttctt cacctccctg    1380
ctgcagcact tcagcttctc ggtgccact ggacagcccc ggcccagcca ccatggtgtc      1440
tttgctttcc tggtgagccc atcccctat gagctttgtg ctgtgccccg ctag            1494
```

<210> SEQ ID NO 60
<211> LENGTH: 497
<212> TYPE: PRT
<213> ORGANISM: Homo sapiens

<400> SEQUENCE: 60

```
Met Gly Leu Glu Ala Leu Val Pro Leu Ala Val Ile Val Ala Ile Phe
1               5                   10                  15

Leu Leu Leu Val Asp Leu Met His Arg Arg Gln Arg Trp Ala Ala Arg
            20                  25                  30

Tyr Pro Pro Gly Pro Leu Pro Leu Pro Gly Leu Gly Asn Leu Leu His
        35                  40                  45

Val Asp Phe Gln Asn Thr Pro Tyr Cys Phe Asp Gln Leu Arg Arg Arg
    50                  55                  60

Phe Gly Asp Val Phe Ser Leu Gln Leu Ala Trp Thr Pro Val Val Val
65                  70                  75                  80
```

-continued

```
Leu Asn Gly Leu Ala Ala Val Arg Glu Ala Leu Val Thr His Gly Glu
             85                  90                  95
Asp Thr Ala Asp Arg Pro Val Pro Ile Thr Gln Ile Leu Gly Phe
        100                 105                 110
Gly Pro Arg Ser Gln Gly Val Phe Leu Ala Arg Tyr Gly Pro Ala Trp
        115                 120                 125
Arg Glu Gln Arg Arg Phe Ser Val Ser Thr Leu Arg Asn Leu Gly Leu
        130                 135                 140
Gly Lys Lys Ser Leu Glu Gln Trp Val Thr Glu Ala Ala Cys Leu
145                 150                 155                 160
Cys Ala Ala Phe Ala Asn His Ser Gly Arg Pro Phe Arg Pro Asn Gly
                165                 170                 175
Leu Leu Asp Lys Ala Val Ser Asn Val Ile Ala Ser Leu Thr Cys Gly
            180                 185                 190
Arg Arg Phe Glu Tyr Asp Asp Pro Arg Phe Leu Arg Leu Leu Asp Leu
        195                 200                 205
Ala Gln Glu Gly Leu Lys Glu Glu Ser Gly Phe Leu Arg Glu Val Leu
        210                 215                 220
Asn Ala Val Pro Val Leu Leu His Ile Pro Ala Leu Ala Gly Lys Val
225                 230                 235                 240
Leu Arg Phe Gln Lys Ala Phe Leu Thr Gln Leu Asp Glu Leu Leu Thr
                245                 250                 255
Glu His Arg Met Thr Trp Asp Pro Ala Gln Pro Pro Arg Asp Leu Thr
            260                 265                 270
Glu Ala Phe Leu Ala Glu Met Glu Lys Ala Lys Gly Asn Pro Glu Ser
        275                 280                 285
Ser Phe Asn Asp Glu Asn Leu Arg Ile Val Val Ala Asp Leu Phe Ser
        290                 295                 300
Ala Gly Met Val Thr Thr Ser Thr Thr Leu Ala Trp Gly Leu Leu Leu
305                 310                 315                 320
Met Ile Leu His Pro Asp Val Gln Arg Arg Val Gln Gln Glu Ile Asp
                325                 330                 335
Asp Val Ile Gly Gln Val Arg Arg Pro Glu Met Gly Asp Gln Ala His
            340                 345                 350
Met Pro Tyr Thr Thr Ala Val Ile His Glu Val Gln Arg Phe Gly Asp
        355                 360                 365
Ile Val Pro Leu Gly Met Thr His Met Thr Ser Arg Asp Ile Glu Val
        370                 375                 380
Gln Gly Phe Arg Ile Pro Lys Gly Thr Thr Leu Ile Thr Asn Leu Ser
385                 390                 395                 400
Ser Val Leu Lys Asp Glu Ala Val Trp Glu Lys Pro Phe Arg Phe His
                405                 410                 415
Pro Glu His Phe Leu Asp Ala Gln Gly His Phe Val Lys Pro Glu Ala
            420                 425                 430
Phe Leu Pro Phe Ser Ala Gly Arg Arg Ala Cys Leu Gly Glu Pro Leu
        435                 440                 445
Ala Arg Met Glu Leu Phe Leu Phe Phe Thr Ser Leu Leu Gln His Phe
        450                 455                 460
Ser Phe Ser Val Pro Thr Gly Gln Pro Arg Pro Ser His His Gly Val
465                 470                 475                 480
Phe Ala Phe Leu Val Ser Pro Ser Pro Tyr Glu Leu Cys Ala Val Pro
                485                 490                 495
Arg
```

<210> SEQ ID NO 61
<211> LENGTH: 44
<212> TYPE: PRT
<213> ORGANISM: Homo sapiens

<400> SEQUENCE: 61

Arg Arg Ala Asp Gly Leu Ala Ala Ala Val Gln Ser Leu Gln Leu Ser
1               5                   10                  15

Phe Leu Trp Gly Ile Ile His Leu Cys Thr Ile Cys Asn Ala Phe Ser
            20                  25                  30

His Leu Ser Ser His Ile Phe Pro Ser Leu Lys Ile
        35                  40

<210> SEQ ID NO 62
<211> LENGTH: 24
<212> TYPE: PRT
<213> ORGANISM: Homo sapiens

<400> SEQUENCE: 62

Thr Phe Asp Leu His Tyr Gly Glu Phe Pro Met Phe His Cys Ala Asn
1               5                   10                  15

Ile Ser Ala Ile Leu His Thr Leu
            20

<210> SEQ ID NO 63
<211> LENGTH: 10
<212> TYPE: PRT
<213> ORGANISM: Homo sapiens

<400> SEQUENCE: 63

Leu Ser His Asn Ala His Thr Tyr Leu Met
1               5                   10

<210> SEQ ID NO 64
<211> LENGTH: 11
<212> TYPE: PRT
<213> ORGANISM: Homo sapiens

<400> SEQUENCE: 64

Ser Ile Asn Met Leu Leu Leu Asn Arg Glu Ile
1               5                   10

<210> SEQ ID NO 65
<211> LENGTH: 14
<212> TYPE: PRT
<213> ORGANISM: Homo sapiens

<400> SEQUENCE: 65

Phe Val Tyr Tyr Asn Ser Lys Ala Phe Leu Phe Cys Met Ile
1               5                   10

<210> SEQ ID NO 66
<211> LENGTH: 7
<212> TYPE: PRT
<213> ORGANISM: Homo sapiens

<400> SEQUENCE: 66

Ile Lys Ser Ile Ile Ile Cys
1               5

ARRAYS

REFERENCE TO RELATED APPLICATIONS

This application claims the benefit of U.S. provisional patent application No. 60/335,806, filed Dec. 5, 2001, and of U.S. provisional patent application No. 60/410,815, filed Sep. 16, 2002, the complete disclosures of each of which are herein incorporated by reference.

BACKGROUND OF THE INVENTION

Single nucleotide polymorphisms (SNPs) are single base differences between the DNA of organisms. They underlie much of the genetic component of phenotypic variation between individuals with the exception of identical siblings and clones. Since this variation includes characteristics such as predisposition to disease, age of onset, severity of disease and response to treatment, the identification and cataloguing of SNPs will lead to 'genetic medicine' [Chakravarti, A. *Nature* 409 822-823 (2001)]. Disciplines such as pharmacogenomics are aiming to establish correlations between SNPs and response to drug treatment in order to tailor therapeutic programmes to the individual person. More broadly, the role of particular SNPs in conditions such as sickle cell anaemia and Alzheimer's disease, and issues such as HIV resistance and transplant rejection, are well appreciated. However, correlations between SNPs and their phenotypes are usually derived from statistical analyses of population data and little attempt is made to elucidate the molecular mechanism of the observed phenotypic variation. Until the advent of high-throughput sequencing projects aimed at determining the complete sequence of the human genome [The International Human Genome Mapping Consortium *Nature* 409 860-921 (2001); Venter, J. C. *Science* 291 1304-1351 (2001)], only a few thousand SNPs had been identified. More recently 1.42 million SNPs were catalogued by a consortium of researchers in a paper accompanying the human sequence [The International SNP Map Working Group *Nature* 409 928-933 (2001)] of which 60,000 were present within genes ('coding' SNPs). Coding SNPs can be further classified according to whether or not they alter the amino acid sequence of the protein and where changes do occur, protein function may be affected resulting in phenotypic variation. Thus there is an unmet need for apparatus and methodology capable of rapidly determining the phenotypes of this large volume of variant sequences.

SUMMARY OF THE INVENTION

The Inventors herein describe protein arrays and their use to assay, in a parallel fashion, the protein products of highly homologous or related DNA coding sequences.

By highly homologous or related it is meant those DNA coding sequences which share a common sequence and which differ only by one or more naturally occurring mutations such as single nucleotide polymorphisms, deletions or insertions, or those sequences which are considered to be haplotypes (a haplotype being a combination of variations or mutations on a chromosome, usually within the context of a particular gene). Such highly homologous or related DNA coding sequences are generally naturally occurring variants of the same gene.

Arrays according to the invention have multiple (for example, two or more), individual proteins deposited in a spatially defined pattern on a surface in a form whereby the properties, (for example, the activity or function of the proteins) can be investigated or assayed in parallel by interrogation of the array.

Protein arrays according to the invention and their use to assay the phenotypic changes in protein function resulting from mutations (for example, coding SNPs—i.e. those SNP mutations that still give rise to an expressed protein) differ completely from, and have advantages over, existing DNA based technologies for SNP and other mutational analyses [reviewed in Shi, M. M *Clin Chem* 47 164-72 (2001)]. These latter technologies include high-throughput sequencing and electrophoretic methods for identifying new SNPs, or diagnostic technologies such as high density oligonucleotide arrays [e.g. Lindblad-Toh, K. *Nat Genet* 24 381-6 (2000)] or high-throughput, short-read sequencing techniques which permit profiling of an individual's gene of interest against known SNPs [e.g. Buetow, K. H. *Proc Natl Acad Sci USA* 98 581-4 (2001)]. Importantly, and in contrast to the invention described herein, the phenotypic effects of a polymorphism remain unknown when only analysed at the DNA level.

Indeed, the effects of coding SNPs on the proteins they encode are, with relatively few exceptions, uncharacterised. Examples of proteins with many catalogued SNPs but little functional data on the effect of these SNPs include p53, p10 (both cancer related) and the cytochrome P450s (drug metabolism). There are currently few if any methods capable of investigating the functionalities of SNP-encoded proteins with sufficiently high throughput required to handle the large volume of SNP data being generated. Bioinformatics or computer modelling is possible, especially if a crystal structure is available, but the hypotheses generated still need to be verified experimentally (i.e. through biochemical assay). Frequently though, the role of the mutation remains unclear after bioinformatic or computer-based analysis. Therefore, protein arrays as provided by the invention offer the most powerful route to functional analysis of SNPs.

It would be possible to individually assay proteins derived from related DNA molecules, for example differing by one or more single nucleotide polymorphisms, in a test tube format, however the serial nature of this work and the large sample volumes involved make this approach cumbersome and unattractive. By arraying out the related proteins in a microtiter plate or on a microscope slide, many different proteins (hundreds or thousands) can be assayed simultaneously using only small sample volumes (few microlitres only in the case of microarrays) thus making functional analysis of, for example, SNPs economically feasible. All proteins can be assayed together in the same experiment which reduces sources of error due to differential handling of materials. Additionally, tethering the proteins directly to a solid support facilitates binding assays which require unbound ligands to be washed away prior to measuring bound concentrations, a feature not available in solution based or single phase liquid assays.

Specific advantages over apparatus and methods currently known in the art provided by the arrays of the present invention are:
- massively parallel analysis of closely related proteins, for example those derived from coding SNPs, for encoded function
- sensitivity of analysis at least comparable to existing methods, if not better
- enables quantitative, comparative functional analysis in a manner not previously possible compatible with protein: protein, protein: nucleic acid, protein: ligand, or protein: small molecule interactions and post-translational modifications in situ "on-chip"

parallel protein arrays according to the invention are spotting density independent microarray format enables analysis to be carried out using small volumes of potentially expensive ligands information provided by parallel protein arrays according to the invention will be extremely valuable for drug discovery, pharmacogenomics and diagnostics fields other useful parallel protein arrays may include proteins derived from non-natural (synthetic) mutations of a DNA sequence of interest. Such arrays can be used to investigate interactions between the variant protein thus produced and other proteins, nucleic acid molecules and other molecules, for example ligands or candidate/test small molecules. Suitable methods of carrying out such mutagenesis are described in Current Protocols in Molecular Biology, Volume 1, Chapter 8, Edited by Ausubel, F M, Brent, R, Kingston, R E, Moore, D D, Siedman, J G, Smith, J A, and Struhl, K.

Thus in one aspect, the invention provides a protein array comprising a surface upon which are deposited at spatially defined locations at least two protein moieties characterised in that said protein moieties are those of naturally occurring variants of a DNA sequence of interest.

A protein array as defined herein is a spatially defined arrangement of protein moieties in a pattern on a surface. Preferably the protein moieties are attached to the surface either directly or indirectly. The attachment can be non-specific (e.g. by physical absorption onto the surface or by formation of a non-specific covalent interaction). In a preferred embodiment the protein moieties are attached to the surface through a common marker moiety appended to each protein moiety. In another preferred embodiment, the protein moieties can be incorporated into a vesicle or liposome which is tethered to the surface.

A surface as defined herein is a flat or contoured area that may or may not be coated/derivatised by chemical treatment. For example, the area can be:

a glass slide, one or more beads, for example a magnetised, derivatised and/or labelled bead as known in the art, a polypropylene or polystyrene slide, a polypropylene or polystyrene multi-well plate, a gold, silica or metal object, a membrane made of nitrocellulose, PVDF, nylon or phosphocellulose Where a bead is used, individual proteins, pairs of proteins or pools of variant proteins (e.g., for "shotgun screening"- to initially identify groups of proteins in which a protein of interest may exist; such groups are then separated and further investigated (analogous to pooling methods known in the art of combinatorial chemistry)) may be attached to an individual bead to provide the spatial definition or separation of the array. The beads may then be assayed separately, but in parallel, in a compartmentalised way, for example in the wells of a microtitre plate or in separate test tubes.

Thus a protein array comprising a surface according to the invention may subsist as series of separate solid phase surfaces, such as beads carrying different proteins, the array being formed by the spatially defined pattern or arrangement of the separate surfaces in the experiment.

Preferably the surface coating is capable of resisting non-specific protein absorption. The surface coating can be porous or non-porous in nature. In addition, in a preferred embodiment the surface coating provides a specific interaction with the marker moiety on each protein moiety either directly or indirectly (e.g. through a protein or peptide or nucleic acid bound to the surface). An embodiment of the invention described in the examples below uses SAM2™ membrane (Promega, Madison, Wis., USA) as the capture surface, although a variety of other surfaces can be used, as well as surfaces in microarray or microwell formats as known in the art.

A protein moiety is a protein or a polypeptide encoded by a DNA sequence which is generally a gene or a naturally occurring variant of the gene. The protein moiety may take the form of the encoded protein, or may comprise additional amino acids (not originally encoded by the DNA sequence from which it is derived) to facilitate attachment to the array or analysis in an assay. In the case of the protein having only the amino acid sequence encoded by the naturally occurring gene, without additional sequence, such proteins may be attached to the array by way of a common feature between the variants. For example, a set of variant proteins may be attached to the array via a binding protein or an antibody which is capable of binding an invariant or common part of the individual proteins in the set. Preferably, protein moieties according to the invention are proteins tagged (via the combination of the protein encoding DNA sequence with a tag encoding DNA sequence) at either the N- or C-terminus with a marker moiety to facilitate attachment to the array.

Each position in the pattern of an array can contain, for example, either:

a sample of a single protein type (in the form of a monomer, dimer, trimer, tetramer or higher multimer) or a sample of a single protein type bound to an interacting molecule (for example, nucleic acid molecule, antibody, other protein or small molecule. The interacting molecule may itself interact with further molecules. For example, one subunit of an heteromeric protein may be attached to the array and a second subunit or complex of subunits may be tethered to the array via interaction with the attached protein subunit. In turn the second subunit or complex of subunits may then interact with a further molecule, e.g. a candidate drug or an antibody) or a sample of a single protein type bound to a synthetic molecule (e.g. peptide, chemical compound) or a sample of two different variant proteins or "haplotype proteins", for example each possessing a different complement of mutations or polymorphisms, e.g. "protein 1" is derived from a DNA sequence carrying SNP "A" and a 3 base pair deletion "X" whilst "protein 2" is derived from a DNA sequence carrying SNP "A", SNP "B" and a 3 base pair insertion "Y". Such an arrangement is capable of mimicking the heterozygous presence of two different protein variants in an individual.

Preferably the protein moiety at each position is substantially pure but in certain circumstances mixtures of between 2 and 100 different protein moieties can be present at each position in the pattern of an array of which at least one is tagged. Thus the proteins derived from the expression of more than one variant DNA sequence may be attached a single position for example, for the purposes of initial bulk screening of a set of variants to determine those sets containing variants of interest.

An embodiment of the invention described in the examples below uses a biotin tag to purify the proteins on the surface, however, the functionality of the array is independent of tag used.

"Naturally occurring variants of a DNA sequence of interest" are defined herein as being protein-encoding DNA sequences which share a common sequence and which differ only by one or more naturally occurring (i.e. present in a population and not introduced artificially) single nucleotide polymorphisms, deletions or insertions or those sequences which are considered to be haplotypes (a haplotype being a combination of variant features on a chromosome, usually within the context of a particular gene). Generally such DNA sequences are derived from the same gene in that they map to a common chromosomal locus and encode similar proteins, which may possess different phenotypes. In other words, such variants are generally naturally occurring versions of the same gene comprising one or more mutations, or their synthetic equivalents, which whilst having different codons, encode the same "wild-type" or variant proteins as those know to occur in a population.

Usefully, DNA molecules having all known mutations in a population are used to produce a set of protein moieties which are attached to the arrays of the invention. Optionally, the array may comprise a subset of variant proteins derived from DNA molecules possessing a subset of mutations, for example all known germ-line, or inheritable mutations or a subset of clinically relevant or clinically important mutations. Related DNA molecules as defined herein are related by more than just a common tag sequence introduced for the purposes or marking the resulting expressed protein. It is the sequence additional to such tags which is relevant to the relatedness of the DNA molecules. The related sequences are generally the natural coding sequence of a gene and variant forms caused by mutation. In practice the arrays of the invention carry protein moieties which are derived from DNA molecules which differ, i.e. are mutated at 1 to 10, 1 to 7, 1 to 5, 1 to 4, 1 to 3, 1 to 2 or 1 discrete locations in the sequence of one DNA molecule relative to another, or more often relative to the wild-type coding sequence (or most common variant in a population). The difference or mutation at each discrete sequence location (for example a discrete location such as "base-pair 342" (the location can be a single base) or "base-pair 502 to base-pair 525" (the location can be a region of bases)) may be a point mutation such as a base change, for example the substitution of "A" for "G". This may lead to a "mis-sense" mutation, where one amino acid in the wild type sequence is replaced by different amino acid. A "single nucleotide polymorphism" is a mutation of a single nucleotide. Alternatively the mutation may be a deletion or insertion of 1 to 200, 1 to 100, 1 to 50, 1 to 20 or 1 to 10 bases. To give an example, insertional mutations are found in "triplet repeat" disorders such as Huntington's Disease-protein variants corresponding to such insertional mutations can be derived from various mutant forms of the gene and attached to the array to permit investigation of their phenotypes.

Thus, it is envisaged that proteins derived from related DNA molecules can be quite different in structure. For example a related DNA molecule which has undergone a mutation which truncates it, introduces a frame-shift or introduces a stop codon part-way through the wild-type coding sequence may produce a smaller or shorter protein product. Likewise mutation may cause the variant protein to have additional structure, for example a repeated domain or a number of additional amino acids either at the termini of the protein or within the sequence of the protein. Such proteins, being derived from related DNA sequences, are included within the scope of the invention.

As stated above, also included within the scope of the invention are arrays carrying protein moieties encoded by synthetic equivalents of a wild type gene (or a naturally occurring variant thereof) of a DNA sequence of interest.

Also included within the scope of the invention are arrays carrying protein moieties derived from related DNA molecules which, having variant i.e. mutated sequences, give rise to products which undergo differential pre-translational processing (e.g., alternatively spliced transcripts) or differential post-translational processing (e.g. glycosylation occurs at a particular amino acid in one expressed protein, but does not occur in another expressed protein due a codon change in the underlying DNA sequence causing the glycosylated amino acid to be absent).

Generally, related DNA molecules according to the invention are derived from genes which map to the same chromosomal locus, i.e. the related DNA molecules are different versions of the same protein coding sequence derived from a single copy of a gene, which differ as a result of natural mutation.

The wild-type (or the protein encoded by the most common variant DNA sequence in a population) of the protein is preferably included as one of the protein moieties on the array to act as a reference by which the relative activities of the proteins derived from related DNA molecules can be compared. The output of the assay indicates whether the related DNA molecule comprising a mutated gene encodes:

(1) a protein with comparable function to the wild-type protein
(2) a protein with lower or higher levels of function than the wild-type
(3) a protein with no detectable function
(4) a protein with altered post-translational modification patterns
(5) a protein with an activity that can be modified by addition of an extra component (e.g. peptide, antibody or small molecule drug candidate).
(6) a protein with an activity that can be modified by post-translational modification for example in situ on the chip, for example phosphorylation.
(7) a protein with an altered function under different environmental conditions in the assay, for example ionic strength, temperature or pH.

The protein moieties of the arrays of the present invention can comprise proteins associated with a disease state, drug metabolism, or may be uncharacterised. In one preferred embodiment the protein moieties encode wild type p53 and allelic variants thereof. In another preferred embodiment the arrays comprises protein moieties which encode a drug metabolising enzyme, preferably wild type p450 and allelic variants thereof.

The number of protein variants attached to the arrays of the invention will be determined by the number of variant coding sequences that occur naturally or that are of sufficient experimental, commercial or clinical interest to generate artificially. An array carrying a wild type protein and a single variant would be of use to the investigator. However in practice and in order to take advantage of the suitability of such arrays for high throughput assays, it is envisaged that 1 to 10000, 1 to 1000, 1 to 500, 1 to 400, 1 to 300, 1 to 200, 1 to 100, 1 to 75, 1 to 50, 1 to 25, 1 to 10 or 1 to 5 related DNA molecules are represented by their encoded proteins on an array. For example, in the case of the gene for p53 (the subject of one of the Examples described herein) there are currently about 50 known germ-line or inheritable mutations and more than 1000 known somatic mutations. An individual may of course inherit two different germ-line mutations. Thus a p53 variant protein array might carry proteins derived from the 50 germ-line mutations each isolated at a different location, proteins from a clinically relevant subset of 800 somatic coding mutations (where a protein can be expressed) each isolated at a different location (or in groups of 10 at each location) and all possible pair-wise combinations of the 50 germ-line mutations each located at a different location. It can therefore be seen that an array of the invention can usefully represent individual DNA molecules containing more than 1000 different naturally occurring mutations and can accordingly carry many more, for example 10000 or more, separate discrete samples or "spots" of the protein variants derived therefrom either located alone or in combination with other variants.

In a second aspect, the invention provides a method of making a protein array comprising the steps of
a) providing DNA coding sequences which are derived from two or more naturally occurring variants of a DNA sequence of interest
b) expressing said coding sequences to provide one or more individual proteins
c) purifying said proteins
d) depositing said proteins at spatially defined locations on a surface to give an array.

Steps c) and d) are preferably combined in a single step. This can be done by means of "surface capture" by which is meant the simultaneous purification and isolation of the protein moiety on the array via the incorporated tag as described in the examples below. Furthermore, step c) may be optional as it is not necessary for the protein preparation to be pure at the location of the isolated tagged protein—the tagged protein need not be separated from the crude lysate of the host production cell if purity is not demanded by the assay in which the array takes part.

The DNA molecules which are expressed to produce the protein moieties of the array can be generated using techniques known in the art (for example see Current Protocols in Molecular Biology, Volume 1, Chapter 8, Edited by Ausubel, F M, Brent, R, Kingston, R E, Moore, D D, Siedman, J G, Smith, J A, and Struhl, K). The ease of in vitro manipulation of cloned DNA enables mutations, for example SNPs, to be generated by standard molecular biological techniques such as PCR mutagenesis using the wild-type gene as a template. Therefore, only knowledge of the identity of the mutation, for example SNP (often available in electronic databases), and not the actual mutation containing DNA molecule, is required for protein array fabrication. The wild-type gene, encoding the protein of interest, is first cloned into a DNA vector for expression in a suitable host. It will be understood by those skilled in the art that the expression host need not be limited to E. coli—yeast, insect or mammalian cells can be used. Use of a eukaryotic host may be desirable where the protein under investigation is known to undergo post-translational modification such as glycosylation. Following confirmation of expression and protein activity, the wild-type gene is mutated to introduce the desired SNPs. The presence of the SNP is confirmed by sequencing following re-cloning.

To make the array, clones can be grown in microtiter plate format (but not exclusively) allowing parallel processing of samples in a format that is convenient for arraying onto slides or plate formats and which provides a high-throughput format. Protein expression is induced and clones are subsequently processed for arraying. This can involve purification of the proteins by affinity chromatography, or preparation of lysates ready for arraying onto a surface which is selective for the recombinant protein ('surface capture'). Thus, the DNA molecules may be expressed as fusion proteins to give protein moieties tagged at either the N- or C-terminus with a marker moiety. As described herein, such tags may be used to purify or attach the proteins to the surface or the array. Conveniently and preferably, the protein moieties are simultaneously purified from the expression host lysate and attached to the array by means of the marker moiety. The resulting array of proteins can then be used to assay the functions of all proteins in a parallel, and therefore high-throughput manner.

In a third aspect, the invention provides a method of simultaneously determining the relative properties of members of a set of protein moieties derived from related DNA molecules, comprising the steps of: providing an array as herein described, bringing said array into contact with a test substance, and observing the interaction of the test substance with each set member on the array.

In one embodiment, the invention provides a method of screening a set of protein moieties derived from related DNA molecules for compounds (for example, a small organic molecule) which restore or disrupt function of a protein, which may reveal compounds with therapeutic advantages or disadvantages for a subset of the population carrying a particular SNP or other mutation. In other embodiments the test substance may be:
a protein for determining relative protein:protein interactions within a set of protein moieties derived from related DNA molecules
a nucleic acid molecule for determining relative protein: DNA or protein:RNA interactions
a ligand for determining relative protein:ligand interactions Results obtained from the interrogation of arrays of the invention can be quantitative (e.g. measuring binding or catalytic constants $K_D$ & $K_M$), semi-quantitative (e.g. normalising amount bound against protein quantity) or qualitative (e.g. functional vs. non-functional). By quantifying the signals for replicate arrays where the ligand is added at several (for example, two or more) concentrations, both the binding affinities and the active concentrations of protein in the spot can be determined. This allows comparison of SNPs with each other and the wild-type. This level of information has not been obtained previously from arrays. Exactly the same methodology could be used to measure binding of drugs to arrayed proteins.

For example, quantitative results, $K_D$ and $B_{max}$, which describe the affinity of the interaction between ligand and protein and the number of binding sites for that ligand respectively, can be derived from protein array data. Briefly, either quantified or relative amounts of ligand bound to each individual protein spot can be measured at different concentrations of ligand in the assay solution. Assuming a linear relationship between the amount of protein and bound ligand, the (relative) amount of ligand bound to each spot over a range of ligand concentrations used in the assay can be fitted to equation 1, rearrangements or derivations.

$$\text{Bound ligand} = B_{max}/((K_D/[L])+1) \qquad \text{(Equation 1)}$$

[L]=concentration of ligand used in the assay

Preferred features of each aspect of the invention are as defined for each other aspect, mutatis mutandis.

Further features and details of the invention will be apparent from the following description of specific embodiments of a protein array, a p53 protein SNP array and a p450 array, and its use in accordance with the invention which is given by way of example with reference to the accompanying drawings, in which:

BRIEF DESCRIPTION OF THE DRAWINGS

FIG. 9B shows the DNA sequence of pBJW102.2 (SEQ ID NO:52).

FIG. 9C shows the cloning site of pBJW102.2 from start codon (SEQ ID NO:53). Human P450s, NADPH-cytochrome P450 reductase, and cytochrome b5 ORFs, and truncations thereof, were ligated to a DraIII/SmaI digested vector of pBJWI02.2.

FIG. 10B shows the sequence of the vector pJW45 (SEQ ID NO:54).

FIG. 11A shows the DNA sequence of Human P450 3A4 open reading frame (SEQ ID NO:55).

FIG. 11B shows the amino acid sequence of full length human P450 frame 3A4 (SEQ ID NO:56).

FIG. 12A shows the DNA sequence of human P450 2C9 open reading frame (SEQ ID NO:57).

FIG. 12B shows the amino acid sequence of full length human P450 2C9 (SEQ ID NO:58).

FIG. 13A shows the DNA sequence of human P450 2D6 open reading frame (SEQ ID NO:59).

FIG. 13B shows the amino acid sequence of full length human P450 2D6 (SEQ ID NO:60).

Lanes 1: Whole cells
Lanes 2: Lysate
Lanes 3: Lysed E. coli cells
Lanes 4: Supernatant from E. coli cell wash
Lanes 5: Pellet from E. coli cell wash
Lanes 6: Supernatant after membrane sublublisation
Lanes 7: pellet after membrane sublublisation
Lanes 8: molecular weight markers: 175, 83, 62, 48, 32, 25, 16.5, 6.5 Kda.

Figure 15:
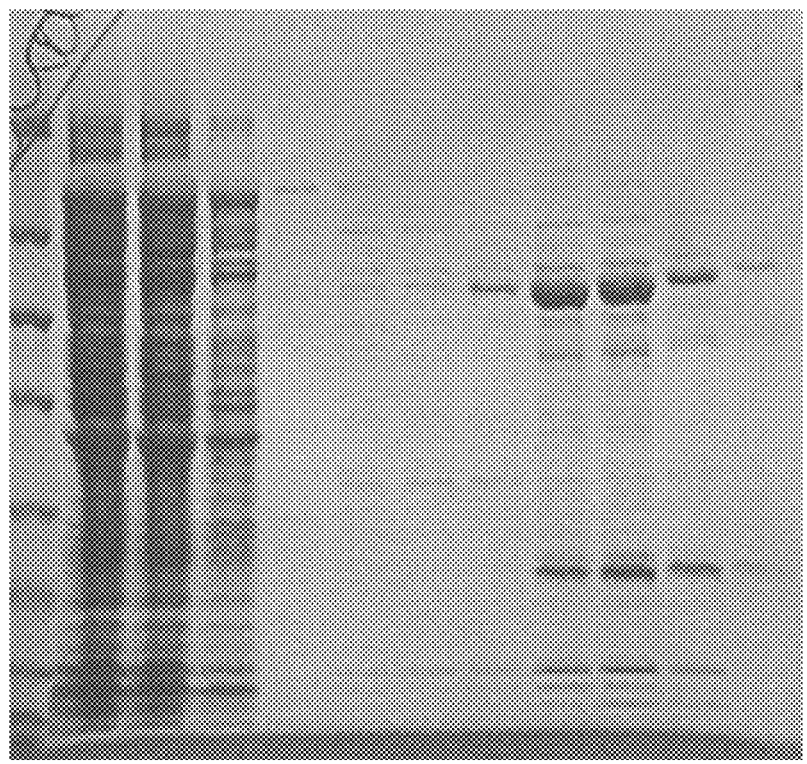

FIG. 15 shows the Coomassie stained gel of Ni-NTA column purification of cytochrome P450 3A4. Samples from all stages of column purification were run on SDS-PAGE:
Lane 1: Markers 175, 83, 62, 48, 32, 25, 16.5, 6.5 KDa
Lane 2: Supernatant from membrane sublublisation
Lane 3: Column Flow-Through
Lane 4: Wash in buffer C
Lane 5: Wash in buffer D
Lanes 6&7: Washes in buffer D+50 mM Imidazole
Lanes 8-12: Elution in buffer D+200 mM Imidazole.

Figure 16:
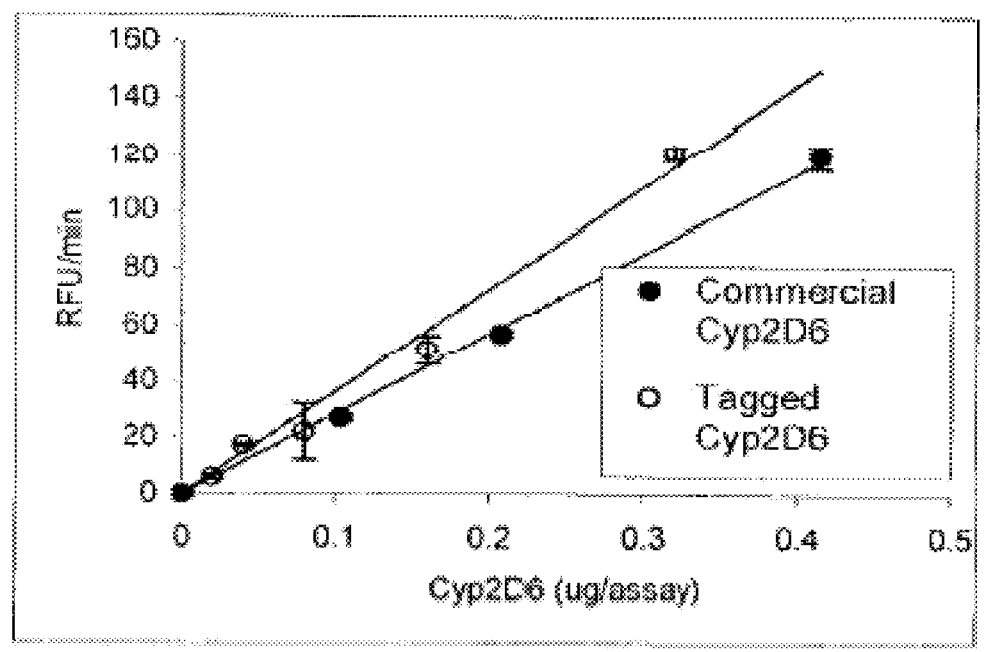

FIG. 16 shows the assay of activity for cytochrome P450 2D6 in a reconstitution assay using the substrate AMMC. Recombinant, tagged CYP2D6 was compared with a commercially available CYP2D6 in terms of ability to turnover AMMC after reconstitution in liposomes with NADPH-cytochrome P450 reductase.

Figure 17:
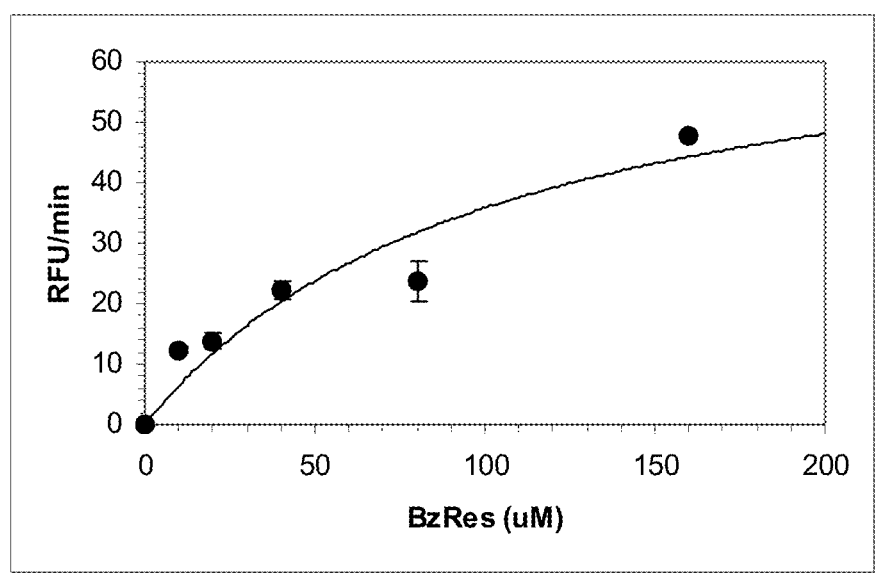

FIG. 17 shows the rates of resorufin formation from BzRes by cumene hydrogen peroxide activated cytochrome P450 3A4. Cytochrome P450 3A4 was assayed in solution with cumene hydrogen peroxide activation in the presence of increasing concentrations of BzRes up to 160 J.lM.

Figure 18:
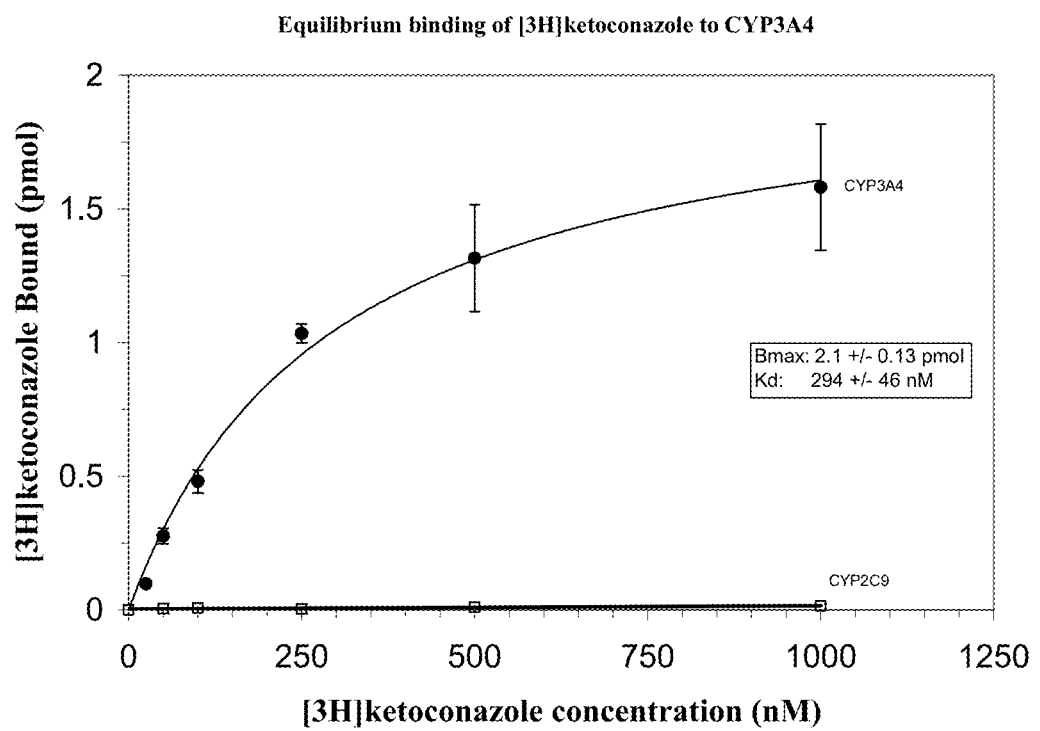

FIG. 18 shows the equilibrium binding of [$^3$H]ketoconazole to immobilised CYP3A4 and CYP2C9. In the case of CYP3A4 the data points are the means±standard deviation, of 4 experiments. Non-specific binding was determined in the presence of 100 µM ketoconazole (data not shown).

Figure 19:
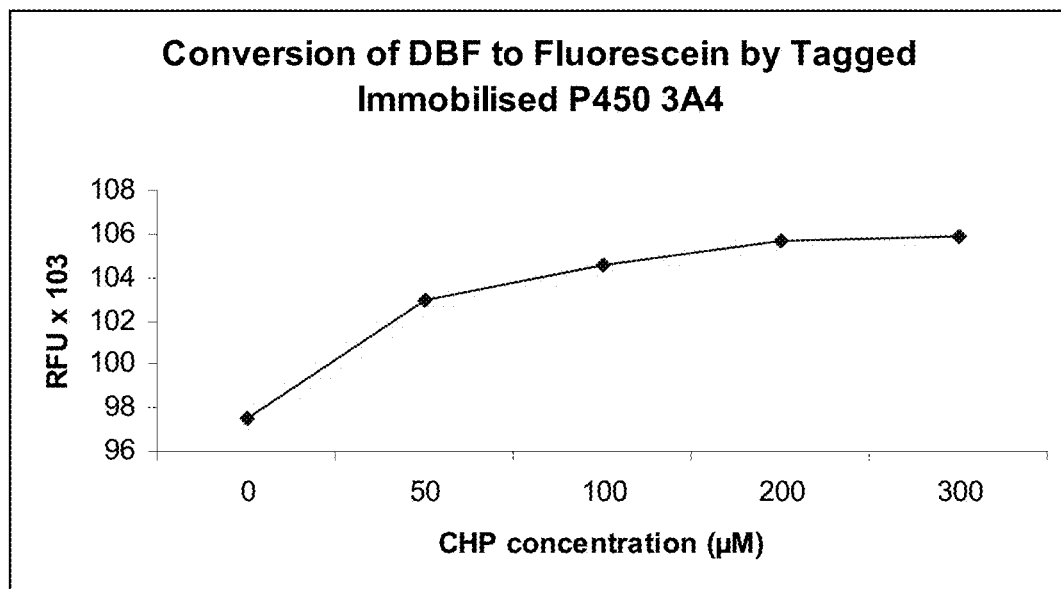

FIG. 19 shows the chemical activation of tagged, immobilised P450 involving conversion of DBF to fluorescein by CHP activated P450 3A4 immobilised on a streptavidin surface.

Figure 20:
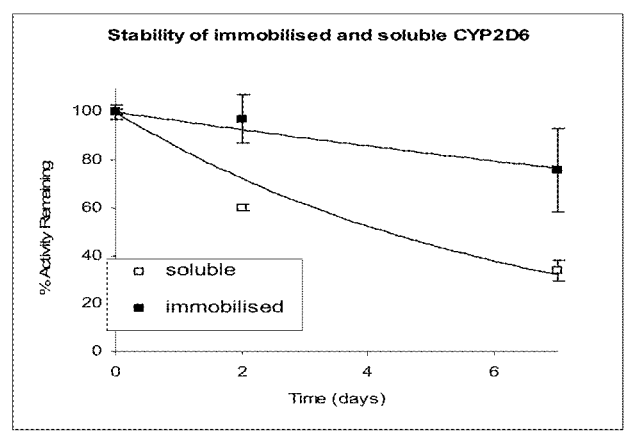

FIG. 20 shows the stability of agarose encapsulated microsomes. Microsomes containing cytochrome P450 2D6 plus NADPH-cytochrome P450 reductase and cytochrome b5 were diluted in agarose and allowed to set in 96 well plates. AMMC turnover was measured immediately and after two and seven days at 4° C.

Figure 21:
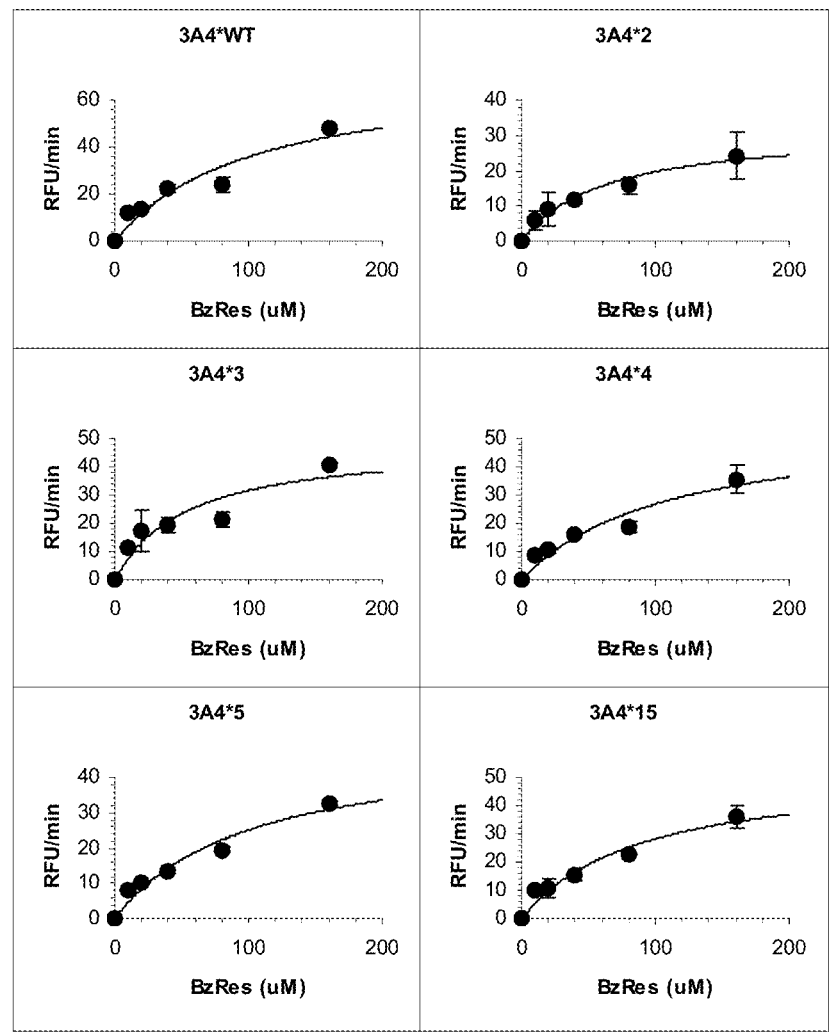

FIG. 21 shows the turnover of BzRes by cytochrome P450 3A4 isofonns. Cytochrome P450 3A4 isofonns WT, *1, *2, *3, *4, *5 & *15, (approximately 1 µg) were incubated in the presence of BzRes (0-160 µM) and cumene hydrogen peroxide (200 µM) at room temperature in 200 mM KP04 buffer pH 7.4. Formation of resorufin was measured over time and rates were calculated from progress curves. Curves describing conventional Michaelis-Menton kinetics were fitted to the data.

Figure 22:
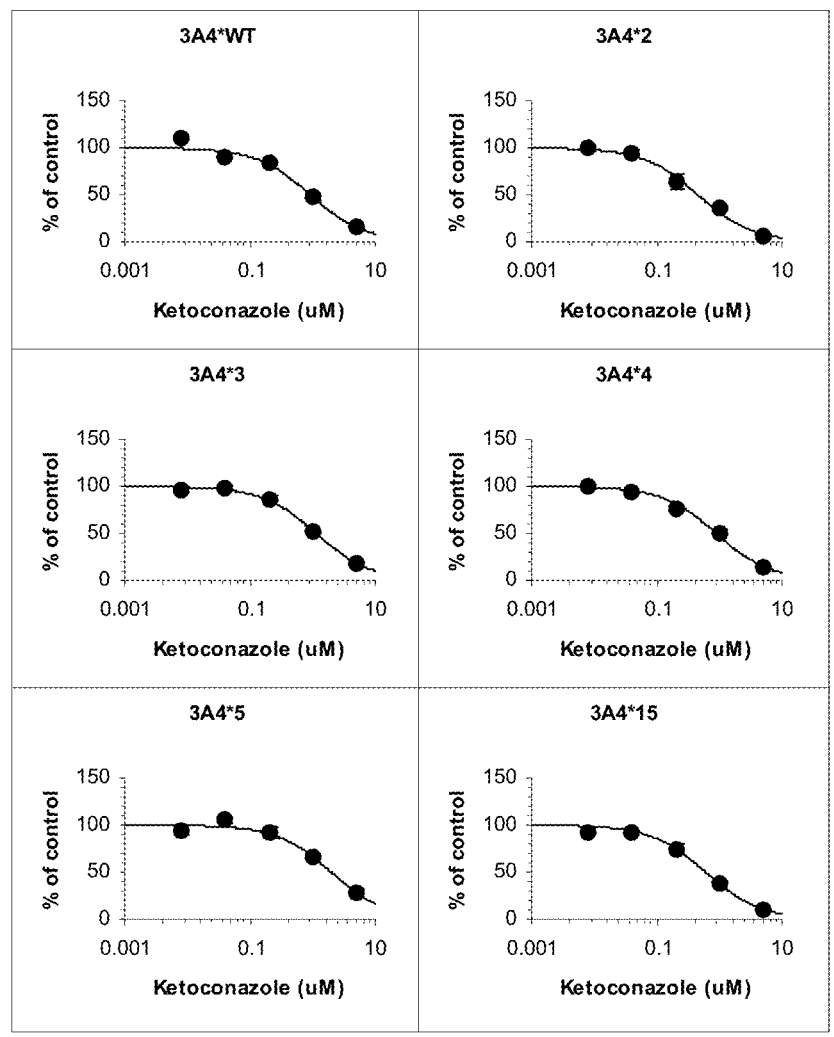

FIG. 22 shows the inhibition of cytochrome P450 3A4 isofonns by ketoconazole. Cytochrome P450 3A4 isofonns WT, *1, *2, *3, *4, *5 & *15, (approximately 1 µg) were incubated in the presence of BzRes (50 µM), Cumene hydrogen peroxide (200 µM) and ketoconazole (0, 0.008, 0.04, 0.2, 1, 5 µM) at room temperature in 200 mM KP04 buffer pH 7.4. Formation of resorufin was measured over time and rates were calculated from progress curves. ICso inhibition curves were fitted to the data.

EXAMPLES

Example I: Use of a Protein Array for Functional Analysis of Proteins Encoded by SNP-Containing Genes—the p53 Protein SNP Array Mutations in the tumour suppresser protein p53 have been associated with around 50% of cancers, and more than a thousand SNPs of this gene have been observed. Mutations of the p53 gene in tumour cells (somatic mutation), or in the genome of families with a predisposition to cancer (germline mutation), provide an association between a condition and genotype, but no molecular mechanism. To demonstrate the utility of protein arrays for functional characterisation of coding SNPs, the Inventors have arrayed wild type human p53 together with 46 germline mutations (SNPs). The biochemical activity of these proteins can then be compared rapidly and in parallel using small sample volumes of reagent or ligand. The arrayed proteins are shown to be functional for DNA binding, phosphorylated post-translationally "on-chip" by a known p53 kinase, and can interact with a known p53-interacting protein, MDM2. For many of these SNPs, this is the first functional characterisation of the effect of the mutation on p53 function, and illustrates the usefulness of protein microarrays in analysing biochemical activities in a massively parallel fashion.

Materials and Methods for Construction of p53 SNP Array.

Wild type p53 cDNA was amplified by PCR from a HeLa cell cDNA library using primers P53F (5' atg gag gag ccg cag tea gat cct ag 3'; SEQ ID NO: 1) and P53R (5' gat cgc ggc cgc tea gtc agg ccc ttc tg 3'; SEQ ID NO:2) and ligated into an E. coli expression vector downstream of sequence coding for a poly Histidine-tag and the BCCP domain from the E. coli AeeB gene. The ligation mix was transformed into chemically competent XLIBlue cells (Stratagene) according to the manufacturer's instructions. The p53 cDNA sequence was checked by sequencing and found to correspond to wild type p53 protein sequence as contained in the SWISS-PROT entry for p53 [Accession No. P04637].

Construction of p53 Mutant Panel

Mutants of p53 were made by using the plasmid containing the wild type p53 sequence as template in an inverse PCR reaction. Primers were designed such that the forward primer was 5' phosphorylated and started with the single nucleotide polymorphism (SNP) at the 5' end, followed by 20-24 nucleotides of p53 sequence. The reverse primer was designed to be complementary to the 20-24 nucleotides before the SNP. PCR was performed using Pwo polymerase which generated blunt ended products corresponding to the entire p53-containing vector. PCR products were gel purified, ligated to form circular plasmids and parental template DNA was digested with restriction endonuclease DpnI (New England Biolabs) to increase cloning efficiency. Ligated products were transformed into XLIBlue cells, and mutant p53 genes were verified by sequencing for the presence of the desired mutation and the absence of any secondary mutation introduced by PCR.

Expression of p53 in E. coli

Colonies of XLIBlue cells containing p53 plasmids were inoculated into 2 ml of LB medium containing ampicillin (70 micrograms/ml) in 48 well blocks (QIAGEN) and grown overnight at 37° C. in a shaking incubator. 40 µl of overnight culture was used to inoculate another 2 ml of LB/ampicillin in 48 well blocks and grown at 37° C. until an optical density (600 nm) of ~0.4 was reached. IPTG was then added to 50 µM and induction continued at 30° C. for 4 hours. Cells were then harvested by centrifugation and cell pellets stored at −80° C. For preparation of protein, cell pellets were thawed at room temperature and 40 µl of p53 buffer (25 mM HEPES pH 7.6, 50 mM KCl, 10% glycerol, 1 mM DTT, 1 mg/ml bovine serum albumin, 0.1% Triton X100) and 10 µl of 4 mg/ml lysozyme were added and vortexed to resuspend the cell pellet. Lysis was aided by incubation on a rocker at room temperature for 30 min before cell debris was collected by centrifugation at 13000 rpm for 10 min at 4° C. The cleared supernatant of soluble protein was removed and used immediately or stored at −20° C.

Western Blotting

Soluble protein samples were boiled in SDS containing buffer for 5 min prior to loading on 4-20% Tris-Glycine gels (NOVEX) and run at 200 V for 45 min. Protein was transferred onto PVDF membrane (Hybond-P, Amersham) and probed for the presence of various epitopes using standard techniques. For detection of the histidinetag, membranes were blocked in 5% Marvel/PBST and anti-RGSHis antibody (QIAGEN) was used as the primary antibody at 1/1000 dilution. For detection of the biotin tag, membranes were blocked in Superblock/TBS (Pierce) and probed with Streptavidin-HRP conjugate (Amersham) at 1/2000 dilution in Superblock/TBS/0.1% Tween20. The secondary antibody for the RGSHis antibody was anti-mouse IgG (Fe specific) HRP conjugate (Sigma) used at 1/2000 dilution in Marvel/PBST. After extensive washing, bound HRP conjugates were detected using either ECLPlus (Amersham) and Hyperfilm ECL (Amersham) or by DAB staining (Pierce).

DNA Gel Shift Assay

DNA binding function of expressed p53 was assayed using a conventional gel shift assay. Oligos DIGGADD45A (5'DIG-gta cag aac atg tct aag cat gct ggg gac-3'; SEQ ID N0:3) and GADD45B (gtc ccc age atg ctt aga cat gtt ctg tac 3'; SEQ ID N0:4) were annealed together to give a final concentration of 25 I-lM dsDNA. Binding reactions were assembled containing I µl of cleared lysate, 0.2 ul of annealed DIG-labelled GADD45 oligos and 1 µl of polydI/ dC competitor DNA (Sigma) in 20 μl of p53 buffer. Reactions were incubated at room temperature for 30 min, chilled on ice and 5 μl loaded onto a pre-run 6% polyacrylamide/TBE gel (NOVEX). Gels were run at 100 V at 4 DC for 90 min before being transferred onto positively charged nitrocellulose (Roche). Membranes were blocked in 0.4% Blocking Reagent (Roche) in Buffer 1 (100 mM maleic acid, 150 mM NaCl, pH 7.0) for 30 min and probed for presence of DIG-labelled DNA with anti-DIG Fab fragments conjugated to HRP (Roche). Bound HRP conjugates were detected using ECLPlus and Hyperfilm ECL (Amersham).

p53 Phosphorylation Assay

Phosphorylation of p53 was performed using purified casein kinase II (CKII, Sigma). This kinase has previously been shown to phosphorylate wild type p53 at serine 392. Phosphorylation reactions contained 2 μl of p53 lysate, 10 mM $MgCl_2$, 100 μM ATP and 0.1 U of CKII in 20 μl of p53 buffer. Reactions were incubated at 30° C. for 30 min, reaction products separated through 4-20% NOVEX gels and transferred onto PVDF membrane. Phosphorylation of p53 was detected using an antibody specific for phosphorylation of p53 at serine 392 (Cell Signalling Technology), used at 1/1000 dilution in Marvel/TBST. Secondary antibody was an anti-rabbit HRP conjugate (Cell Signalling Technology), used at 1/2000 dilution.

MDM2 Interaction Assay

The cDNA for the N-terminal portion of MDM2 (amino acids 17-127) was amplified from a cDNA library and cloned downstream of sequences coding for a His-tag and a FLAG-tag in an E. coli expression vector. Plasmids were checked by sequencing for correct MDM2 sequence and induction of E. coli cultures showed expression of a His and FLAG tagged soluble protein of the expected size. To test for interaction between MDM2 and the p53 mutant panel, binding reactions were assembled containing 10 μl p53 containing lysate, 10 μl MDM2 containing lysate, 20 μl anti-FLAG agarose in 500 μl phosphate buffered saline containing 300 mM NaCl, 0.1% Tween20 and 1% (w/v) bovine serum albumin. Reactions were incubated on a rocker at room temperature for 1 hour and FLAG bound complexes harvested by centrifugation at 5000 rpm for 2 min. After extensive washing in PBST, FLAG bound complexes were denatured in SDS sample buffer and Western blotted. Presence of biotinylated p53 was detected by Streptavidin/HRP conjugate.

p53 Microarray Fabrication and Assays

Cleared lysates of the p53 mutant panel were loaded onto a 384 well plate and printed onto SAM2™ membrane (Promega, Madison, Wis., USA) using a custom built robot (K-Biosystems, UK) with a 16 pin microarraying head. Each lysate was spotted 4 Limes onto each array, and each spot was printed onto 3 times. After printing, arrays were wet in p53 buffer and blocked in 5% Marvel/p53 buffer for 30 min. After washing 3×5 min in p53 buffer, arrays were ready for assay.

For DNA binding assay, 5 μl of annealed Cy3-labelled GADD45 oligo was added to 500 μl p53 buffer. The probe solution was washed over the array at room temperature for 30 min, and washed for 3×5 min in p53 buffer. Arrays were then dried and mounted onto glass slides for scanning in an Affymetrix 428 array scanner. Quantification of Cy3 scanned images was accomplished using ImaGene software.

For the phosphorylation assay, 10 μl CKII was incubated with the arrays in 320 μl p53 buffer and 80 μl Mg/ATP mix at 30° C. for 30 min. Arrays were then washed for 3×5 min in TBST and anti-phosphoserine 392 antibody added at 1/1000 dilution in Marvel/TBST for 1 h. After washing for 3×5 min in TBST, anti-rabbit secondary antibody was added at 1/2000 dilution for 1 h. Bound antibody was detected by ECLPlus and Hyperfilm.

For the MDM2 interaction assay, 1 μl of purified Cy3 labelled MDM2 protein was incubated with the arrays in 500 μl PBS/300 mM NaCl/0.1% Tween20/1% BSA for 1 h at room temperature. After washing for 3×5 min in the same buffer, arrays were dried, mounted onto glass slides and analysed for Cy3 fluorescence as for the DNA binding assay.

Results

Expression of p53 in E. coli and Construction of Mutant Panel

Figure 1:
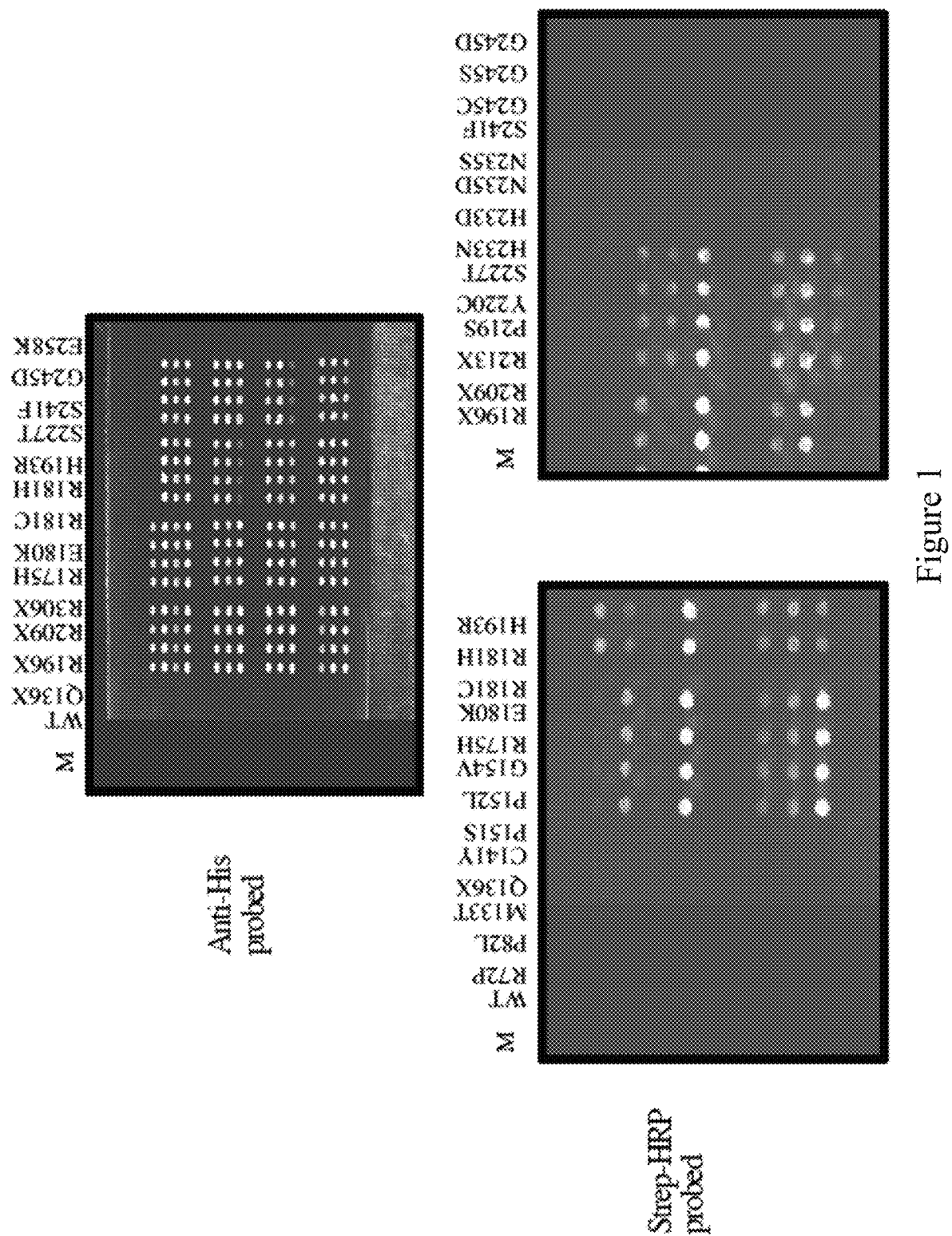
FIG. 1 shows p53 mutant panel expression. E. coli cells containing plasmids encoding human wild type p53 or the indicated mutants were induced for 4 h at 30 C. Cells were lysed by the addition of lysozyme and Triton X100 and cleared lysates were analysed by Western blot. A band corresponding to full length his-tagged, biotinylated p53 runs at around 70 kDa.

The full length p53 open reading frame was amplified from a Hela cell cDNA library by PCR and cloned downstream of the tac promoter in vector pQE80L into which the BCCP domain from the E. coli gene ACCB had already been cloned. The resultant p53 would then be His and biotin tagged at its N-terminus, and FIG. 1 shows Western blot analysis of soluble protein from induced E. coli cultures. There is a clear signal for His-tagged, biotinylated protein at around 66 kDa, and a band of the same size is detected by the p53 specific antibody pAb1801 (data not shown). The plasmid encoding this protein was fully sequenced and shown to be wild type p53 cDNA sequence. This plasmid was used as the template to construct the mutant panel, and FIG. 1 also shows analysis of the expression of a selection of those mutants, showing full length protein as expected for the single nucleotide polymorphisms, and truncated proteins where the mutation codes for a STOP codon. The mutants were also sequenced to confirm presence of the desired mutation and absence of any secondary mutations.

Although the Inventors have used His and biotin tags in this example of a SNP array, other affinity tags (eg FLAG, myc, VSV) can be used to enable purification of the cloned proteins. Also an expression host other than E. coli can be used (eg. yeast, insect cells, mammalian cells) if required.

Also, although this array was focussed on the naturally occurring germline SNPs of p53, other embodiments are not necessarily restricted to naturally occurring SNPs ("synthetic" mutants) or versions of the wild type protein which contain more than one SNP. Other embodiments can contain versions of the protein which are deleted from either or both ends (a nested-set). Such arrays would be useful in mapping protein:ligand interactions and delineating functional domains of unknown proteins.

E. coli Expressed p53 is Functional for DNA Binding

Figure 2:
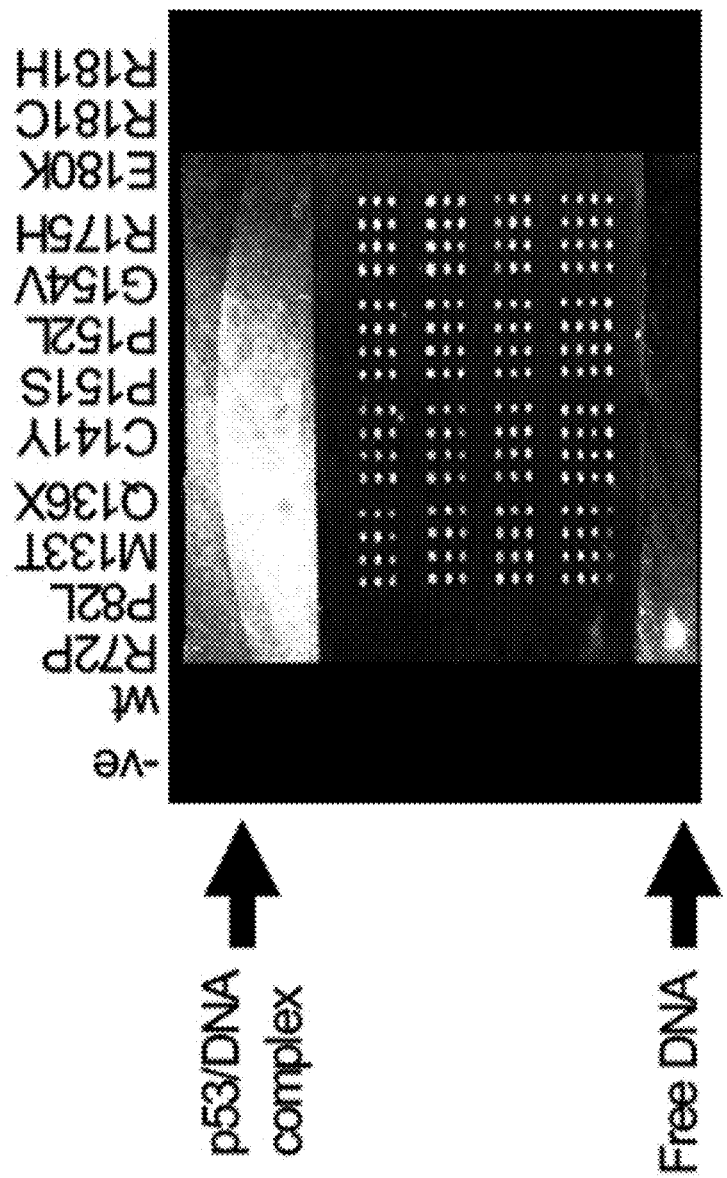
FIG. 2 shows a gel shift assay to demonstrate DNA binding function of E. coli expressed p53. 1 ul of cleared E. coli lysate containing wild type p53 (wt) or the indicated mutant was combined with 250 nM DIG-labelled DNA and 0.05 mg/ml polydI/dC competitor DNA. The −ve control contained only DNA. Bound and free DNA was separated through a 6% gel (NOVEX), transferred to positively charged membrane (Roche) and DIG-labelled DNA detected using an anti-DIG HRP conjugated antibody (Roche). The DNA:p53 complex is indicated by an arrow.
Figure 3:
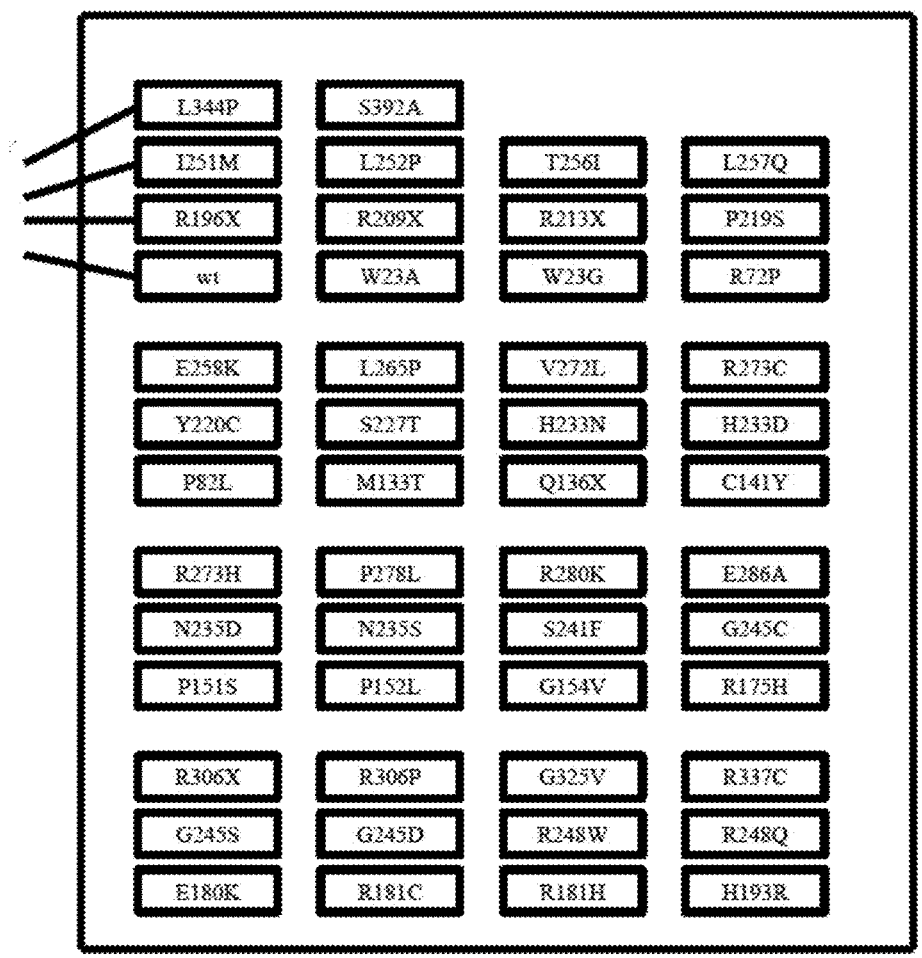
FIG. 3 shows microarray data for the p53 DNA binding assay. Lysates were arrayed in a 4×4 pattern onto streptavidin capture membrane as detailed in A) and probed with B) Cy3-labelled anti-histidine antibody or C) Cy3-labelled GADD45 DNA, prior to scanning in an Affymetrix 428 array scanner.

To demonstrate functionality of our p53, the Inventors performed electrophoretic mobility shift assays using a DNA oligo previously shown to be bound by p53. FIG. 2 shows an example result from these gel shift assays, showing DNA binding by wild type p53 as well as mutants R72P, P82L and R181C. The first 2 mutants would still be expected to bind DNA as these mutations are outside of the DNA binding domain of p53. Having demonstrated DNA binding using a conventional gel based assay, the Inventors then wanted to show the same function for p53 arrayed on a surface. FIG. 3C shows the result of binding Cy3-labelled DNA to the p53 mutant panel arrayed onto SAM2™ membrane (Promega, Madison. Wis., USA). Although the Inventors have used SAM2™ membrane in this example of a SNP array, other surfaces which can be used for arraying proteins onto include but are not restricted to glass, polypropylene, polystyrene, gold or silica slides, polypropylene or polystyrene multi-well plates, or other porous surfaces such as nitrocellulose, PVDF and nylon membranes. The SAM2™ membrane specifically captures biotinylated molecules and so purifies the biotinylated p53 proteins from the mutant panel cell lysates. After washing unbound DNA from the array, bound DNA was visualised using an Affymetrix DNA array scanner. As can be seen from FIG. 3, the same mutants which bound DNA in the gel shift assay also bound the most DNA when arrayed on a surface. Indeed, for a DNA binding assay the microarray assay appeared to be more sensitive than the conventional gel shift assay. This is probably because in a gel shift assay the DNA:protein complex has to remain bound during gel electrophoresis, and weak complexes may dissociate during this step. Also the 3-dimensional matrix of the SAM2™ membrane used may have a caging effect. The amount of p53 protein is equivalent on each spot, as shown by an identical microarray probed for His-tagged protein (FIG. 3B).

Use of the p53 Array for Phosphorylation Studies

Figure 4:
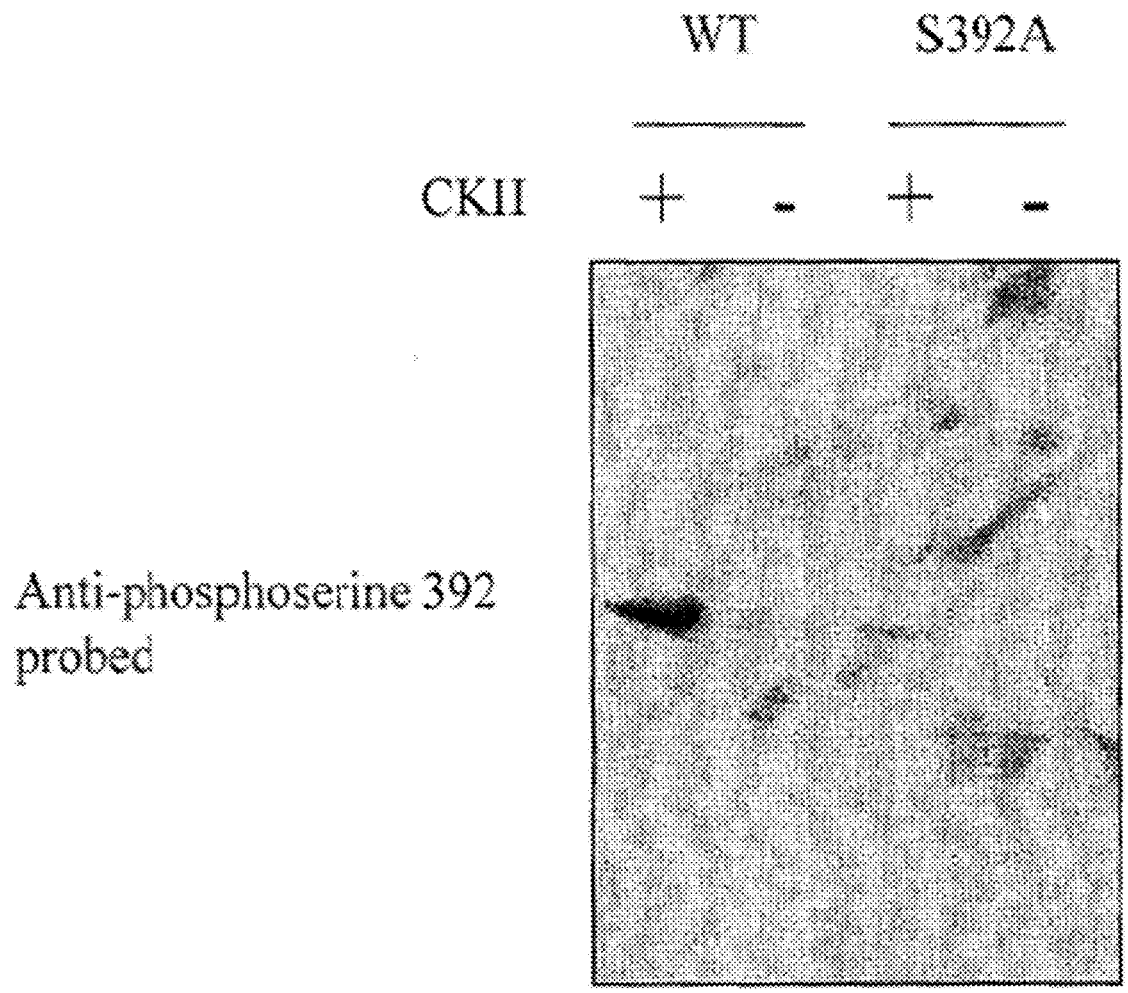
FIG. 4 shows CKII phosphorylation of p53. 2 ul of E. coli lysate containing p53 wild type (wt) or the indicated mutant protein were incubated with or without casein kinase II in a buffer containing ATP for 30 min at 30 C. Reactions were Western blotted and phosphorylation at serine 392 detected using a phosphorylation specific antibody.
Figure 5:
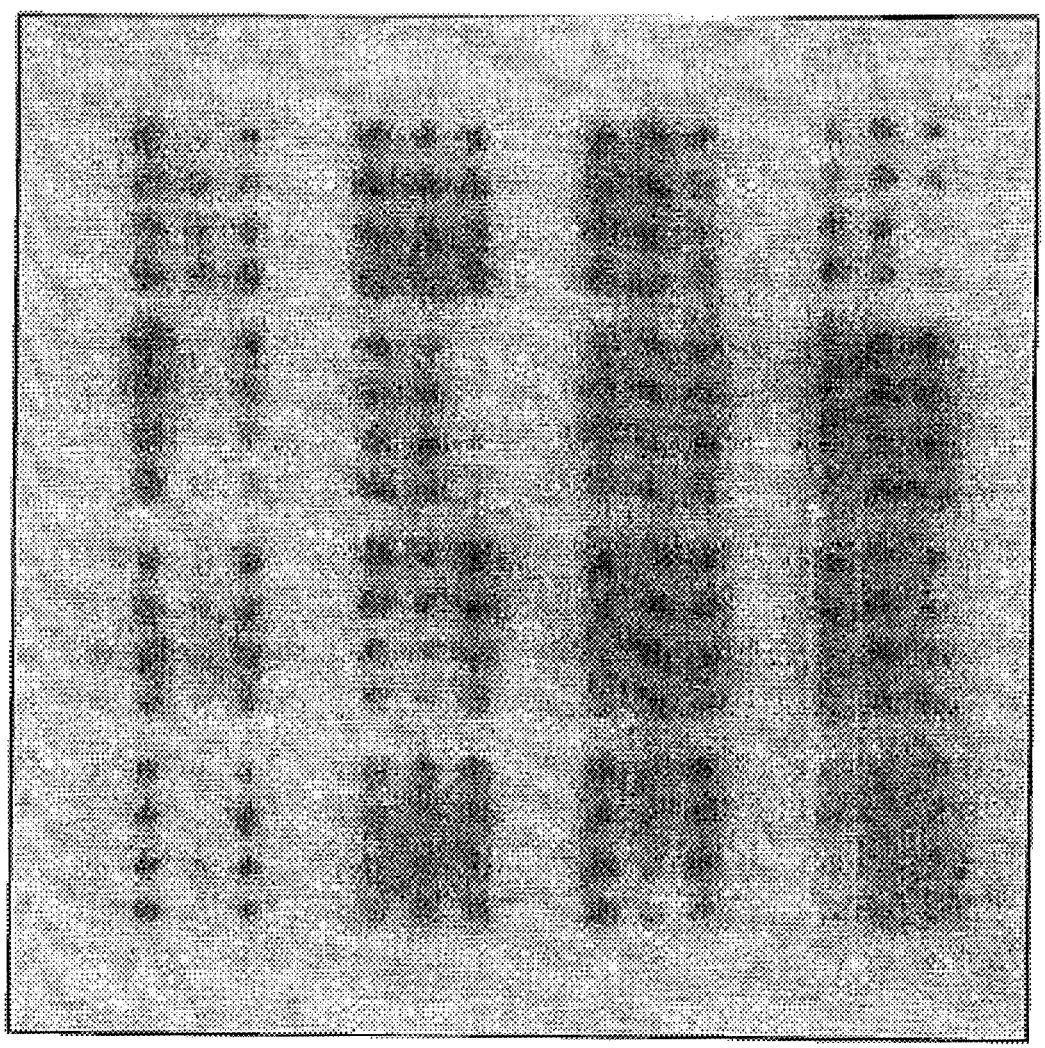
FIG. 5 shows microarray data for the CKII phosphorylation assay. The p53 array was incubated with CKII and ATP for 1 h at 30 C and analysed for phosphorylation at serine 392. Phosphorylation was detected for all proteins on the array except for the truncation mutants Q136X, R196X, R209X, R213X, R306X and for the amino acid mutants L344P and S392A.

To exemplify the study of the effect of SNPs on post-translational modifications, the Inventors chose to look at phosphorylation of the p53 array by casein kinase II. This enzyme has previously been shown to phosphorylate p53 at serine 392, and the Inventors made use of a commercially available anti-p53 phosphoserine 392 specific antibody to study this event. FIG. 4 shows Western blot analysis of kinase reactions on soluble protein preparations from p53 wild type and S392A clones. Lane 1 shows phosphorylation of wild type p53 by CKII, with a background signal when CKII is omitted from the reaction (lane 2). Lanes 3 and 4 show the corresponding results for S392A, which as expected only shows background signal for phosphorylation by CKII. This assay was then applied in a microarray format, which as can be seen from FIG. 5 shows phosphorylation for all of the mutant panel except the S392A mutant and those mutants which are truncated before residue 392.

Use of the p53 Array to Study a Protein:Protein Interaction

Figure 6:
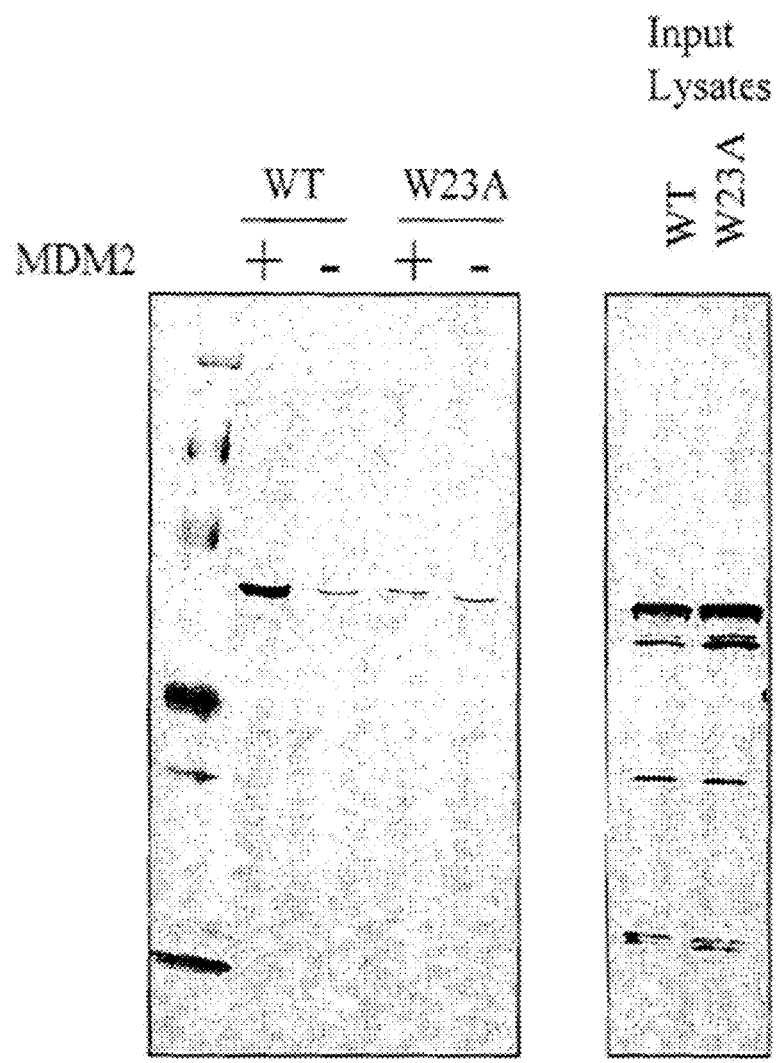
FIG. 6 shows a solution phase MDM2 interaction assay. 10 ul of p53 containing lysate was incubated with 10 ul of MDM2 containing lysate and 20 ul anti-FLAG agarose in a total volume of 500 ul. After incubation for 1 h at room temperature the anti-FLAG agarose was collected by centrifugation, washed extensively and bound proteins analysed by Western blotting. P53 proteins were detected by Strep/HRP conjugate.
Figure 7:
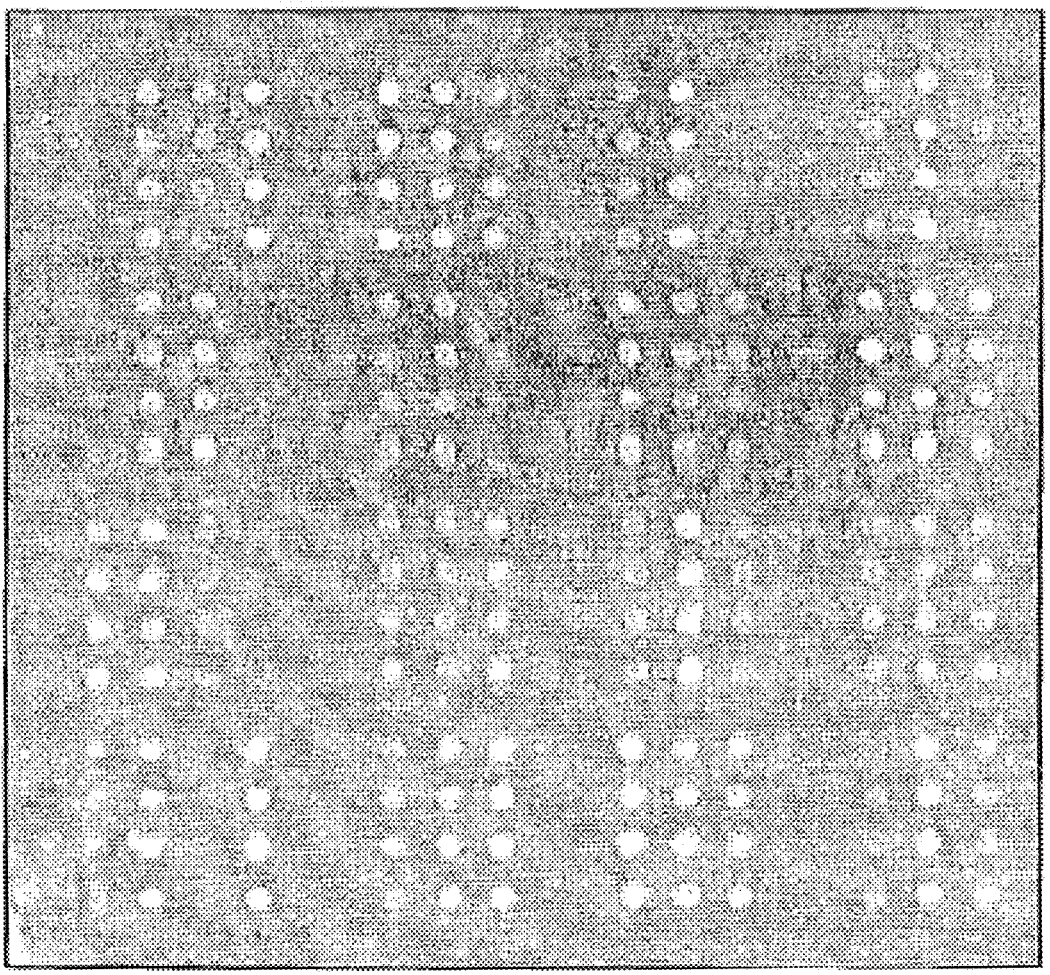
FIG. 7 shows microarray data for MDM2 interaction. The p53 array was incubated with purified Cy3-labelled MDM2 protein for 1 h at room temperature and bound MDM2 protein detected using a DNA array scanner (Affymetrix). MDM2 protein bound to all members of the array apart from the W23A and W23G mutants.

To exemplify the study of a protein:protein interaction on a SNP protein array, the interaction of MDM2 with the p53 protein array was investigated. FIG. 6 shows that FLAG-tagged MDM2 pulls down wild type p53 when bound to anti-FLAG agarose. However the W23A mutant is not pulled down by FLAG agarose bound MDM2, which would be expected as this residue has previously been shown to be critical for the p53/MDM2 interaction (Bottger, A., Bottger, V., Garcia-Echeverria, C., et al, J. Mol. Biol. (1997) 269: 744-756). This assay was then carried out in a microarray format, and FIG. 7 shows the result of this assay, with Cy3-labelled protein being detected at all spots apart from the W23A and W23G mutant spots.

The Inventors have used a novel protein chip technology to characterise the effect of 46 germline mutations on human p53 protein function. The arrayed proteins can be detected by both a His-tagged antibody and also a p53 specific antibody. This array can be used to screen for mutation specific antibodies which could have implications for p53 status diagnosis.

The Inventors were able to demonstrate functionality of the wild type protein by conventional gel based assays, and have achieved similar results performing the assays in a microarray format. Indeed, for a DNA binding assay the microarray assay appeared to be more sensitive than the conventional gel shift assay. These arrays can be stored at −20 C in 50% glycerol and have been shown to still be functional for DNA binding after 1 month (data not shown).

The CKII phosphorylation assay results are as expected, with phosphorylation being detected for all proteins which contained the serine at residue 392. This analysis can obviously be extended to a screen for kinases that phosphorylate p53, or for instance for kinases that differentially phosphorylate some mutants and not others, which could themselves represent potential targets in cancer.

The MDM2 interaction assay again shows the validity of the protein array format, with results for wild type and the p53 mutants mirroring those obtained using a more conventional pull down assay. These results also show that our protein arrays can be used to detect protein:protein interactions. Potentially these arrays can be used to obtain quantitative binding data (ie $K_D$ values) for protein:protein interactions in a high-throughput manner not possible using current methodology. The fact that the MDM2 protein was pulled out of a crude E. coli lysate onto the array bodes well for envisioned protein profiling experiments, where for instance cell extracts are prepared from different patients, labelled with different fluorophores and both hybridised to the same array to look for differences in amounts of protein interacting species.

Indeed, in Example 2 below the applicant has gone on to demonstrate that these arrays can be used to obtain quantative data.

Example 2 Quantitative DNA Binding on the p53 Protein Microarray

Methods
DNA-Binding Assays.

Oligonucleotides with the GADD45 promoter element sequence (5'-gta cag aac atg tct aag cat gct ggg gac-3'; SEQ ID NO:3 and 5'-gtc ccc age atg ctt aga cat gtt ctg tac-3'; SEQ ID NO:4) were radiolabelled with gamma $^{33}$P-ATP (Amersham Biosciences, Buckinghamshire, UK) and T4 kinase (Invitrogen, Carlsbad, Calif.), annealed in p53 buffer and then purified using a Nucleotide Extraction column (Qiagen, Valencia, Calif.). The duplex oligos were quantified by UV spectrophotometry and a 2.5 fold dilution series made in p53 buffer. 500 µl of each dilution were incubated with microarrays at room temperature for 30 min, then washed three times for 5 min in p53 buffer to remove unbound DNA. Microarrays were then exposed to a phosphorimager plate (Fuji, Japan) overnight prior to scanning. ImaGene software (BioDiscovery, Marina del Rey, Calif.) was used to quantify the scanned images. Replicate values for all mutants at each DNA concentration were fitted to simple hyperbolic concentration-response curves $R=B_{max}/((K_d/L)+1)$, where R is the response in relative counts and L is the DNA concentration in nM.

Results
Binding of p53 to GADD45 Promoter Element DNA.

Figure 8A:
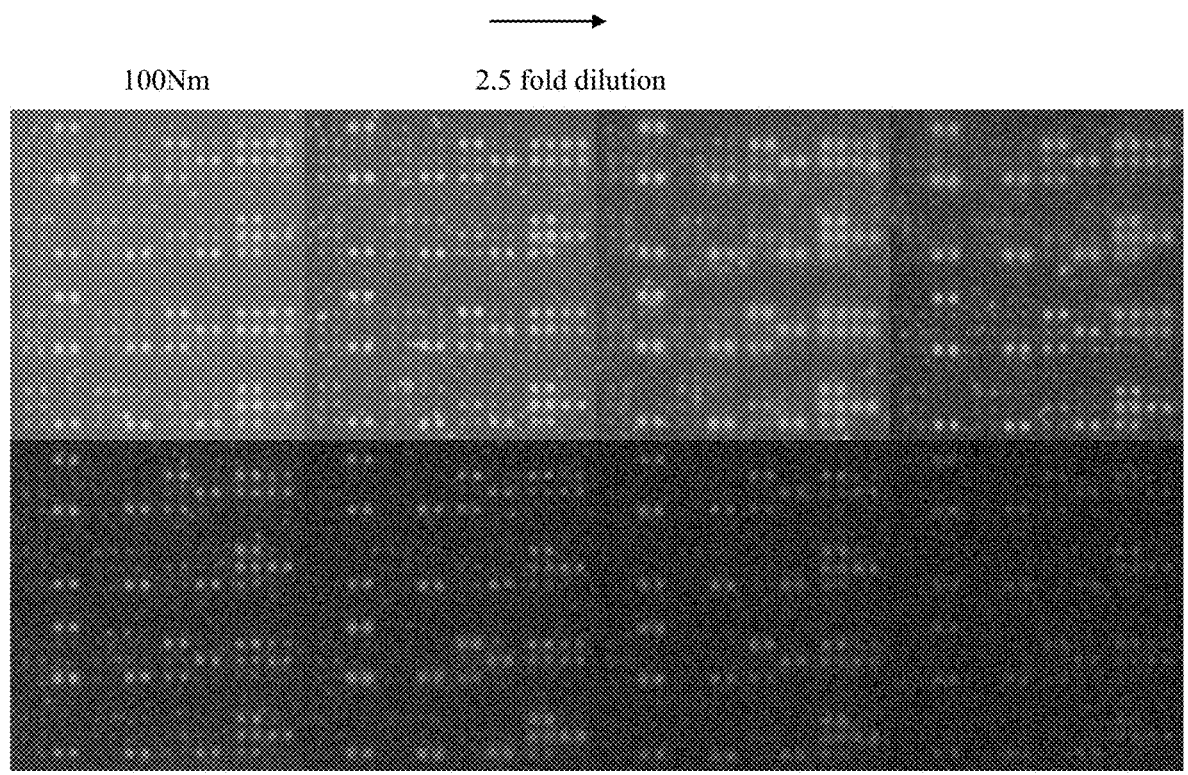
FIG. 8a shows replicate p53 microarrays incubated in the presence of $^{33}$P labelled duplex DNA, corresponding to the sequence of the GADD45 promoter element, at varying concentrations and imaged using a phosphorimager so individual spots could be quantified.

Replicate p53 microarrays were incubated in the presence of $^{33}$P labelled duplex DNA, corresponding to the sequence of the GADD45 promoter element, at varying concentrations (FIG. 8A). The microarrays were imaged using a phosphorimager and individual spots quantified. The data were normalised against a calibration curve to compensate for the non-linearity of this method of detection and backgrounds were subtracted. Replicate values for all mutants were plotted and analysed by non-linear regression analysis allowing calculation of both $K_d$ and $B_{max}$ values (Table 1).

TABLE 1

| Mutation | DNA binding $B_{max}$ (% wild-type) | $K_d$ (nM) | MDM2 | CKII |
|---|---|---|---|---|
| Wild-type | 100 (90-110) | 7 (5-10) | + | + |
| W23A | 131 (119-144) | 7 (5-10) | − | + |
| W23G | 84 (74-94) | 5 (3-9) | − | + |

TABLE 1-continued

| Mutation | DNA binding $B_{max}$ (% wild-type) | $K_d$ (nM) | MDM2 | CKII |
|---|---|---|---|---|
| R72P | 121 (110-132) | 9 (7-13) | + | + |
| P82L | 70 (63-77) | 7 (5-10) | + | + |
| M133T | ND | | + | + |
| Q136X | No binding | | + | − |
| C141Y | ND | | + | + |
| P151S | ND | | + | + |
| P152L | 31 (23-38) | 18 (9-37) | + | + |
| G154V | ND | | + | + |
| R175H | ND | | + | + |
| E180K | 31 (21-41) | 12 (4-35) | + | + |
| R181C | 88 (81-95) | 11 (8-13) | + | + |
| R181H | 48 (40-57) | 11 (6-21) | + | + |
| H193R | 21 (16-26) | 22 (11-42) | + | + |
| R196X | No binding | | + | − |
| R209X | No binding | | + | − |
| R213X | No binding | | + | − |
| P219S | 21 (14-30) | 10 (3-33) | + | + |
| Y220C | ND | | + | + |
| S227T | 101 (94-110) | 7 (5-9) | + | + |
| H233N | 60 (52-68) | 5 (3-8) | + | + |
| H233D | 70 (58-84) | 7 (3-14) | + | + |
| N235D | 32 (25-40) | 27 (15-49) | + | + |
| N235S | 46 (36-56) | 9 (4-20) | + | + |
| S241F | 38 (30-47) | 19 (10-37) | + | + |
| G245C | ND | | + | + |
| G245S | 44 (38-51) | 11 (7-18) | + | + |
| G245D | ND | | + | + |
| R248W | 107 (95-120) | 12 (8-17) | + | + |
| R248Q | 85 (77-95) | 17 (12-23) | + | + |
| I251M | ND | | + | + |
| L252P | 22 (12-32) | 16 (4-63) | + | + |
| T256I | 32 (22-41) | 14 (6-34) | + | + |
| L257Q | 26 (19-35) | 17 (7-44) | + | + |
| F258K | ND | | + | + |
| L265P | ND | | + | + |
| V272L | ND | | + | + |
| R273C | 70 (56-85) | 20 (11-37) | + | + |
| R273H | 59 (40-79) | 54 (27-106) | + | + |
| P278L | ND | | + | + |
| R280K | 54 (40-70) | 21 (9-46) | + | + |
| E286A | 32 (23-41) | 22 (10-46) | + | + |
| R306X | No binding | | + | − |
| R306P | 90 (81-100) | 7 (5-11) | + | + |
| G325V | 73 (67-79) | 7 (5-10) | + | + |
| R337C | 88 (80-95) | 6 (4-8) | + | + |
| L344P | No binding | | + | − |
| S392A | 121 (107-136) | 10 (6-14) | + | − |

Figure 8B:
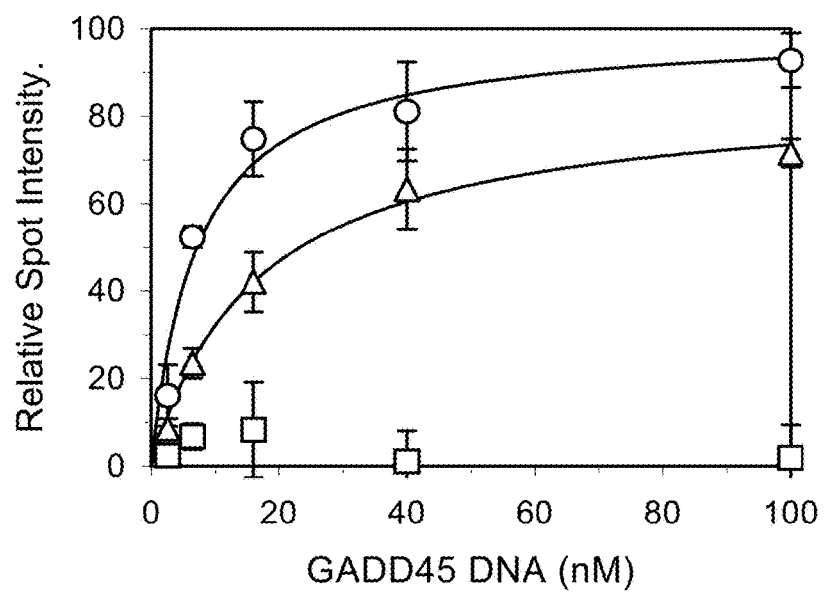
FIG. 8B shows DNA binding to wild-type p53 (high affinity), R273H (low affinity) and L344P (non-binder) predicting a wild-type affinity of 7 nM.

FIG. 8B shows DNA binding to wild-type p53 (high affinity), R273H (low affinity) and L344P (non-binder) predicting a wild-type affinity of 7 nM.

Discussion

DNA Binding.

Quantitative analysis of the DNA binding data obtained from the microarrays yielded both affinities ($K_d$) and relative maximum binding values ($B_{max}$) for wild-type and mutant p53. Protein function microarrays have not previously been used in this way and this data therefore demonstrate their usefulness in obtaining this quality and amount of data in a parallel fashion. The approach of normalising binding data for the amount of affinity-tagged protein in the spot provides a rapid means of analysing large data sets [Zhu, H. et al. Global analysis of protein activities using proteome chips. Science 293, 2101-2105 (2001).], however it takes into account neither the varying specific activity of the microarrayed protein nor whether the signal is recorded under saturating or sub-saturating conditions. The quantitative analysis carried out here allowed the functional classification of mutants into groups according to GADD45 DNA binding: those showing near wild-type affinity; those exhibiting reduced stability (low $B_{max}$); those showing reduced affinity (higher $K_d$); and those showing complete loss of activity (Table 1).

Proteins with near wild-type affinity for DNA generally had mutations located outside of the DNA-binding domain and include R72P, P82L, R306P and G325V. R337C is known to affect the oligomerisation state of p53 but at the assay temperature used here it is thought to be largely tetrameric [Davison, T. S., Yin, P., Nie, E., Kay, C. & Arrowsmith, C. H. Characterisation of the oligomerisation defects of two p53 mutants found in families with Li-Fraumeni and Li-Fraumeni like syndrome. Oncogene 17, 651-656 (1998).], consistent with the affinity measured here. By contrast, total loss of binding was observed for mutations introducing premature stop codons (Q136X, R196X, R209X and R213X) and mutations that monomerise the protein (L344P [Lomax, M. E., Barnes, D. M., Hupp, T. R., Picksley, S. M. & Camplejohn, R. S. Characterisation of p53 oligomerisation domain mutations isolated from Li-Fraumeni and Li-Fraumeni like family members. Oncogene 17, 643-649 (1998).] and the tetramerisation domain deficient R306X) as expected.

Within the DNA-binding domain, the applicant found that mutations generally reduced or abolished DNA binding with the notable exceptions of R181C/H, S227T and H233N/D; these are all solvent exposed positions, distant from the protein-DNA interface and exhibit wild-type binding. Mutations R248Q/W, R273C/H and R280K, present at the protein-DNA interface, exhibited low affinities with $K_d$ values 2-7 times higher than wild-type (Table 1) consistent with either loss of specific protein-DNA interactions or steric hindrance through sub-optimal packing of the mutated residue.

Many of the remaining mutants fall into a group displaying considerably reduced specific activities, apparent from very low $B_{max}$ values, even when normalised according to the amount of protein present in the relevant spot. For some mutants, DNA binding was compromised to such a level that although binding was observed, it was not accurately quantifiable due to low signal to background ratios e.g. P151S and G245C. For others such as L252P, low signal intensities yielded measurable $K_d$ values, but with wide confidence limits.

To further demonstrate the applicability of the invention to protein arrays comprising at least two protein moieties derived from naturally occurring variants of a DNA sequence of interest such as, for example, those encoding proteins from phase 1 or phase 2 drug metabolising enzymes (DME's) the invention is further exemplified with reference to a p450 array. Phase 1 DME's include the Cytochrome p450's and the Flavin mono oxygenases (FMO's) and the Phase 2 DME's, UDP-glycosyltransferase (UGTs), glutathione S transferases (GSTs), sulfotransferases (SULTs), N-acetyltransferases (NATs), drug binding nuclear receptors and drug transporter proteins.

Preferably, the full complement, or a significant proportion of human DMEs are present on the arrays of the invention. Such an array can include (numbers in parenthesis currently described in the Swiss Prot database): all the human P450s (119), FMOs (5), UDP-glycosyltransferase (UGTs) (18), GSTs (20), sulfotransferases (SULTs) (6), N-acetyltransferases (NATs) (2), drug binding nuclear receptors (33) and drug transporter proteins (6). This protein list does not include those yet to be characterised from the human genome sequencing project, splice variants known to occur for the P450s that can switch substrate specificity or polymorphisms known to affect the function and substrate specificity of both the P450s and the phase 2 DMEs.

For example it is known that there are large differences in the frequency of occurrence of various alleles in P450s 2C9, 2D6 and 3A4 between different ethnic groups (see Tables 2, 3 and 4). These alleles have the potential to affect enzyme kinetics, substrate specificity, regio-selectivity and, where multiple products are produced, product profiles. Arrays of proteins described in this disclosure allow a more detailed examination of these differences for a particular drug and will be useful in predicting potential problems and also in effectively planning the population used for clinical trials.

TABLE 2

P450 2D6 Allele Frequency

| P450 | Allele | Mutation | Allele Frequency | Ethnic Group | Study Group | Reference |
|---|---|---|---|---|---|---|
| 2D6 | *1 | W.T. | 26.9% | Chinese | 113 | (1) |
|  |  |  | 36.4% | German | 589 | (2) |
|  |  |  | 36% | Caucasian | 195 | (3) |
|  |  |  | 33% | European | 1344 | (4) |
| 2D6 | *2 | R296C; S486T | 13.4% | Chinese | 113 | (1) |
|  |  |  | 32.4% | German | 589 | (2) |
|  |  |  | 29% | Caucasian | 195 | (3) |
|  |  |  | 27.1% | European | 1344 | (4) |
| 2D6 | *3 | Frameshift | 2% | German | 589 | (2) |
|  |  |  | 1% | Caucasian | 195 | (3) |
|  |  |  | 1.9% | European | 1344 | (4) |
| 2D6 | *4 | Splicing defect | 20.7% | German | 589 | (2) |
|  |  |  | 20% | Caucasian | 195 | (3) |
|  |  |  | 16.6% | European | 1344 | (4) |
|  |  |  | 1.2% | Ethiopian | 115 | (5) |
| 2D6 | *5 | Deletion | 4% | Caucasian | 195 | (3) |
|  |  |  | 6.9% | European | 1344 | (4) |
| 2D6 | *6 | Splicing defect | 0.93% | German | 589 | (2) |
|  |  |  | 1.3% | Caucasian | 195 | (3) |
| 2D6 | *7 | H324P | 0.08% | German | 589 | (2) |
|  |  |  | 0.3% | Caucasian | 195 | (3) |
|  |  |  | 0.1% | European | 1344 | (4) |
| 2D6 | *9 | K281del | 2% | Caucasian | 195 | (3) |
|  |  |  | 2.7% | European | 1344 | (4) |
| 2D6 | *10 | P34S; S486T | 50.7% | Chinese | 113 | (1) |
|  |  |  | 1.53% | German | 589 | (2) |
|  |  |  | 2% | Caucasian | 195 | (3) |
|  |  |  | 1.5% | European | 1344 | (4) |
|  |  |  | 8.6% | Ethiopian | 115 | (5) |
| 2D6 | *12 | G42R; R296C; S486T | 0% | German | 589 | (2) |
|  |  |  | 0.1% | European | 1344 | (4) |
| 2D6 | *14 | P34S; G169R; R296C; S486T | 0.1% | European | 1344 | (4) |
| 2D6 | *17 | T107I; R296C; S486T | 0% | Caucasian | 195 | (3) |
|  |  |  | 0.1% | European | 1344 | (4) |
|  |  |  | 9% | Ethiopian | 115 | (5) |
|  |  |  | 34% | African | 388 | (6) |

All other P450 allelic variants occur at a frequency of 0.1% or less (4).

TABLE 3

P450 2C9 Allele Frequency

| P450 | Allele | Mutation | Allele Frequency | Ethnic Group | Study Group | Reference |
|---|---|---|---|---|---|---|
| 2C9 | *1 | W.T. | 62% | Caucasian | 52 | (7) |
| 2C9 | *2 | R144C | 17% | Caucasian | 52 | (7) |
| 2C9 | *3 | I359L | 19% | Caucasian | 52 | (7) |
| 2C9 | *4 | I359T | x % | Japanese | X | (8) |

TABLE 3-continued

P450 2C9 Allele Frequency

| P450 | Allele | Mutation | Allele Frequency | Ethnic Group | Study Group | Reference |
|---|---|---|---|---|---|---|
| 2C9 | *5 | D360E | 0% | Caucasians | 140 | (9) |
|  |  |  | 3% | African-Americans | 120 | (9) |
| 2C9 | *7 | Y358C | x % |  | X | Swiss Prot |

TABLE 4

P450 3A4 Allele Frequency

| P450 | Allele | Mutation | Allele Frequency | Ethnic Group | Study Group | Reference |
|---|---|---|---|---|---|---|
| 3A4 | *1 | W.T. | >80% |  | X |  |
| 3A4 | *2 | S222P | 2.7% | Caucasian | X | (10) |
|  |  |  | 0% | African | x | (10) |
|  |  |  | 0% | Chinese | x | (10) |
| 3A4 | *3 | M445T | 1% | Chinese | X | (10) |
|  |  |  | 0.47% | European | 213 | (11) |
|  |  |  | 4% | Caucasian | 72 | (12) |
| 3A4 | *4 | I118V | 2.9% | Chinese | 102 | (13) |
| 3A4 | *5 | P218R | 2% | Chinese | 102 | (13) |
| 3A4 | *7 | G56D | 1.4% | European | 213 | (11) |
| 3A4 | *8 | R130Q | 0.33% | European | 213 | (11) |
| 3A4 | *9 | V170I | 0.24% | European | 213 | (11) |
| 3A4 | *10 | D174H | 0.24% | European | 213 | (11) |
| 3A4 | *11 | T363M | 0.34% | European | 213 | (11) |
| 3A4 | *12 | L373F | 0.34% | European | 213 | (11) |
| 3A4 | *13 | P416L | 0.34% | European | 213 | (11) |
| 3A4 | *15 | R162Q | 4% | African | 72 | (12) |
| 3A4 | *17 | F189S | 2% | Caucasian | 72 | (12) |
| 3A4 | *18 | L293P | 2% | Asian | 72 | (12) |
| 3A4 | *19 | P467S | 2% | Asian | 72 | (12) |

REFERENCES

1. Johansson, I., Oscarson, M., Yue, Q. Y., Bertilsson, L., Sjoqvist, F. & Ingelman-Sundberg, M. (1994) *Mol Pharmacol* 46, 452-9.
2. Sachse, C., Brockmoller, J., Bauer, S. & Roots, I. (1997) *Am J Hum Genet* 60, 284-95.
3. Griese, E. U., Zanger, U. M., Brudermanns, U., Gaedigk, A., Mikus, G., Morike, K., Stuven, T. & Eichelbaum, M. (1998) *Pharmacogenetics* 8, 15-26.
4. Marez, D., Legrand, M., Sabbagh, N., Guidice, J. M., Spire, C., Lalitte, J. J., Meyer, U. A. & Broly, F. (1997) *Pharmacogenetics* 7, 193-202.
5. Aklillu, E., Persson, I., Bertilsson, L., Johansson, 1., Rodrigues, F. & Ingelman-Sundberg, M. (1996) *J Pharmacol Exp Ther* 278, 441-6.
6. Dandara, C., Masimirembwa, C. M., Magimba, A., Sayi, J., Kaaya, S., Sommers, D. K., Snyman, J. R. & Hasler, J. A. (2001) *Eur J Clin Pharmacol* 57, 11-7.
7. Aithal, G. P., Day, C. P., Kesteven, P. J. & Daly, A. K. (1999) *Lancet* 353, 717-9.
8. Imai, J., Ieiri, I., Mamiya, K., Miyahara, S., Furuumi, H., Nanba, E., Yamane, M., Fukumaki, Y., Ninomiya, H., Tashiro, N., Otsubo, K. & Higuchi, S. (2000) *Pharmacogenetics* 10, 85-9.
9. Dickmann, L. J., Rettie, A. E., Kneller, M. B., Kim, R. B., Wood, A. J., Stein, C. M., Wilkinson, G. R. & Schwarz, U. I. (2001) *Mol Pharmacol* 60, 382-7.
10. Sata, F., Sapone, A., Elizondo, G., Stocker, P., Miller, V. P., Zheng, W., Raunio, H., Crespi, C. L. & Gonzalez, F. J. (2000) *Clin Pharmacol Ther* 67, 48-56.

11. Eiselt, R., Domanski, T. L., Zibat, A., Mueller, R., Presecan-Siedel, E., Hustert, E., Zanger, U. M., Brockmoller, J., Klenk, H. P., Meyer, U. A., Khan, K. K., He, Y. A., Halpert, J. R. & Wojnowski, L. (2001) *Pharmacogenetics* 11, 447-58.

12. Dai, D., Tang, J., Rose, R., Hodgson, E., Bienstock, R. J., Mohrenweiser, H. W. & Goldstein, J. A. (2001) *J Pharmacol Exp Ther* 299, 825-31.

13. Hsieh, K. P., Lin, Y. Y., Cheng, C. L., Lai, M. L., Lin, M. S., Siest, J. P. & Huang, J. D. (2001) *Drug Metab Dispos* 29, 268-73.

Example 3: Cloning of Wild-Type *H. sapiens* Cytochrome P450 Enzymes CYP2C9, CYP2D6 and CYP3A4

The human cytochrome p450s have a conserved region at the N-terminus, this includes a hydrophobic region which faciliates lipid association, an acidic or 'stop transfer' region, which stops the protein being fed further into the membrane, and a partially conserved proline repeat. Three versions of the p450s were produced with deletions up to these domains, the N-terminal deletions are shown below.

| Construct | Version | N-terminal Deletion |
|---|---|---|
| T009-C23A4 | Proline | −34 AA |
| T009-C13A4 | Stop Transfer | −25 AA |
| T009-C33A4 | Hydrophobic peptide | −13 AA |
| T015-C22C9 | Proline | −28 AA |
| T015-C12C9 | Stop Transfer | −20 AA |
| T015-C32C9 | Hydrophobic peptide | −0AA |
| T017-Cl 2D6 | Proline | −29 AA |
| T017-C22D6 | Stop Transfer | −18 AA |
| T017-C32D6 | Hydrophobic peptide | −0AA |

Figure 9A:
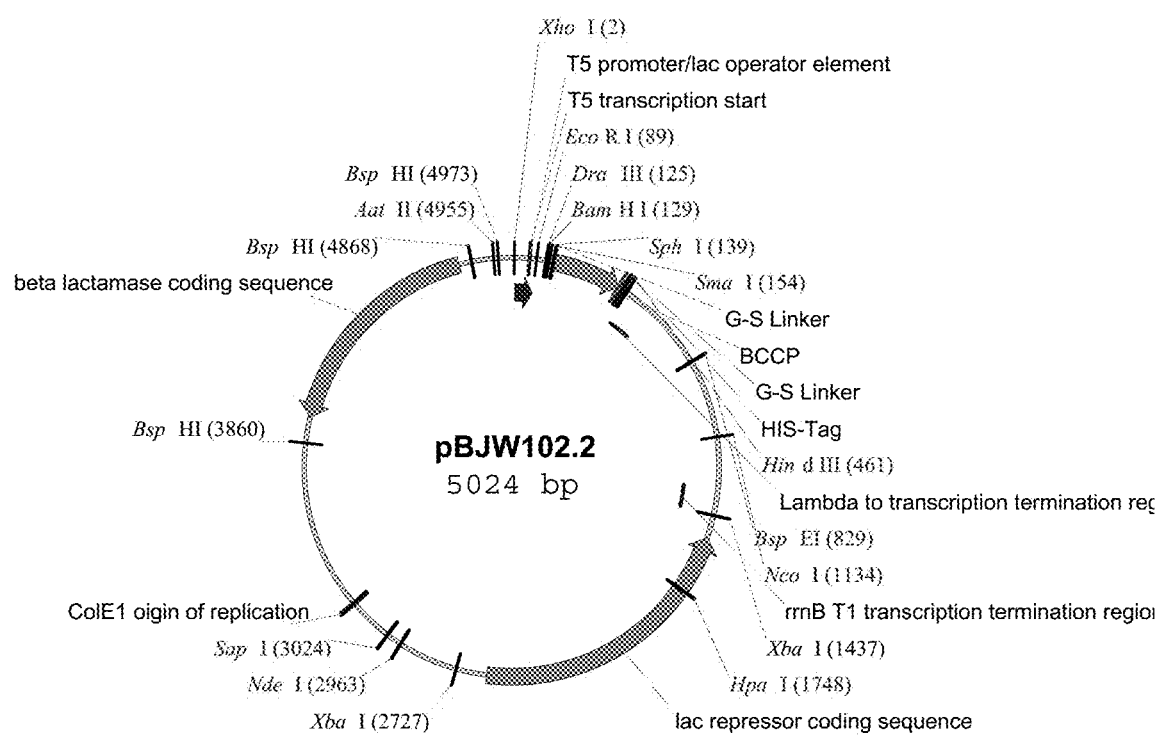
FIG. 9A shows a plasmid map of pBJWI02.2 for expression of C-terminal BCCP hexa-histidine constructs.

The human CYP2D6 was amplified by PCR from a pool of brain, heart and liver cDNA libraries (Clontech) using specific forward and reverse primers (T017F and T017R). The PCR products were cloned into the pMD004 expression vector, in frame with the N-terminal His-BCCP tag and using the NotI restriction site present in the reverse primer. To convert the CYP2D6 for expression in the C-terminal tag vector pBJWI02.2 (FIGS. 9A&B), primers were used which incorporated an SfiI cloning site at the 5' end and removed the stop codon at the 3' to allow in frame fusion with the C terminal tag. The primers T017CR together with either T017CF1, T017CF2, or T017CF3 allowed the deletion of 29, 18 and 0 amino acids from the N-terminus of CYP2D6 respectively.

Primer sequences are as follows:

T017F:
(SEQ ID NO: 5)
5'-GCTGCACGCTACCCACCAGGCCCCCTG-3'.

T017R:
(SEQ ID NO: 6)
5'-TTGCGGCCGCTCTTCTACTAGCGGGGCACAGCACAAAGCTCATAG-3'

T017CF1:
(SEQ ID NO: 7)
5'-TATTCTCACTGGCCATTACGGCCGCTGCACGCTACCCACCAGGCCCCCTG-3'

T017CF2:
(SEQ ID NO: 8)
5'-TATTCTCACTGGCCATTACGGCCGTGGACCTGATGCACCGGCGCCAACGCTGGGCTGCACGCTACCCACCAGGCCCCCTG-3'

T017CF3:
(SEQ ID NO: 9)
5'-TATTCTCACTGGCCATTACGGCCATGGCTCTAGAAGCACTGGTGCCCCTGGCCGTGATAGTGGCCATCTTCCTGCTCCTGGTGGACCTGATGCACCGGCGCCAACGC-3'

T017CR:
(SEQ ID NO: 10)
5'-GCGGGGCACAGCACAAAGCTCATAGGG-3'

PCR was performed in a 5 μl volume containing 0.5 μM of each primer, 125-250 μM dNTPs, 5 ng of template DNA, 1x reaction buffer, 1-5 units of polymerase (Pfu, Pwo, or 'Expand long template' polymerase mix), PCR cycle=95° C. 5 minutes, 95° C. 30 seconds, 50-70° C. 30 seconds, 72° C. 4 minutes×35 cycles, 72° C. 10 minutes, or in the case of Expand 68° C. was used for the extension step. PCR products were resolved by agarose gel electrophoresis, those products of the correct size were excised from the gel and subsequently purified using a gel extraction kit. Purified PCR products were then digested with either SfiI or NotI and ligated into the prepared vector backbone (FIG. 9C). Correct recombinant clones were determined by PCR screening of bacterial cultures, Western blotting and by DNA sequence analysis.

CYP3A4 and CYP2C9 were cloned from cDNA libraries by a methodology similar to that of CYP2D6. Primer sequences to amplify CYP3A4 and CYP2C9 for cloning into the N-terminal vectors are as follows:

2C9
T015F:
(SEQ ID NO: 11)
5'-CTCCCTCCTGGCCCCACTCCTCTCCCAA-3'

T015R:
(SEQ ID NO: 12)
5'-TTTGCGGCCGCTCTTCTATCAGACAGGAATGAAGCACAGCCTGGTA-3'

3A4
T009F:
(SEQ ID NO: 13)
5'-CTTGGAATTCCAGGGCCCACACCTCTG-3'

T009R:
(SEQ ID NO: 14)
5'-TTTGCGGCCGCTCTTCTATCAGGCTCCACTTACGGTGCCATCCCTTGA-3'

Primers to convert the N-terminal clones for expression in the C-terminal tagging vector are as follows:

3A4
T009CF1:
(SEQ ID NO: 15)
5'-TATTCTCACTGGCCATTACGGCCTATGGAACCCATTCACATGGACTTTTTAAGAAGCTTGGAATTCCAGGGCCCACACCTCTG-3'

T009CF2:
(SEQ ID NO: 16)
5'-TATTCTCACTGGCCATTACGGCCCTTGGAATTCCAGGGCCCACACCTCTG-3'

-continued

T009CF3:
(SEQ ID NO: 17)
5'-TTCTCACTGGCCATTACGGCCCCTCCTGGCTGTCAGCCTGGTGCTC
CCTATCTATATGGAACCCATTCACATGGACTTTTTAGG-3'

T009CR:
(SEQ ID NO: 18)
5'-GGCTCCACTTACGGTGCCATCCCTTGAC-3'

2C9
T015CFI:
(SEQ ID NO: 19)
5'-TATTCTCACTGGCCATTACGGCCAGACAGAGCTCTGGGAGAGGAAA
ACTCCCTCCTGGCCCCACTCCTCTCCCAG-3'

T015CF2:
(SEQ ID NO: 20)
5'-TATTCTCACTGGCCATTACGGCCCTCCCTCCTGGCCCCACTCCTCT
CCCAG-3'

T015CR:
(SEQ ID NO: 21)
5'-GACAGGAATGAAGCACAGCTGGTAGAAGG-3'

The full length or Hydrophobic peptide (C3) version of 2C9 was produced by inverse PCR using the 2C9-stop transfer clone (C 1) as the template and the following primers:

2C9-hydrophobic-peptide-F:
(SEQ ID NO: 22)
5'-CTCTCATGTTTGCTTCTCCTTTCACTCTGGAGACAGCGCTCTGGGA
GAGGAAAACTC-3'

2C9-hydrophobic-peptide-R:
(SEQ ID NO: 23)
5'-ACAGAGCACAAGGACCACAAGAGAATCGGCCGTAAGTGCCATAGTT
AATTTCTC-3'

Example 4: Cloning of NADPH-Cytochrome P450 Reductase

Figure 10A:
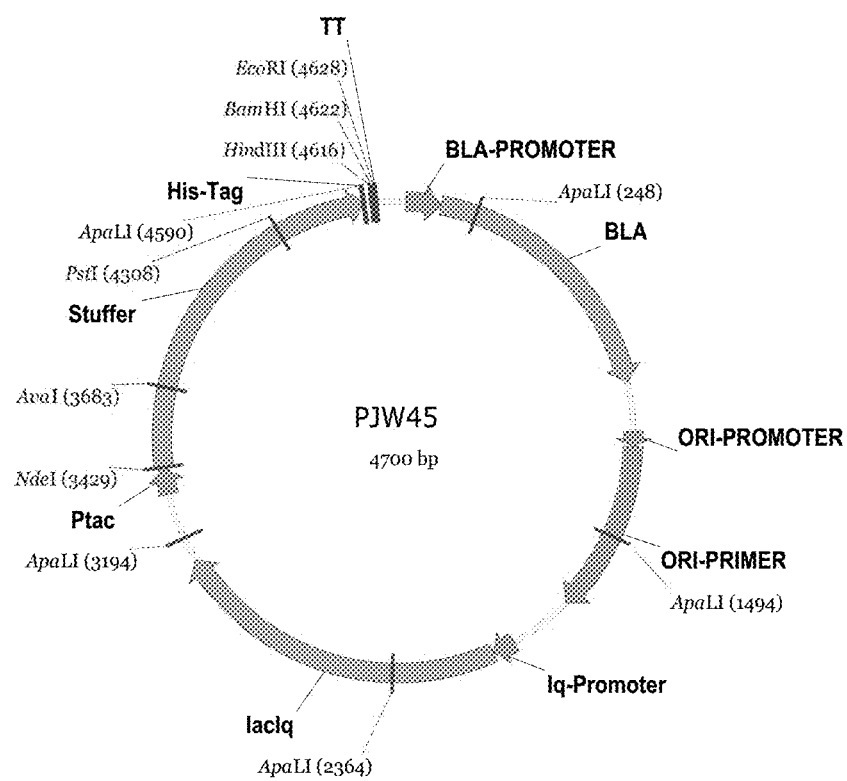
FIG. 10A shows a vector map of pJW45.

NADPH-cytochrome P450 reductase was amplified from fetal liver cDNA (Clontech), the PCR primers [NADPH reductase F1 5'-GATCGACATATGGGAGACTCC-CACGTGGACAC-3' (SEQ ID NO:24); NADPH reductase R1 5'-CCGATAAGCTFATCAGCTCCACACGTCCAGG-GAG-3'] (SEQ ID NO:25) incorporated a Nde I site at 5' and a Hind III site at the 3' of the gene to allow cloning. The PCR product was cloned into the pJW45 expression vector (FIGS. 10A&B)) two stop codons were included on the reverse primer to ensure that the His-tag was not translated. Correct recombinant clones were determined by PCR screening of bacterial cultures, and by sequencing.

Example 5: Cloning of Polymorphic Variants of *H. sapiens* Cytochrome P450s CYP2C9, CYP2D6 and CYP3A4

Once the correct wild-type CYP450s (FIGS. 11, 12, & 13) were cloned and verified by sequence analysis the naturally occurring polymorphisms of 2C9, 2D6 and 3A4 shown in Table 5 were created by an inverse PCR approach (except for CYP2D6*10 which was amplified and cloned as a linear PCR product in the same way as the initial cloning of CYP2D6 described in Example 3). In each case, the forward inverse PCR primer contained a 1 bp mismatch at the 5' position to substitute the wild type nucleotide for the polymorphic nucleotide as observed in the different ethnic populations.

TABLE 5

Polymorphic forms of P450 2C9, 2D6 and 3A4 cloned

| Cytochrome P450 polymorphism | Encoded amino acid subsitutions |
|---|---|
| CYP2C9*1 | wild-type |
| CYF2C9*2 | R144C |
| CYF2C9*3 | I359L |
| CYP2C9*4 | I359T |
| CYP2C9*5 | D360E |
| CYP2C9*7 | Y358C |
| CYP2D6*1 | wild-type |
| CYP2D6*2 | R296C, S486T |
| CYP2D6*9 | K281del |
| CYP2D6*10 | P34S, S486T |
| CYP2D6*17 | T107I, R296C, S486T |
| CYP3A4*1 | wild-type |
| CYP3A4*2 | S222P |
| CYP3A4*3 | M445T |
| CYP3A4*4 | I118V |
| CYP3A4*5 | P218R |
| CYP3A4*15 | R162Q |

The following PCR primers were used.

CYP2C9*2F:
(SEQ ID NO: 26)
5'-TGTGTTCAAGAGGAAGCCCGCTG-3'

CYP2C9*2R:
(SEQ ID NO: 27)
5'-GTCCTCAATGCTGCTCTTCCCCATC-3'

CYP2C9*3F:
(SEQ ID NO: 28)
5'-CTTGACCTTCTCCCCACCAGCCTG-3'

CYP2C9*3R:
(SEQ ID NO: 29)
5'-GTATCTCTGGACCTCGTGCACCAC-3'

CYP2C9*4F:
(SEQ ID NO: 30)
5'-CTGACCTTCTCCCCACCAGCCTG-3'

CYP2C9*4R:
(SEQ ID NO: 31)
5'-TGTATCTCTGGACCTCGTGCAC-3'

CYP2C9*5F:
(SEQ ID NO: 32)
5'-GCTTCTCCCCACCAGCCTGC-3'

CYP2C9*5R:
(SEQ ID NO: 33)
5'-TCAATGTATCTCTGGACCTCGTGC-3'

CYP2C9*7F:
(SEQ ID NO: 34)
5'-GCATTGACCTTCTCCCCACCAGC-3'

CYP2C9*7R:
(SEQ ID NO: 35)
5'-CACCACGTGCTCCAGGTCTCTA-3'

CYP2D6*10AF1:
(SEQ ID NO: 36)
5'-TATTCTCACTGGCCA1TACGGCCGTGGACCTGATGCACCGGCGCCA
ACGCTGGGCTGCACGCTACTCACCAGGCCCCCTGC-3'

CYP2D6*10AR1:
(SEQ ID NO: 37)
5'-GCGGGGCACAGCACAAAGCTCATAGGGGATGGGCTCACCAGGAAA
GCAAAG-3'

CYP2D6*17F:
(SEQ ID NO: 38)
5'-TCCAGATCCTGGGTITCGGGC-3'

-continued

CYP2D6*17R:
5'-TGATGGGCACAGGCGGGCGGTC-3' (SEQ ID NO: 39)

CYP2D6*9F:
5'-GCCAAGGGGAACCCTGAGAGC-3' (SEQ ID NO: 40)

CYP2D6*9R:
5'-CTCCATCTCTGCCAGGAAGGC-3' (SEQ ID NO: 41)

CYP3A4*2F:
5'-CCAATAACAGTCTTTCCATTCCTC-3' (SEQ ID NO: 42)

CYP3A4*2R:
5'-GAGAAAGAATGGATCCAAAAAATC-3' (SEQ ID NO: 43)

CYP3A4*3F:
5'-CGAGGTTTGCTCTCATGACCATG-3' (SEQ ID NO: 44)

CYP3A4*3R:
5'-TGCCAATGCAGTTTCTGGGTCCAC-3' (SEQ ID NO: 45)

CYP3A4*4F:
5'-GTCTCTATAGCTGAGGATGAAG-3' (SEQ ID NO: 46)

CYP3A4*4R:
5'-GGCACTTTTCATAAATCCCACTG-3' (SEQ ID NO: 47)

CYP3A4*5F:
5'-GATTCTTTCTCTCAATAACAGTC-3' (SEQ ID NO: 48)

CYP3A4*5R:
5'-GATCCAAAAAATCAAATCTTAAA-3' (SEQ ID NO: 49)

CYP3A4*15F:
5'-AGGAAGCAGAGACAGGCAAGC-3' (SEQ ID NO: 50)

CYP3A4*15R:
5'-GCCTCAGATTTCTCACCAACAC-3' (SEQ ID NO: 51)

Example 6: Expression and Purification of P450 3A4

E. coli XL-10 gold (Stratagene) was used as a host for expression cultures of P450 3A4. Starter cultures were grown overnight in LB media supplemented with 100 mg per litre ampicillin. 0.5 litre Terrific Broth media plus 100 mg per litre ampicillin and 1 mM thiamine and trace elements were inoculated with 1/100 dilution of the overnight starter cultures. The flasks were shaken at 37° C. until cell density $OD_{600}$ was 0.4 then δ-Aminolevulinic acid (ALA) was added to the cells at 0.5 mM for 20 min at 30° C. The cells were supplemented with 50 μM biotin then induced with optimum concentration of IPTG (30-100 μM) then shaken overnight at 30° C.

Figure 14:
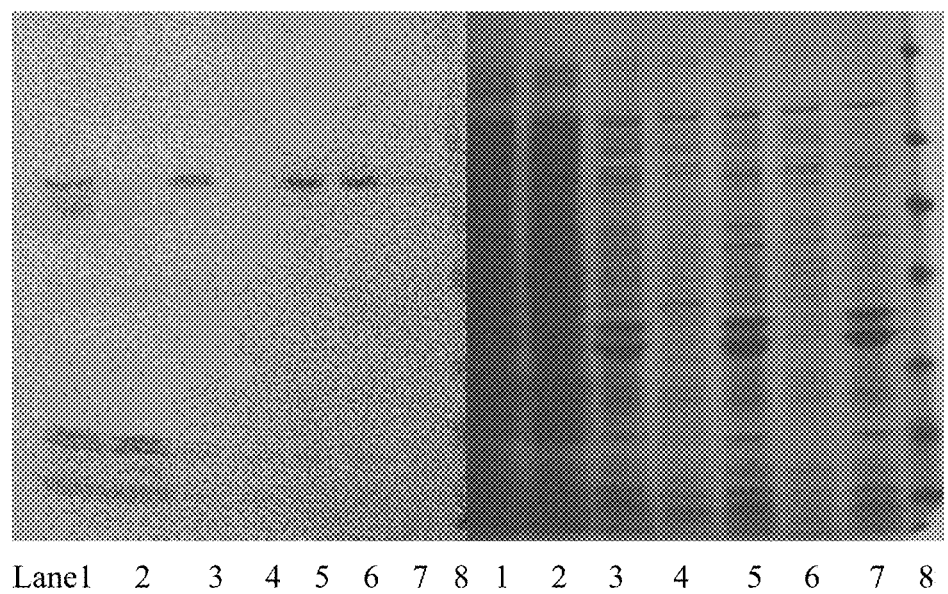
FIG. 14 shows a western blot and coomassie-stained gel of purification of cytochrome P450 3A4 from E. coli. Samples from the purification of cytochrome P450 3A4 were run on SDS-PAGE, stained for protein using coomassie or Western blotted onto nitrocellulose membrane, probed with streptavidin-HRP conjugate and visualised using DAB stain.

The E. coli cells from 0.5 litre cultures were divided into 50 ml aliquots, cells pelleted by centrifugation and cell pellets stored at −20° C. Cells from each pellet were lysed by resuspending in 5 ml buffer A (100 mM Tris buffer pH 8.0 containing 100 mM EDTA, 10 mM β-mercaptoethanol, 10× stock of Protease inhibitor cocktail-Roche 1836170, 0.2 mg/ml Lysozyme). After 15 minutes incubation on ice 40 ml of ice-cold deionised water was added to each resuspended cell pellet and mixed. 20 mM Magnesium Chloride and 5 μg/ml DNaseI were added. The cells were incubated for 30 min on ice with gentle shaking after which the lysed E. Coli cells were pelleted by centrifugation for 30 min at 4000 rpm. The cell pellets were washed by resuspending in 10 ml buffer B (100 mM Tris buffer pH 8.0 containing 10 mM β-mercaptoethanol and a 10× stock of Protease inhibitor cocktail-Roche 1836170) followed by centrifugation at 4000 rpm. Membrane associated protein was then solubilised by the addition of 2 ml buffer C (50 mM potassium phosphate pH 7.4, 10× stock of Protease inhibitor cocktail-Roche 1836170, 10 mM β-mercaptoethanol, 0.5 M NaCl and 0.3% (v/v) Igepal CA-630) and incubating on ice with gentle agitation for 30 minutes before centrifugation at 10,000 g for 15 min at 4° C. and the supernatant (FIG. 14) was then applied to Talon resin (Clontech).

A 0.5 ml column of Ni-NTA agarose (Qiagen) was poured in disposable gravity columns and equilibrated with 5 column volumes of buffer C. Supernatant was applied to the column after which the column was successively washed with 4 column volumes of buffer C, 4 column volumes of buffer D (50 mM potassium phosphate pH 7.4, 10× stock of Protease inhibitor cocktail-Roche 1836170, 10 mM β-mercaptoethanol, 0.5 M NaCl and 20% (v/v) Glycerol) and 4 column volumes of buffer D+50 mM Imidazole before elution in 4 column volumes of buffer D+200 mM Imidazole (FIG. 15). 0.5 ml fractions were collected and protein containing fractions were pooled aliquoted and stored at −80° C.

Example 7: Determination of Heme Incorporation into P450s

Purified P450s were diluted to a concentration of 0.2 mg/ml in 20 mM potassium phosphate (pH 7.4) in the presence and absence of 10 mM KCN and an absorbance scan measured from 600-260 nm. The percentage bound heme was calculated based on an extinction coefficient $\varepsilon_{420}$ of 100 $mM^{-1}cm^{-1}$.

Example 8: Reconstitution and Assay of Cytochrome P450 Enzymes into Liposomes with NADPH-Cytochrome P450 Reductase Liposomes are prepared by dissolving a 1:1:1 mixture of 1,2-dilauroyl-sn-glycero-3-phosphocholine, 1,2-dileoyl-sn-glycero-3-phosphocholine, 1,2-dilauroyl-sn-glycero-3-phosphoserine in chloroform, evaporating to dryness and subsequently resuspending in 20 mM potassium phosphate pH 7.4 at 10 mg/ml. 4 μg of liposomes are added to a mixture of purified P450 2D6 (20 pmol), NADPH P450 reductase (40 pmol), cytochrome b5 (20 pmol) in a total volume of 10 μl and preincubated for 10 minutes at 37° C.

After reconstitution of cytochrome P450 enzymes into liposomes, the liposomes are diluted to 100 μl in assay buffer in a black 96 well plate, containing HEPES/KOH (pH 7.4, 50 mM), NADP+ (2.6 mM), glucose-6-phosphate (6.6 mM), $MgCl_2$ (6.6 mM) and glucose-6-phosphate dehydrogenase (0.4 units/ml). Assay buffer also contains an appropriate fluorogenic substrate for the cytochrome P450 isoform to be assayed: for P450 2D6 AMMC, for P450 3A4 dibenzyl fluorescein (DBF) or resorufin benzyl ether (BzRes) can be used and for 2C9 dibenzyl fluorescein (DBF). The reactions are stopped by the addition of 'stopping solution' (80% acetonitrile buffered with Tris) and products are read using the appropriate wavelength filter sets in a fluorescent plate reader (FIG. 16).

P450s can also be activated chemically by, for example, the addition of 200 μM cumene hydroperoxide in place of the both the co-enzymes and regeneration solution (FIG. 17).

In addition fluorescently measured rates of turnover can be measured in the presence of inhibitors.

Example 9: Detection of Drug Binding to Immobilised P450s CYP3A4

Purified CYP3A4 (10 μg/ml in 50 mM HEPES/0.01% CHAPS, pH 7.4) was placed in streptavidin immobiliser plates (Exiqon) (100 μl per well) and shaken on ice for 1 hour. The wells were aspirated and washed twice with 50 mM HEPES/0.01% CHAPS. [$^3$H]-ketoconazole binding to immobilised protein was determined directly by scintillation counting. Saturation experiments were performed using [$^3$H]ketoconazole (5 Ci/mmol, American Radiochemicals Inc., St. Louis) in 50 mM HEPES pH 7.4, 0.01% CHAPS and 10% Superblock (Pierce) (FIG. 18). Six concentrations of ligand were used in the binding assay (25-1000 nM) in a final assay volume of 100 μl. Specific binding was defined as that displaced by 100 μM ketoconazole. Each measurement was made in duplicate. After incubation for 1 hour at room temperature, the contents of the wells were aspirated and the wells washed three times with 150 μl ice cold assay buffer. 100 μl MicroScint 20 (Packard) was added to each well and the plates counted in a Packard TopCount microplate scintillation counter (FIG. 18).

Example 10: Chemical Activation of Tagged, Immobilised CYP3A4

CYP3A4 was immobilised in streptavidin immobiliser plates as described in Example 9 and was then incubated with dibenzyl fluorescein and varying concentrations (0-300 μM) of cumene hydrogen peroxide. End point assays demonstrated that the tagged, immobilised CYP3A4 was functional in a turn-over assay with chemical activation (FIG. 19).

Example 11: Immobilisation of P450s Through Gel Encapsulation of Liposomes or Microsomes After reconstitution of cytochrome P450 enzymes together with NADPH-cytochrome P450 reductase in liposomes or microsomes, these can then be immobilised on to a surface by encapsulation within a gel matrix such as agarose, polyurethane or polyacrylamide.

For example, low melting temperature (LMT) (1% w/v) agarose was dissolved in 200 mM potassium phosphate p1H 7.4. This was then cooled to 37° C. on a heating block. Microsomes containing cytochrome P450 3A4, cytochrome b5 and NADPH-cytochrome P450 reductase were then diluted into the LMT agarose such that 50 μl of agarose contained 20, 40 and 20 pmol of P450 3A4, NADPH-cytochrome P450 reductase and cytochrome b5 respectively. 50 μl of agarose-microsomes was then added to each well of a black 96 well microtitre plate and allowed to solidify at room temperature.

To each well, 100 μl of assay buffer was added and the assay was conducted as described previously (for example, Example 8) for conventional reconstitution assay. From the data generated a comparison of the fundamental kinetics of BzRes oxidation and ketoconazole inhibition was made (Table 6) which showed that the activity of the CYP3A4 was retained after gel-encapsulation.

TABLE 6

Comparison of kinetic parameters for BZRes oxidation and inhibition by ketoconazole for cytochrome P450 3A4 microsomes in solution and encapsulated in agarose.

|  | Gel encapsulated | Soluble |
|---|---|---|
| BzRes Oxidation |  |  |
| $K_M$ (μM) | 49 (18) | 20 (5) |
| $V_{max}$ (% of soluble) | 50 (6) | 100 (6) |
| Ketoconazole inhibition |  |  |
| IC50 (nM) | 86 (12) | 207 (54) |

For estimation of $K_M$ and $V_{max}$ for BzRes assays were performed in the presence of varying concentrations of BzRes up to 320 μM. Ketoconazole inhibition was performed at 50 μM BzRes with 7 three-fold dilutions of ketoconazole from 5 μM. Values in parenthesis indicate standard errors derived from the curve fitting.

The activity of the immobilised P450s was assessed over a period of 7 days (FIG. 20). Aliquots of the same protein preparation stored under identical conditions, except that they were not gel-encapsulated, were also assayed over the same period, which revealed that the gel encapsualtion confers significant stability to the P450 activity.

Example 12: Quantitative Determination of Affect of 3A4 Polymorphisms on Activity Purified cytochrome P450 3A4 isoforms *1, *2, *3, *4, *5 & *15 (approx 1 μg) were incubated in the presence of BzRes and cumene hydrogen peroxide (200 μM) in the absence and presence of ketoconazole at room temperature in 200 mM $KPO_4$ buffer pH 7.4 in a total volume of 100 μl in a 96 well black microtitre plate. A minimum of duplicates were performed for each concentration of BzRes or ketoconazole. Resorufin formation of was measured over time by the increase in fluorescence (520 nm and 580 nm excitation and emission filters respectively) and initial rates were calculated from progress curves (FIG. 21).

For estimation of $K_M^{app}$ and $V_{max}^{app}$ for BzRes, background rates were first subtracted from the initial rates and then were plotted against BzRes concentration and curves were fitted describing conventional Michaelis-Menton kinetics:

$$V = V_{max}/(1+(K_M/S))$$

where V and S are initial rate and substrate concentration respectively. $V_{max}$ values were then normalised for cytochrome P450 concentration and scaled to the wild-type enzyme (Table 7).

For estimation of $IC_{50}$ for ketoconazole, background rates were first subtracted from the initial rates which were then converted to a % of the uninhibited rate and plotted against ketoconazole concentration (FIG. 22). $IC_{50}$ inhibition curves were fitted using the equation:

$$V = 100(1+(I/IC_{50}))$$

where V and I are initial rate and inhibitor concentration respectively. The data obtained are shown in Table 7:

TABLE 7

Kinetic parameters for BzRes turnover and its inhibition by ketoconazole for cytochrome P450 3A4 isoforms.

|  | $V_{max}$ BzRes | $K_M$ BzRes (µM) | $IC_{50}$ ketoconazole (µM) |
|---|---|---|---|
| 3A4*WT | 100 (34) | 104 (25) | 0.91 (0.45) |
| 3A4*2 | 65 (9) | 62 (4) | 0.44 (0.11) |
| 3A4*3 | 93 (24) | 54 (13) | 1.13 (0.16) |
| 3A4*4 | 69 (22) | 111 (18) | 0.88 (0.22) |
| 3A4*5 | 59 (16) | 101 (11) | 1.96 (0.96) |
| 3A4*15 | 111 (23) | 89 (11) | 0.59 (0.20) |

The parameters were obtained from the fits of Michaelis-Menton and $IC_{50}$ inhibition curves to the data in FIGS. 21 & 22. Values in parenthesis are standard errors obtained from the curve fits.

Example 13: Array-Based Assay of Immobilised CYP3A4 Polymorphisms

Cytochrome P450 polymorphisms can be assayed in parallel using an array format to identify subtle differences in activity with specific small molecules. For example, purified cytochrome P450 3A4 isoforms *1, *2, *3, *4, *5 & *15 can be individually reconstituted in to liposomes with NADPH-cytochrome P450 reductase as described in Example 11. The resultant liposomes preparation can then be diluted into LMP agarose and immobilised into individual wells of a black 96 well microtitre plate as described in Example 11. The immobilised proteins can then be assayed as described in Example 11 by adding 100 µl of assay buffer containing BzRes+/−ketoconazole to each well.

Chemical activation (as described in Example 12) can also be used in an array format. For example, purified cytochrome P450 3A4 isoforms *1, *2, *3, *4, *5 & *15 can be individually reconstituted in to liposomes without NADPH-cytochrome P450 reductase and the resultant liposomes can be immobilised via encapsulation in agarose as described in Example 11. The cytochrome P450 activity in each well can then be measured as described in Example 12 by 100 µl of 200 mM $KPO_4$ buffer pH 7.4 containing BzRes and cumene hydrogen peroxide (200 µM), +/− ketoconazole, to each well.

In summary, the Inventors have developed a novel protein array technology for massively parallel, high-throughout screening of SNPs for the biochemical activity of the encoded proteins. Its applicability was demonstrated through the analysis of various functions of wild type p53 and 46 SNP versions of p53 as well as with allelic variants of p450. The same surface and assay detection methodologies can now be applied to other more diverse arrays currently being developed. Due to the small size of the collection of proteins being studied here, the spot density of our arrays was relatively small, and each protein was spotted in quadruplicate. Using current robotic spotting capabilities it is possible to increase spot density to include over 10,000 proteins per array.

INCORPORATION BY REFERENCE

The entire disclosure of each of the aforementioned patent and scientific documents cited hereinabove is expressly incorporated by reference herein.

EQUIVALENTS

The invention may be embodied in other specific forms without departing from the spirit or essential characteristics thereof. The foregoing embodiments are therefore to be considered in all respects illustrative rather than limiting on the invention described herein. The scope of the invention is thus indicated by the appended claims rather than by the foregoing description, and all changes that come within the meaning and range of equivalency of the claims are intended to be embraced by reference therein.

---

The invention claimed is:

1. A method of simultaneously quantifying the relative functional properties of members of a set of protein moieties which are variants of a protein that differ in their amino acid sequences at one or more positions, the protein moieties of the set of protein moieties being encoded by naturally-occurring variants of a DNA sequence of interest that map to a common chromosomal locus; the method comprising the steps of:
   a) obtaining two or more replicate protein arrays, each array comprising a surface on which the protein moieties of the set of protein moieties are deposited at spatially defined locations, and bringing each array into contact with a test substance in solution at a known concentration, where the concentration of the test substance in solution that is applied to at least one of the two or more replicate arrays is different from the concentration of the test substance in solution that is applied to at least one other of the two or more replicate arrays;
   b) measuring the interaction of the test substance with the protein moieties on each array at each known concentration of the test substance; and
   c) quantifying the affinity of the interaction of said test substance with each one of the protein moieties;
   wherein the protein moieties of the set of protein moieties are immobilized on the surface by attachment to the surface through a common marker moiety appended to each of the protein moieties of the set of protein moieties;
   wherein the protein moieties of the set of protein moieties are attached to the surface through the common marker moiety such that the protein moieties have their naturally occurring function and/or activity; and
   wherein the surface is coated with a porous or non-porous chemical surface coating that is capable of resisting non-specific protein absorption.

2. The method of claim 1, wherein the common marker moiety appended to each of the protein moieties of the set of protein moieties is Biotin Carboxyl Carrier Protein (BCCP).

3. The method of claim 1, wherein the protein moieties of the set of protein moieties are of human origin.

4. The method of claim 1, wherein the variants of the DNA sequence of interest differ by one or more naturally-occurring mis-sense mutations, insertions or deletions.

5. The method of claim 1, wherein the protein moieties of the set of protein moieties comprise proteins associated with a disease state, associated with drug metabolism or are uncharacterized.

6. The method of claim 1, wherein the protein moieties of the set of protein moieties are enzymatically active.

7. The method of claim 6, wherein the protein moieties of the set of protein moieties are drug metabolizing enzymes.

8. The method of claim 1, wherein the protein moieties of the set of protein moieties are drug metabolising enzymes which are activated by contact with an accessory protein or by chemical treatment.

9. The method of claim 1, wherein the protein moieties of the set of protein moieties comprise a wild type p53 and at least one allelic variant thereof.

10. The method of claim 1, wherein the protein moieties of the set of protein moieties comprise a wild type p450 and at least one allelic variant thereof.

11. The method of claim 1, wherein the surface is a flat surface.

12. The method of claim 11, wherein the flat surface is selected from a glass slide, a polypropylene slide, a polystyrene slide, a membrane made of nitrocellulose, a membrane made of PVDF, a membrane made of nylon, and a membrane made of phosphocellulose.

13. The method of claim 1, wherein the surface is coated or derivatized by chemical treatment.

14. The method of claim 1, wherein step (c) comprises determining the binding or catalytic constant ($K_D$ or $K_M$) for the interaction of said test substance with each one of the protein moieties.

* * * * *